United States Patent
Huh et al.

(10) Patent No.: US 11,678,574 B2
(45) Date of Patent: Jun. 13, 2023

(54) COMPOUND AND ORGANIC LIGHT EMITTING DIODE COMPRISING SAME

(71) Applicant: LG CHEM, LTD., Seoul (KR)

(72) Inventors: Jungoh Huh, Daejeon (KR); Sung Kil Hong, Daejeon (KR); Dong Uk Heo, Daejeon (KR); Miyeon Han, Daejeon (KR); Jae Tak Lee, Daejeon (KR); Junghoon Yang, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 289 days.

(21) Appl. No.: 16/761,557

(22) PCT Filed: Mar. 22, 2019

(86) PCT No.: PCT/KR2019/003361
§ 371 (c)(1),
(2) Date: May 5, 2020

(87) PCT Pub. No.: WO2019/182400
PCT Pub. Date: Sep. 26, 2019

(65) Prior Publication Data
US 2020/0266356 A1 Aug. 20, 2020

(30) Foreign Application Priority Data
Mar. 22, 2018 (KR) .................. 10-2018-0033283

(51) Int. Cl.
*C07D 239/26* (2006.01)
*C07D 401/10* (2006.01)
(Continued)

(52) U.S. Cl.
CPC ......... *H10K 85/654* (2023.02); *C07D 239/26* (2013.01); *C07D 401/10* (2013.01);
(Continued)

(58) Field of Classification Search
CPC ................ C07F 15/0033; C07F 15/002; C07F 15/0086; C07F 9/6512; H01L 51/0085;
(Continued)

(56) References Cited

U.S. PATENT DOCUMENTS

| 2002/0172420 A1 | 11/2002 | Nicolas | |
|---|---|---|---|
| 2013/0032764 A1* | 2/2013 | Buesing | ................ H05B 33/14 252/500 |

(Continued)

FOREIGN PATENT DOCUMENTS

| CN | 105308035 A | 2/2016 | |
|---|---|---|---|
| CN | 107922359 A * | 4/2018 | .......... C07D 251/24 |

(Continued)

OTHER PUBLICATIONS

"Chemical Abstract Compound Registry No. 2125611-00-7," STN Express, entered STN Sep. 7, 2017, 4 pages, retrieved Jun. 27, 2019.

*Primary Examiner* — Younes Boulghassoul
*Assistant Examiner* — Quinton A Brasfield
(74) *Attorney, Agent, or Firm* — Dentons US LLP

(57) ABSTRACT

Provided is a compound of Chemical Formula 1:

HAr-L1-L2-Ar1      Chemical Formula 1 wherein:
HAr is a group of the following Chemical Formula A-1 or A-2; L1 and L2 are the same as or different from each other, and each independently is a direct bond, a substituted or unsubstituted monocyclic or polycyclic arylene group, or a substituted or unsubstituted monocyclic or polycyclic heteroarylene group; and
Ar1 is a substituted or unsubstituted monocyclic or polycyclic aryl group, or a substituted or unsubstituted monocyclic or polycyclic heteroaryl group;
(Continued)

| 11 |
|---|
| 8 |
| 7 |
| 6 |
| 4 |
| 3 |
| 2 |
| 1 |

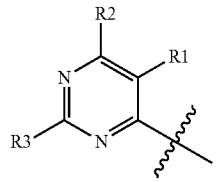

Chemical Formula A-1

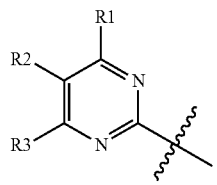

Chemical Formula A-2 wherein:
R1 to R3 are the same as or different from each other, and each independently is a substituted or unsubstituted linear or branched alkyl group; and

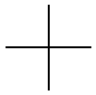

is a site bonding to L1 of Chemical Formula 1,
and an organic light emitting device comprising the same.

19 Claims, 6 Drawing Sheets

(51) Int. Cl.
C07D 403/10 (2006.01)
C07D 405/10 (2006.01)
C07D 409/10 (2006.01)
C07D 471/04 (2006.01)
C07D 495/04 (2006.01)
C07F 9/6512 (2006.01)

(52) U.S. Cl.
CPC ......... *C07D 403/10* (2013.01); *C07D 405/10* (2013.01); *C07D 409/10* (2013.01); *C07D 471/04* (2013.01); *C07D 495/04* (2013.01); *C07F 9/6512* (2013.01); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02)

(58) Field of Classification Search
CPC ............. H01L 51/5004; H01L 51/0088; H01L 51/5024; H01L 51/0087; H01L 2251/552; H01L 2251/308; H01L 51/5016; H01L 51/0067; H01L 51/0072; H01L 51/0073; H01L 51/0074; H01L 51/5056; C07D 401/10; C07D 403/10; C07D 405/10; C07D 409/10; C07D 471/04; C07D 495/04; C07D 239/26; H10K 85/654; H10K 50/11
See application file for complete search history.

(56) References Cited

U.S. PATENT DOCUMENTS

| | | |
|---|---|---|
| 2014/0330013 A1 | 11/2014 | Aihara et al. |
| 2015/0243897 A1* | 8/2015 | Montenegro ........ H10K 85/654 544/215 |
| 2016/0056388 A1* | 2/2016 | Oka ..................... C07D 239/26 544/180 |
| 2016/0141514 A1* | 5/2016 | Lee ...................... C07D 251/24 544/333 |
| 2017/0279054 A1* | 9/2017 | Huang ................. H10K 85/626 |
| 2017/0346017 A1* | 11/2017 | Nakano ................ C07D 401/14 |
| 2018/0051007 A1* | 2/2018 | Jung ..................... C09K 11/06 |
| 2018/0090686 A1* | 3/2018 | Yoon .................... C07D 409/14 |
| 2018/0248126 A1* | 8/2018 | Huh ...................... C07F 9/65685 |
| 2018/0323379 A1 | 11/2018 | Kim et al. |
| 2018/0337341 A1 | 11/2018 | Heo et al. |

FOREIGN PATENT DOCUMENTS

| | | | |
|---|---|---|---|
| EP | 3150579 A1 * | 4/2017 | ........... C07D 213/16 |
| JP | 2014111548 | 6/2014 | |
| KR | 10-20030012890 | 2/2003 | |
| KR | 10-20150124000 | 11/2015 | |
| KR | 10-20170053534 | 5/2017 | |
| KR | 10-1755986 | 7/2017 | |
| KR | 10-20170127956 | 11/2017 | |
| KR | 10-20170134841 | 12/2017 | |
| KR | 10-20180015794 | 2/2018 | |

* cited by examiner

【FIG. 1】

| |
|---|
| 11 |
| 8 |
| 7 |
| 6 |
| 4 |
| 3 |
| 2 |
| 1 |

【FIG. 2】

| |
|---|
| 11 |
| 8 |
| 6 |
| 5 |
| 4 |
| 3 |
| 2 |
| 1 |

【FIG. 3】

| |
|---|
| 11 |
| 8 |
| 6b |
| 4b |
| 13 |
| 12 |
| 9a |
| 6a |
| 5 |
| 4a |
| 3 |
| 2 |
| 1 |

【FIG. 4】

| |
|---|
| 11 |
| 9c |
| 6c |
| 4c |
| 13b |
| 12b |
| 9b |
| 6b |
| 4b |
| 13a |
| 12a |
| 9a |
| 6a |
| 5 |
| 4a |
| 3 |
| 2 |
| 1 |

【FIG. 5】

| |
|---|
| 14 |
| 11 |
| 10 |
| 9c |
| 6BFb |
| 4e |
| 4d |
| 13b |
| 12b |
| 9b |
| 6GP |
| 6YGP |
| 6RP |
| 4c |
| 13a |
| 12a |
| 9a |
| 6BFa |
| 4b |
| 4a |
| 3 |
| 2 |
| 1 |

【FIG. 6】

| |
|---|
| 14 |
| 11 |
| 10 |
| 9c |
| 6BFb |
| 4e |
| 4d |
| 13b |
| 12b |
| 9b |
| 6GP |
| 6RP |
| 4c |
| 13a |
| 12a |
| 9a |
| 6BFa |
| 4b |
| 4a |
| 3 |
| 2 |
| 1 |

【FIG. 7】

| |
|---|
| 14 |
| 11 |
| 10 |
| 9c |
| 6BFc |
| 4f |
| 4e |
| 13b |
| 12b |
| 9b |
| 6BFb |
| 4d |
| 4c |
| 13a |
| 12a |
| 9a |
| 6BFa |
| 4b |
| 4a |
| 4pa |
| 2 |
| 1 |

[FIG. 8]

| 14 |||
|---|---|---|
| 11 |||
| 10 |||
| 9b |||
| 9a |||
| 6RP | 6GP | 6BF |
| 4R | 4G | 4B |
| 4p |||
| 2 |||
| 1 |||

COMPOUND AND ORGANIC LIGHT EMITTING DIODE COMPRISING SAME

CROSS-REFERENCE TO RELATED APPLICATIONS

This application is a National Stage Application of International Application No. PCT/KR2019/003361 filed on Mar. 22, 2019, which claims priority to and the benefits of Korean Patent Application No. 10-2018-0033283, filed with the Korean Intellectual Property Office on Mar. 22, 2018, the entire contents of which are incorporated herein by reference.

TECHNICAL FIELD

The present specification relates to a compound and an organic light emitting device comprising the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a compound of Chemical Formula 1, and an organic light emitting device comprising the same.

Technical Solution

One embodiment of the present specification provides a compound of Chemical Formula 1:

HAr-L1-L2-Ar1          Chemical Formula 1

In Chemical Formula 1:
HAr is a group of the following Chemical Formula A-1 or A-2;
L1 and L2 are the same as or different from each other, and each independently is a direct bond, a substituted or unsubstituted monocyclic or polycyclic arylene group, or a substituted or unsubstituted monocyclic or polycyclic heteroarylene group; and
Ar1 is a substituted or unsubstituted monocyclic or polycyclic aryl group, or a substituted or unsubstituted monocyclic or polycyclic heteroaryl group;

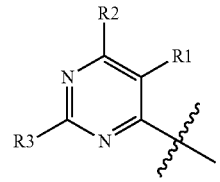

Chemical Formula A-1

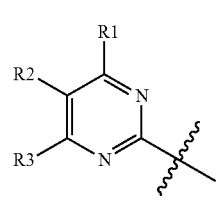

Chemical Formula A-2 wherein in Chemical Formulae A-1 and A-2:
R1 to R3 are the same as or different from each other, and each independently is a substituted or unsubstituted linear or branched alkyl group; and

is a site bonding to L1 of Chemical Formula 1.

organic light emitting device comprising a first electrode; a second electrode provided opposite to the first electrode; and one or more organic material layers provided between the first electrode and the second electrode, wherein one or more layers of the organic material layers comprises the compound of Chemical Formula 1.

Advantageous Effects

An organic light emitting device comprising a compound of Chemical Formula 1 according to the present specification as a material of an organic material layer has properties of low driving voltage, high efficiency and/or long lifetime.

DESCRIPTION OF DRAWINGS

FIG. 1 illustrates an organic light emitting device according to one embodiment of the present specification.
FIG. 2 illustrates an organic light emitting device according to another embodiment of the present specification.
FIGS. 3 to 7 illustrate examples of an organic light emitting device comprising two or more stacks.
FIG. 8 illustrates an organic light emitting device according to another embodiment of the present specification.

DETAILED DESCRIPTION

Hereinafter, the present specification will be described in more detail.

One embodiment of the present specification provides a compound of Chemical Formula 1.

Chemical Formulae A-1 and A-2 according to one embodiment of the present specification have substituents bonding to all three $sp^2$ positions of R1 to R3, whereas the following structures, an existing pyrimidine core, are structures having substituents bonding to R and R', two positions of three $sp^2$ positions:

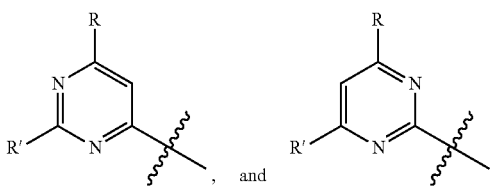

Accordingly, Chemical Formulae A-1 and A-2 according to one embodiment of the present specification are a new pyrimidine structure having a site vulnerable to a chemical reaction removed, which means that chemical stability of Chemical Formula 1 is enhanced, and an organic light emitting device including the structure in an organic material layer significantly decreases probability of dissociation caused by electrons or holes generated when driving the organic light emitting device, and as a result, a lowered voltage, increased efficiency and greatly enhanced lifetime properties can be obtained in the organic light emitting device.

In addition, Chemical Formulae A-1 and A-2 according to one embodiment of the present specification include substituents at the three $sp^2$ positions, and therefore, more readily control electron quantities than existing pyrimidine cores illustrated above, and both efficiency and lifetime can be enhanced in an organic light emitting device including the structure in an organic material layer thereof.

Chemical Formulae A-1 and A-2 according to one embodiment of the present specification include substituents at the three $sp^2$ positions, which increases a molecular weight of Chemical Formula 1, and therefore, when forming a film using the compound of Chemical Formula 1, an effect of hardening the film quality is obtained.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a cyano group, a nitro group, an alkyl group, a cycloalkyl group, an alkoxy group, an aryloxy group, an alkylthioxy group, an arylthioxy group, an amine group, a phosphine oxide group, an aryl group, and a heteroaryl group, being substituted with a substituent linking two or more substituents among the substituents selected from the group, two substituents selected from the group bonding to each other to form a spiro structure, or having no substituents. For example, "a substituent linking two or more substituents" can include a biphenyl group. In other words, a biphenyl group can be an aryl group, or interpreted as a substituent linking two phenyl groups.

In the definition of the term "substituted or unsubstituted", the "two substituents selected from the group bonding to each other to form a spiro structure" means "'any substituent selected from the group' spiro bonding to 'another substituent substituting an atom substituted with the corresponding substituent' to form a spiro ring".

In the present specification,

means a site bonding to other substituents or bonding sites.

In the present specification, the halogen group can be fluorine, chlorine, bromine or iodine.

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methyl-heptyl, 2-ethylhexyl, 2-propylpentyl, n-nonyl, 2,2-dimethyl-heptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butyl-cyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, n-butoxy, isobutoxy, tert-butoxy, sec-butoxy, n-pentyloxy, neopentyl-oxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group can be selected from the group consisting of —$NH_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. In one embodiment of the present specification, the amine group is —$N(R_p)(R_q)$, and $R_p$ and $R_q$ are the same as or different from each other and each independently is hydrogen, deuterium, a substituted or unsubstituted alkyl group, a substituted or unsubstituted aryl group, or a substituted or unsubstituted heteroaryl group. Specific examples of the amine group can include a methylamine group, a dimethylamine group, an ethylamine group, a diethylamine group, a phenylamine group, a naphthylamine group, a biphenylamine group, an anthracenyl-amine group, a 9-methylanthracenylamine group, a diphenyl-amine group, a ditolylamine group, an N-phenyltolylamine group, a diphenylamine group, an N-phenylbiphenylamine group, an N-phenylnaphthylamine group, an N-biphenylnaphthylamine group, an N-naphthylfluorenylamine group, an N-phenyl-phenanthrenylamine group, an N-biphenylphenanthrenylamine group, an N-phenylfluorenylamine group, an N-phenyl-terphenylamine group, an N-phenanthrenylfluorenylamine group, an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, examples of the alkylamine group include a substituted or unsubstituted monoalkylamine group or a substituted or unsubstituted dialkylamine group. The alkyl group in the alkylamine group can be a linear or branched alkyl group. The alkylamine group including two or more alkyl groups can include linear alkyl groups, branched alkyl groups, or both linear alkyl groups and branched alkyl groups. For example, the alkyl group in the alkylamine group can be selected from among the examples of the alkyl group described above.

In the present specification, the alkyl group in the N-alkylarylamine group, the alkylthioxy group and the N-alkylheteroarylamine group is the same as the examples of the alkyl group described above. Specific examples of the alkylthioxy group can include a methylthioxy group, an ethylthioxy group, a tert-butylthioxy group, a hexylthioxy group, an octylthioxy group and the like, but are not limited thereto.

In the present specification, specific examples of the phosphine oxide group can include an alkylphosphine oxide group, an arylphosphine oxide group and the like, and more specifically, a diphenylphosphine oxide group, a dinaphthylphosphine oxide group and the like, but are not limited thereto. In the present specification, the phosphine oxide group means —P(=O)($R_m$)($R_n$), and $R_m$ and $R_n$ are the same as or different from each other and each independently is hydrogen, deuterium, a substituted or unsubstituted alkyl group, a substituted or unsubstituted aryl group, or a substituted or unsubstituted heteroaryl group. In the present specification, —P(=O)($C_6H_5$)$_2$ is referred to as a diphenylphosphoryl group.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific example of the polycyclic aryl group can include a naphthyl group (naphthalenyl group), an anthracenyl group, a phenanthrenyl group, a triphenylenyl group, a pyrenyl group, a phenalenyl group, a perylenyl group, a chrysenyl group, a fluorenyl group, a fluoranthenyl group and the like, but are not limited thereto.

In the present specification, the fluorenyl group can be substituted, and adjacent groups can bond to each other to form a ring.

When the fluorenyl group is substituted,

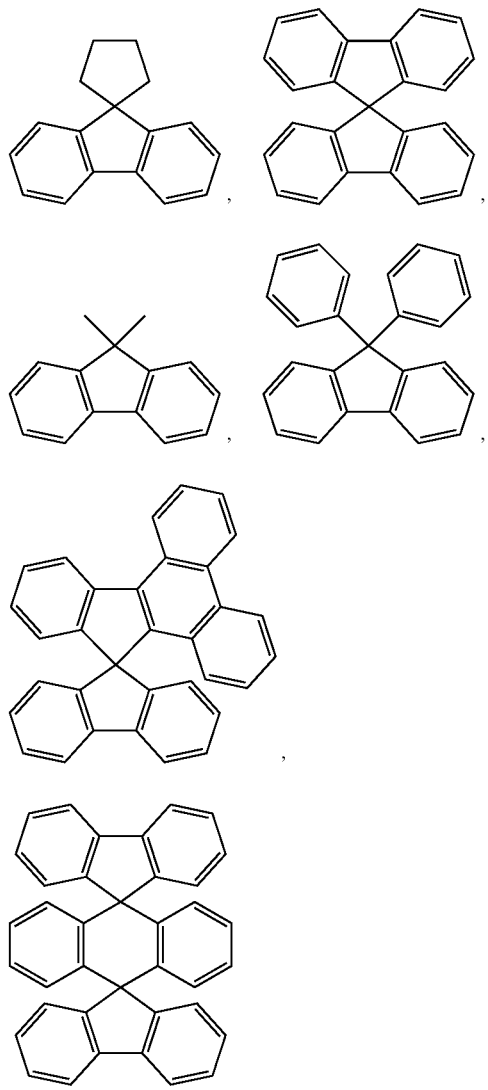

and the like can be included. However, the structure is not limited thereto.

In the present specification, the substituted fluorenyl group includes a spiro-substituted fluorenyl group, and the spiro-substituted fluorenyl group can be interpreted as a 'spiro-substituted aryl group' or 'substituted aryl group'. In the present specification, the spiro-substituted fluorenyl group means, for example, a substituent in which $G_1$ and $G_2$ of

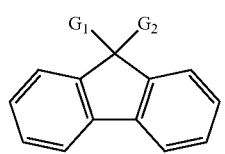

bond to form a ring. The spiro-substituted fluorene can include

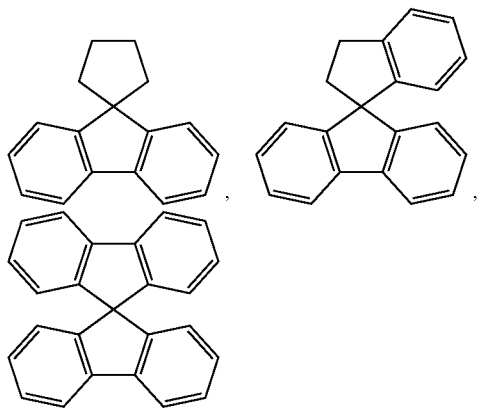

and the like, but are not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the aryl group in the aryloxy group, the arylthioxy group, the N-arylalkylamine group and the N-arylheteroarylamine group is the same as the examples of the aryl group described above. Specific examples of the aryloxy group can include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthrenyloxy group, a 3-phenanthrenyloxy group, a 9-phenanthrenyloxy group and the like. Specific examples of the arylthioxy group can include a phenylthioxy group, a 2-methylphenylthioxy group, a 4-tert-butylphenylthioxy group and the like. However, the aryloxy group and the arylthioxy group are not limited thereto.

In the present specification, examples of the arylamine group include a substituted or unsubstituted monoarylamine group, or a substituted or unsubstituted diarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophenyl group, a furanyl group, a pyrrolyl group, an imidazolyl group, a thiazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolyl group, a quinoxalinyl group, a phthalazinyl group, a pyridopyrimidinyl group, a pyridopyrazinyl group, a pyrazinopyrazinyl group, a pyridoindolyl group, a benzothienopyrimidyl group, an indenocarbazolyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthridinyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group include a substituted or unsubstituted monoheteroarylamine group, or a substituted or unsubstituted diheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above can be applied thereto except for each being a divalent group.

In the present specification, the heteroarylene group means a heteroaryl group having two bonding sites, that is, a divalent group. Descriptions on the heteroaryl group provided above can be applied thereto except for each being a divalent group.

According to one embodiment of the present specification, Chemical Formula 1 is one of the following Chemical Formula 1-1 or 1-2:

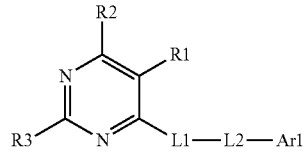

Chemical Formula 1-1

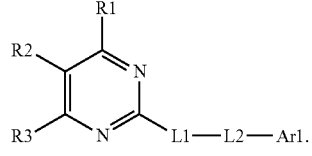

Chemical Formula 1-2

In Chemical Formulae 1-1 and 1-2:
L1, L2 and Ar1 have the same definitions as in Chemical Formula 1; and
R1 to R3 have the same definitions as in Chemical Formulae A-1 and A-2.

According to one embodiment of the present specification, L1 and L2 are the same as or different from each other, and each independently is a direct bond, a monocyclic arylene group that is unsubstituted or is substituted with an alkyl group or an aryl group, or a polycyclic arylene group.

According to one embodiment of the present specification, L1 and L2 are the same as or different from each other, and each independently is a direct bond, a substituted or unsubstituted phenylene group, a substituted or unsubstituted $C_{10-30}$ polycyclic arylene group, a substituted or unsubstituted monocyclic $C_{2-5}$ heteroarylene group, or a substituted or unsubstituted polycyclic $C_{2-30}$ heteroarylene group.

According to one embodiment of the present specification, L1 and L2 are the same as or different from each other, and each independently is a direct bond, a substituted or unsubstituted phenylene group, a substituted or unsubstituted $C_{10-25}$ polycyclic arylene group, a substituted or unsubstituted $C_{2-5}$ monocyclic heteroarylene group, or a substituted or unsubstituted $C_{2-25}$ polycyclic heteroarylene group.

According to one embodiment of the present specification, L1 and L2 are the same as or different from each other, and each independently is a direct bond, a substituted or unsubstituted phenylene group, a substituted or unsubstituted $C_{10-20}$ polycyclic arylene group, a substituted or unsubstituted $C_{2-5}$ monocyclic heteroarylene group, or a substituted or unsubstituted $C_{2-20}$ polycyclic heteroarylene group.

According to one embodiment of the present specification, L1 and L2 are the same as or different from each other, and each independently is a direct bond, a substituted or unsubstituted phenylene group, a substituted or unsubstituted biphenylene group, a substituted or unsubstituted divalent fluorenyl group, a substituted or unsubstituted divalent naphthalene group, a substituted or unsubstituted divalent spiro[fluorene-9,9'-xanthen]yl group, a substituted or unsubstituted divalent dibenzofuranyl group, a substituted or unsubstituted divalent carbazolyl group, or a substituted or unsubstituted divalent benzothienopyrimidinyl group.

In one embodiment of the present specification, L1 and L2 are the same as or different from each other, and each independently is a direct bond, a phenylene group that is unsubstituted or is substituted with an alkyl group or an aryl group, a biphenylene group, a divalent fluorenyl group that is unsubstituted or is substituted with an alkyl group or an aryl group, a divalent naphthalene group, a divalent spiro[fluorene-9,9'-xanthen]yl group, a divalent dibenzo-furanyl group, a divalent carbazolyl group, or a divalent benzothienopyrimidinyl group.

In one embodiment of the present specification, L1 and L2 are the same as or different from each other, and each independently is a direct bond, a phenylene group that is unsubstituted or is substituted with a methyl group or a phenyl group, a biphenylene group, a divalent 9,9'-dimethylfluorenyl group, a divalent 9,9'-diphenylfluorenyl group, a divalent spiro[fluorene-9,9'-xanthen]yl group, a divalent dibenzofuranyl group, a divalent carbazolyl group, or a divalent benzothienopyrimidinyl group.

According to one embodiment of the present specification, R1 to R3 are the same as or different from each other, and each independently is a $C_{1-10}$ linear or branched alkyl group.

According to one embodiment of the present specification, R1 to R3 are the same as or different from each other, and each independently is a $C_{1-6}$ linear or branched alkyl group.

According to one embodiment of the present specification, R1 to R3 are the same as or different from each other, and each independently is a $C_{1-4}$ linear or branched alkyl group.

According to one embodiment of the present specification, R1 to R3 are the same as or different from each other, and each independently is a linear alkyl group.

According to one embodiment of the present specification, R1 to R3 are the same as or different from each other, and each independently is a $C_{1-6}$ linear alkyl group.

According to one embodiment of the present specification, R1 to R3 are the same as or different from each other, and each independently is a $C_{1-4}$ linear alkyl group.

According to one embodiment of the present specification, R1 to R3 are a methyl group, an ethyl group, or a propyl group.

According to one embodiment of the present specification, Ar1 is a substituted or unsubstituted phenyl group, a substituted or unsubstituted $C_{10-30}$ aryl group, a substituted or unsubstituted $C_{2-5}$ monocyclic heteroaryl group, or a substituted or unsubstituted $C_{2-30}$ polycyclic heteroaryl group.

According to one embodiment of the present specification, Ar1 is a substituted or unsubstituted phenyl group, a substituted or unsubstituted $C_{10-25}$ aryl group, a substituted or unsubstituted $C_{2-5}$ monocyclic heteroaryl group, or a substituted or unsubstituted $C_{2-25}$ polycyclic heteroaryl group.

According to one embodiment of the present specification, Ar1 is a substituted or unsubstituted phenyl group, a substituted or unsubstituted $C_{10-20}$ aryl group, a substituted or unsubstituted $C_{2-5}$ monocyclic heteroaryl group, or a substituted or unsubstituted $C_{2-20}$ polycyclic heteroaryl group.

According to one embodiment of the present specification, Ar1 is a monocyclic aryl group that is unsubstituted or is substituted with a cyano group, an alkyl group, an arylphosphine oxide group, an aryl group or a heteroaryl group, a polycyclic aryl group, a monocyclic heteroaryl group that is unsubstituted or is substituted with an alkyl group or an aryl group, or a polycyclic heteroaryl group that is unsubstituted or is substituted with an aryl group.

According to one embodiment of the present specification, Ar1 is a substituted or unsubstituted phenyl group, a substituted or unsubstituted biphenyl group, a substituted or unsubstituted naphthalenyl group, a substituted or unsubstituted phenanthrenyl group, a substituted or unsubstituted triphenylenyl group, a substituted or unsubstituted fluorenyl group, a substituted or unsubstituted pyridinyl group, a substituted or unsubstituted pyrimidinyl group, a substituted or unsubstituted quinolinyl group, a substituted or unsubstituted benzimidazolyl group, a substituted or unsubstituted benzothiazolyl group, a substituted or unsubstituted benzoxazolyl group, a substituted or unsubstituted carbazolyl group, a substituted or unsubstituted phenanthrolinyl group, a substituted or unsubstituted indenocarbazolyl group, a substituted or unsubstituted dibenzofuranyl group, a substituted or unsubstituted dibenzothiophenyl group, a substituted or unsubstituted benzothienopyrimidinyl group, a substituted or unsubstituted diphenylphosphoryl group, or a substituted or unsubstituted spiro[fluorene-9,9'-xanthen]yl group.

According to one embodiment of the present specification, Ar1 is a phenyl group that is unsubstituted or is substituted with a cyano group, an alkyl group, an aryl group or a heteroaryl group, a biphenyl group that is unsubstituted or is substituted with a cyano group or an arylphosphine oxide group, a terphenyl group, a naphthyl group, a phenanthrenyl group, a triphenylenyl group, a pyridinyl group, a pyrimidinyl group that is unsubstituted or is substituted with an alkyl group or an aryl group, a quinolinyl group, a benzoxazolyl group, a benzothiazolyl group, a dibenzothiophenyl group, a dibenzofuranyl group, or a benzimidazolyl group that is unsubstituted or is substituted with an aryl group.

According to one embodiment of the present specification, Ar1 is a phenyl group that is unsubstituted or is substituted with a cyano group, a methyl group, a naphthyl group, a pyridinyl group or a carbazolyl group, a biphenyl group that is unsubstituted or is substituted with a cyano group or a diphenylphosphine oxide group, a terphenyl group, a naphthyl group, a phenanthrenyl group, a triphenylenyl group, a pyridinyl group, a pyrimidinyl group that is unsubstituted or is substituted with a methyl group or a phenyl group, a quinolinyl group, a benzoxazolyl group, a benzothiazolyl group, a dibenzothiophenyl group, a dibenzo-furanyl group, or a benzimidazolyl group that is unsubstituted or is substituted with a phenyl group.

According to one embodiment of the present specification, Ar1 is a monocyclic or polycyclic aryl group that is unsubstituted or is substituted with R11, or a monocyclic or polycyclic heteroaryl group that is unsubstituted or is substituted with R12.

According to one embodiment of the present specification, R11 is one substituent selected from the group consisting of a halogen group, a cyano group, an alkyl group, a haloalkyl group, an alkoxy group, a haloalkoxy group, an aryl group, a heteroaryl group, and —P(=O)(R21)(R22), or a substituent linking two or more substituents selected form the group, and R21 and R22 are the same as or different from each other and each independently is hydrogen, deuterium, an alkyl group, an aryl group, or a heteroaryl group.

According to one embodiment of the present specification, R12 is one substituent selected from the group consisting of a halogen group, a cyano group, an alkyl group, a haloalkyl group, an alkoxy group, a haloalkoxy group, an aryl group, a heteroaryl group, and —P(=O)(R23)(R24), or a substituent linking two or more substituents selected form the group, and R23 and R24 are the same as or different from each other and each independently is hydrogen, deuterium, an alkyl group, an aryl group, or a heteroaryl group.

According to one embodiment of the present specification, Ar1 is a phenyl group, a 3,5-diphenylphenyl group, a 3,5-dinaphthylphenyl group, a 3-methylphenyl group, a 4-cyanophenyl group, a 4-(1-phenyl-1H-benz[d]imidazol-2-yl)phenyl group, a 4-(benz[d]oxazol-2-yl)phenyl group, a 3,5-di(9H-carbazol-9-yl)phenyl group, a 4-diphenylphosphorylphenyl group, a 3-phenyl-5-(1,1'-biphenyl-4-yl)phenyl group, a 4-(dibenzo[b,d]furan-2-yl)phenyl group, a 3-(dibenzo[b,d]-thiophen-2-yl)-5-phenylphenyl group, a 3-(2-cyanospiro-[fluorene-9,9'-xanthen]-7-yl)phenyl group, a 4-trifluoromethoxyphenyl group, a 3,5-di(4-trifluoromethoxyphenyl)-phenyl group, a 4-trifluoromethylphenyl group, a 3-(triphenylen-2-yl)phenyl group, a 3-(9,9'-dimethyl-fluoren-2-yl)phenyl group, a 7-cyano-9,9'-diphenylfluoren-7-yl group, a 4-(4-phenylbenzo[4,5]thieno[3,2-d]pyrimidin-2-yl)-phenyl group, a 1,1'-biphenyl-4-yl group, a 4'-cyano(1,1'-biphenyl)-4-yl group, a 4'-(1-phenyl-1H-benz[d]imidazol-2-yl)-[1,1'-biphenyl]-3-yl group, a 4'-diphenylphorphoryl-1,1'-biphenyl-4-yl group, a 4'-trifluoromethyl(1,1'-biphenyl)-4-yl group, a naphthalen-2-yl group, a 2-(4-cyanophenyl)naphthalen-1-yl group, a 4-(benzo[d]thiazol-2-yl)naphthalen-1-yl group, a phenanthren-9-yl group, a triphenylen-2-yl group, a 9,9'-dimethylfluoren-2-yl group, a pyridin-2-yl group, a 5-methylpyridin-2-yl group, a 2,5,6-trimethylpyrimidin-4-yl group, a 2,5-dimethyl-6-phenyl-pyrimidin-4-yl group, a quinolin-8-yl group, a 1-phenyl-1H-benz[d]imidazol-2-yl group, a benzo[d]thiazol-2-yl group, a benz[d]oxazol-2-yl group, a 9H-carbazol-9-yl group, a 9-phenyl-9H-carbazol-3-yl group, a 3-(9-phenyl-9H-carbazol-3-yl)-9-phenyl-9H-carbazol-3-yl group, a 6-(dibenzo[b,d]-thiophen-2-yl)-9-phenyl-9H-carbazol-3-yl group, a 1,10-phenanthrolin-5-yl group, a 11,12-dimethyl-11,12-dihydroindene[2,1-a]carbazol-11-yl group, a dibenzo[b,d]furan-2-yl group, a 6-(4,5,6-trimethyl-pyrimidin-2-yl)-dibenzo[b,d]furan-3-yl group, a 7-(4,5,6-trimethylpyrimidin-2-yl)dibenzo[b,d]furan-2-yl group, a dibenzo[b,d]thiophen-2-yl group, a 4-phenylbenzo[4,5]-thieno[3,2-d]pyrimidin-2-yl group, a diphenylphosphoryl group, a spiro[fluorene-9,9'-xanthen]-7-yl group, a 2-cyano-spiro[fluorene-9,9'-xanthen]-7-yl group, or a 2-(4-cyanophenyl)spiro[fluorene-9,9'-xanthen]-7-yl group.

According to one embodiment of the present specification, the compound of Chemical Formula 1 is selected from among the following compounds:

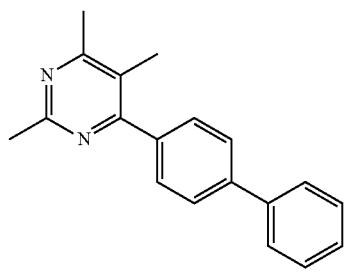

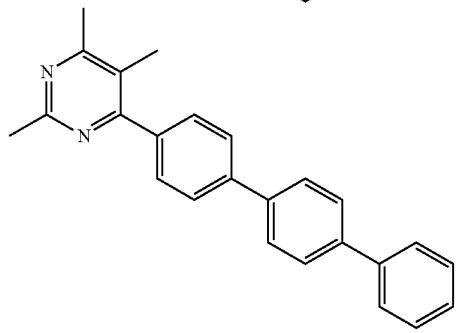

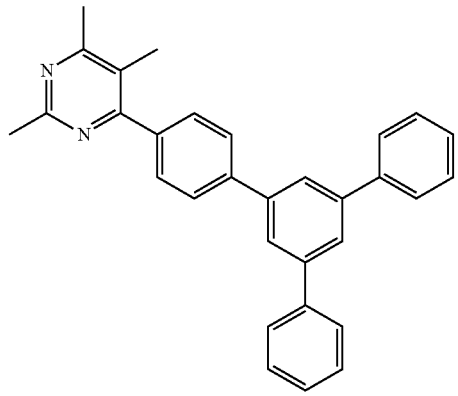

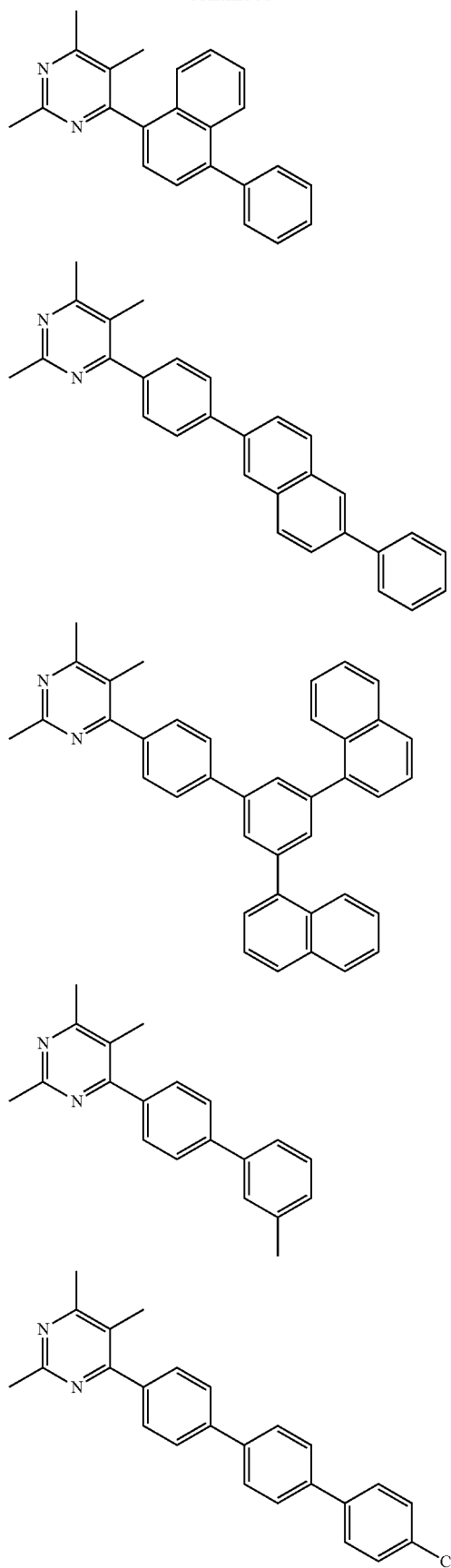
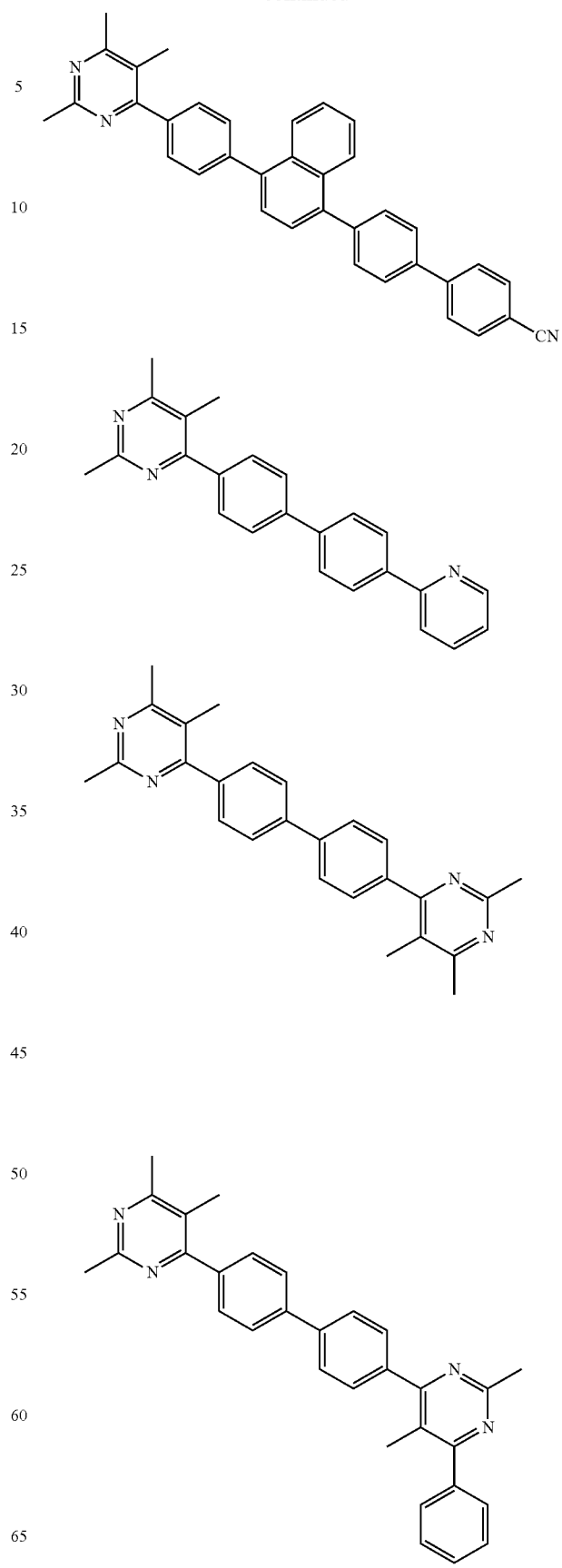

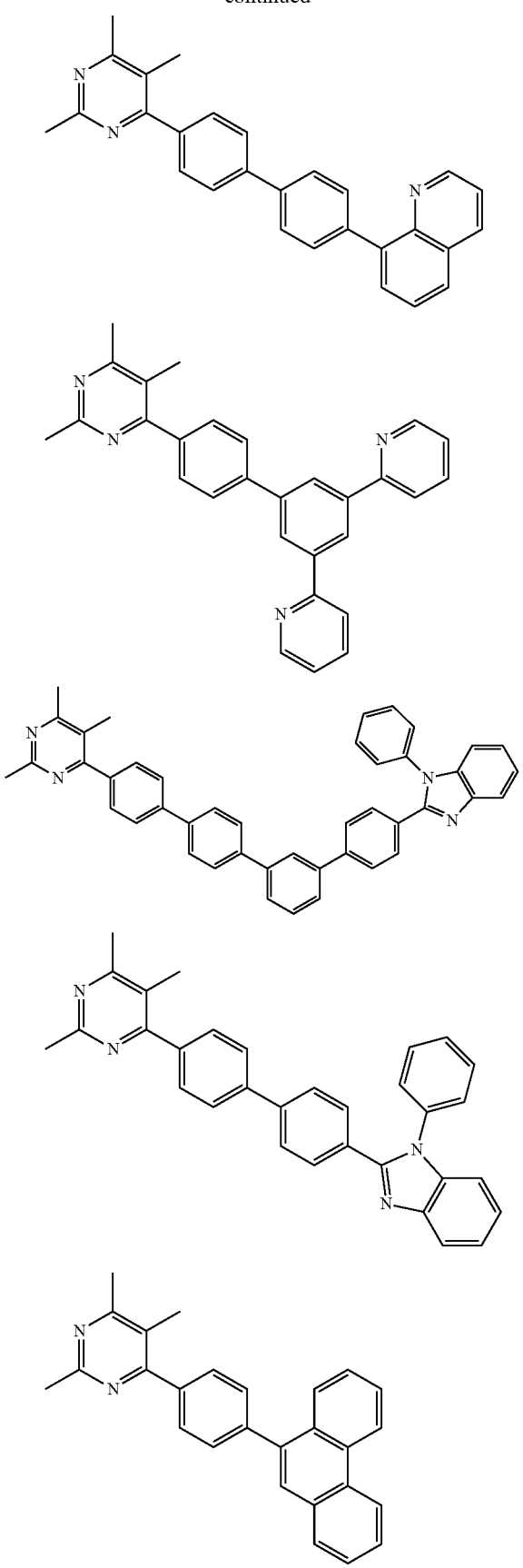

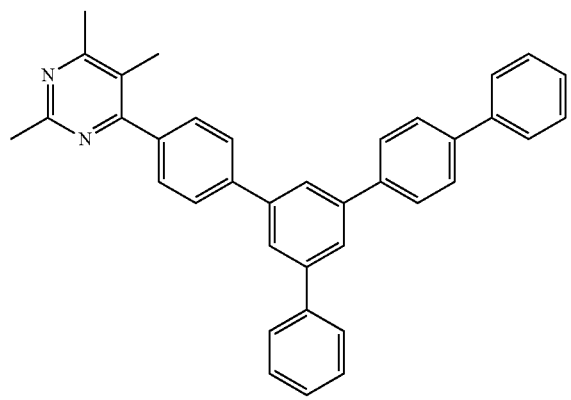
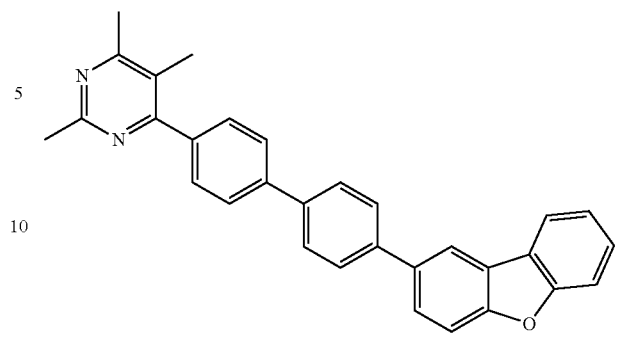
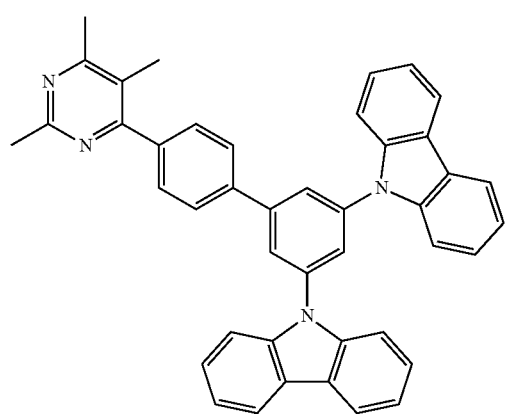
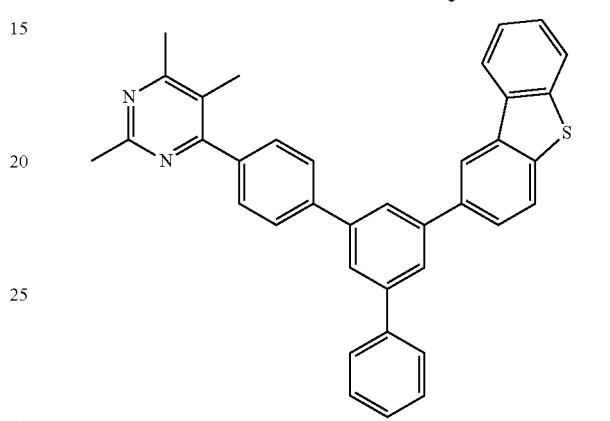
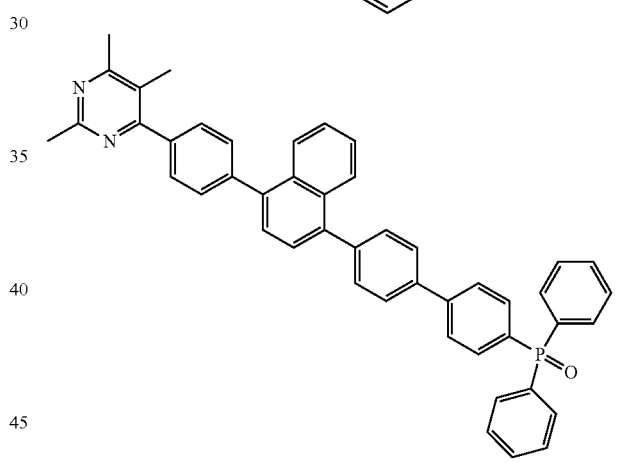
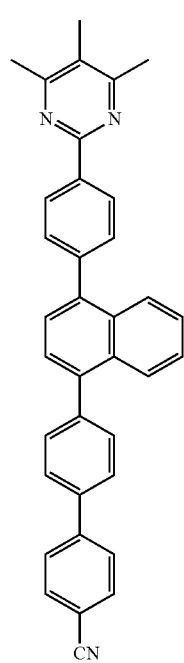
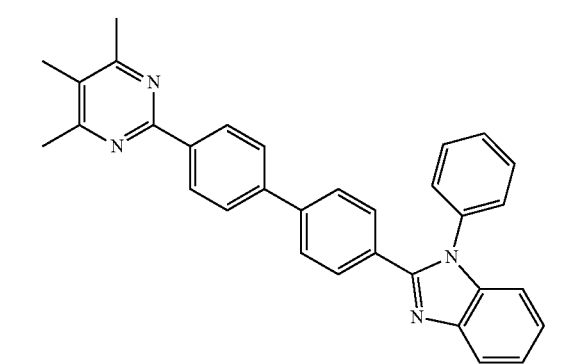

19
-continued
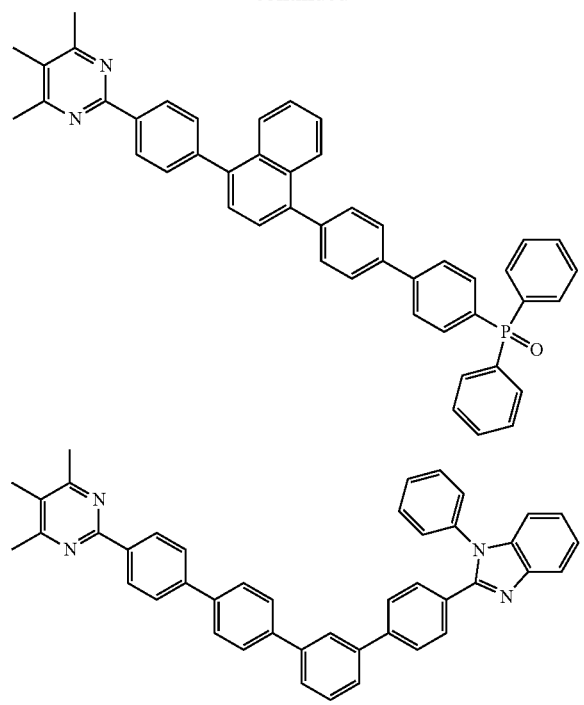
20
-continued
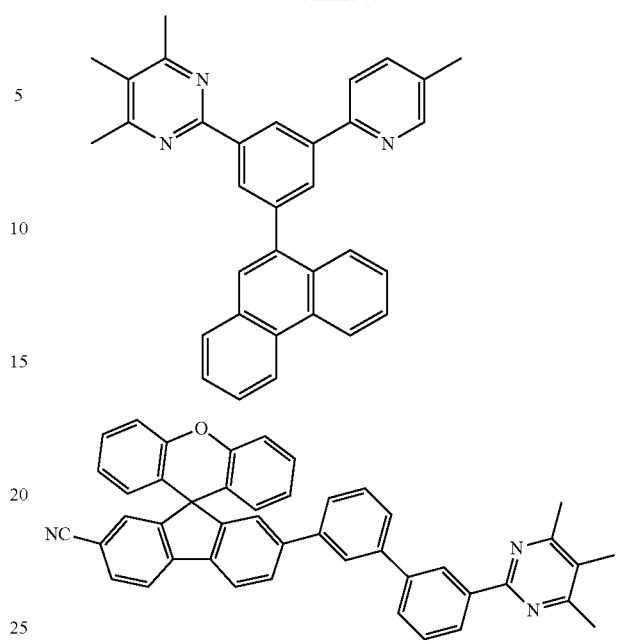
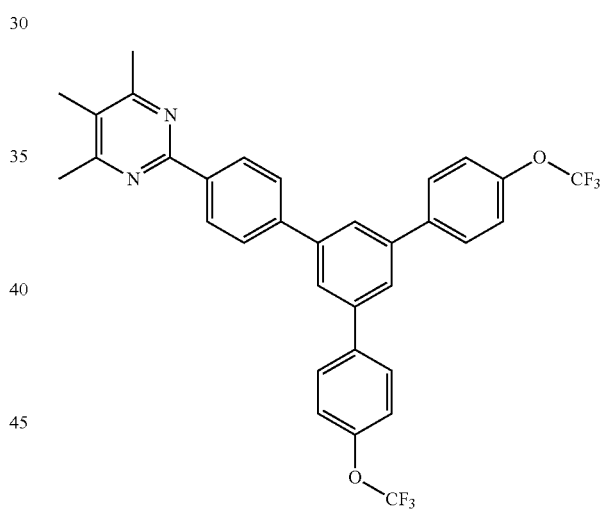
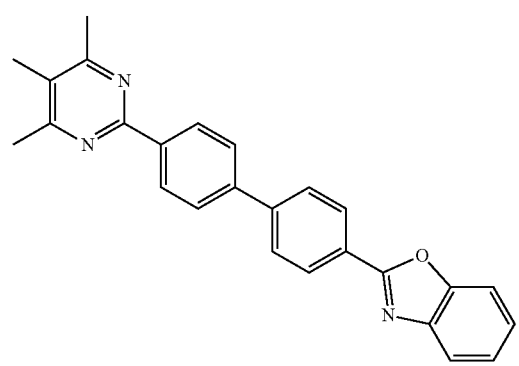
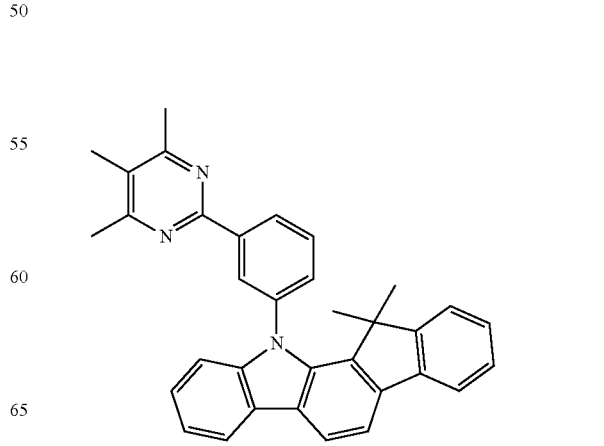

21
-continued
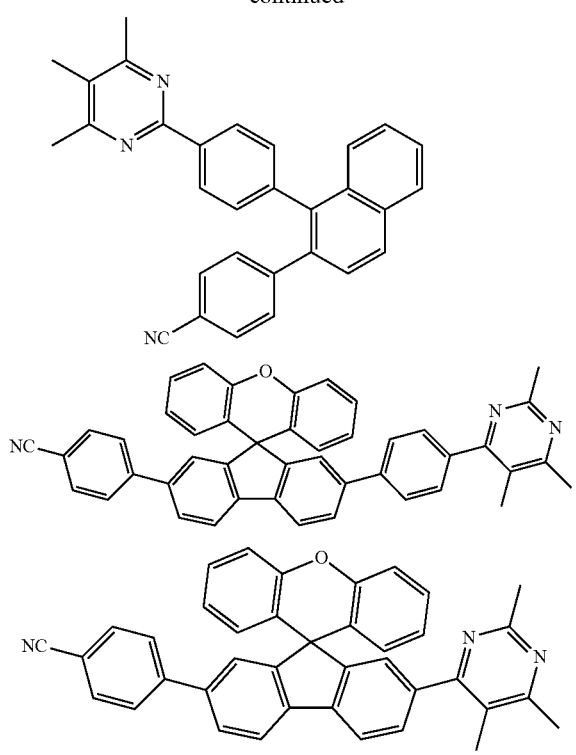
22
-continued
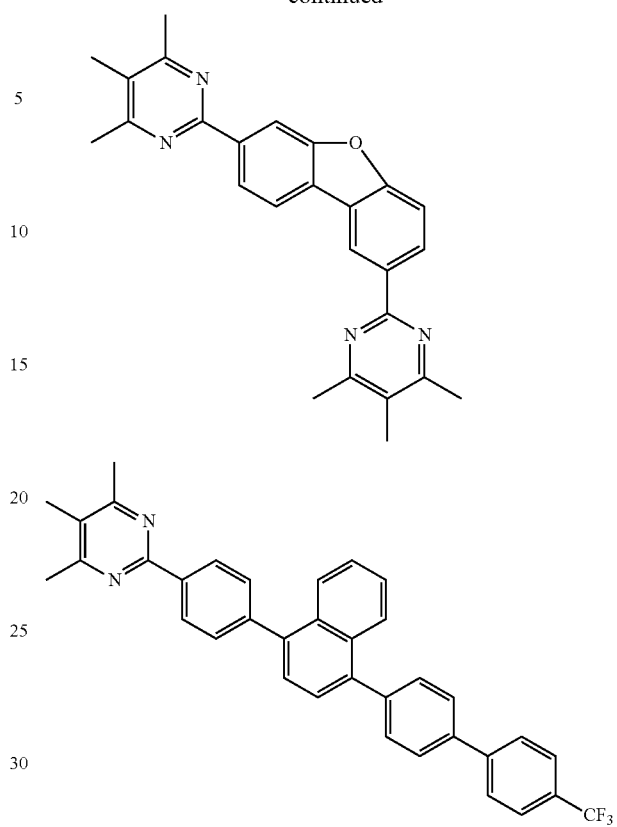
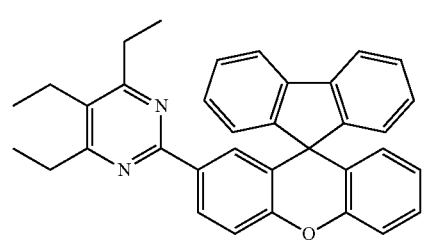
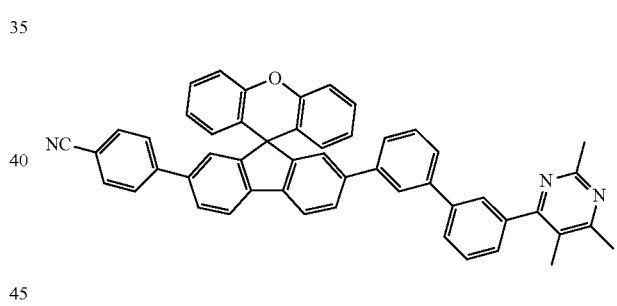
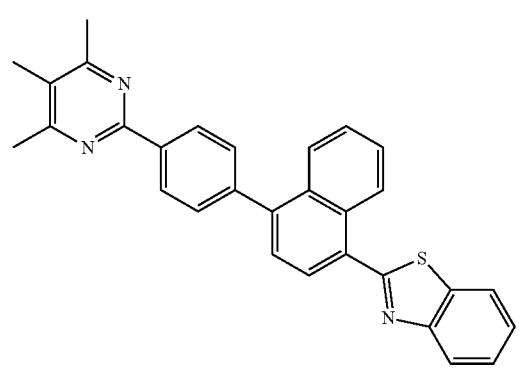
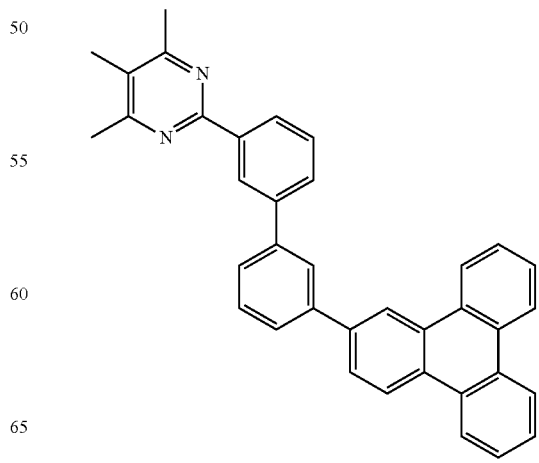

23
-continued
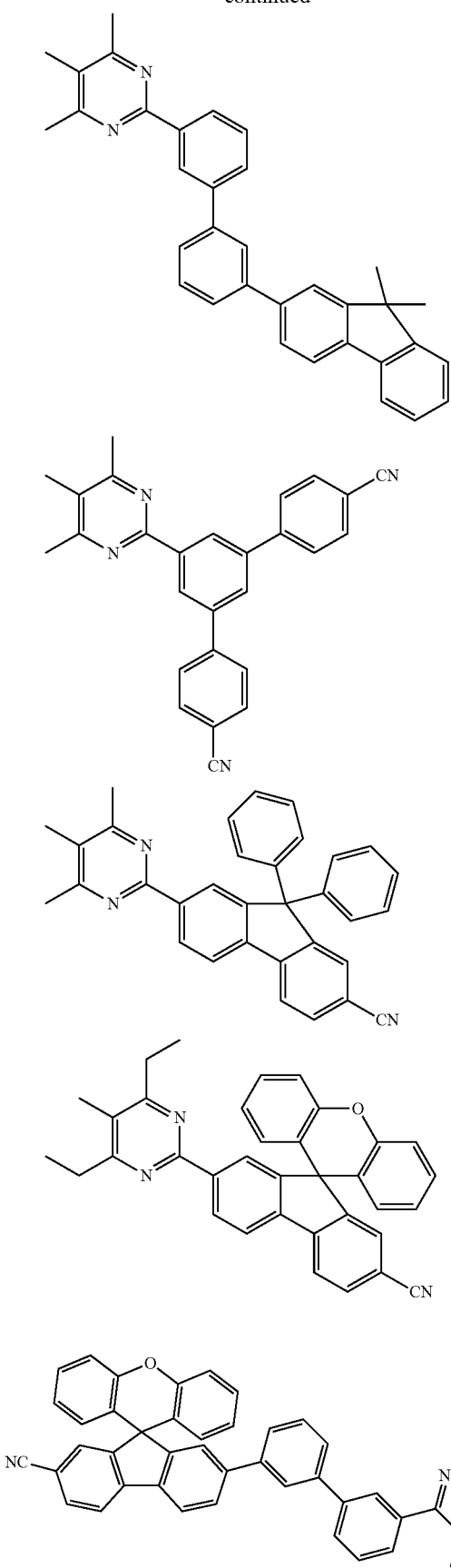
24
-continued
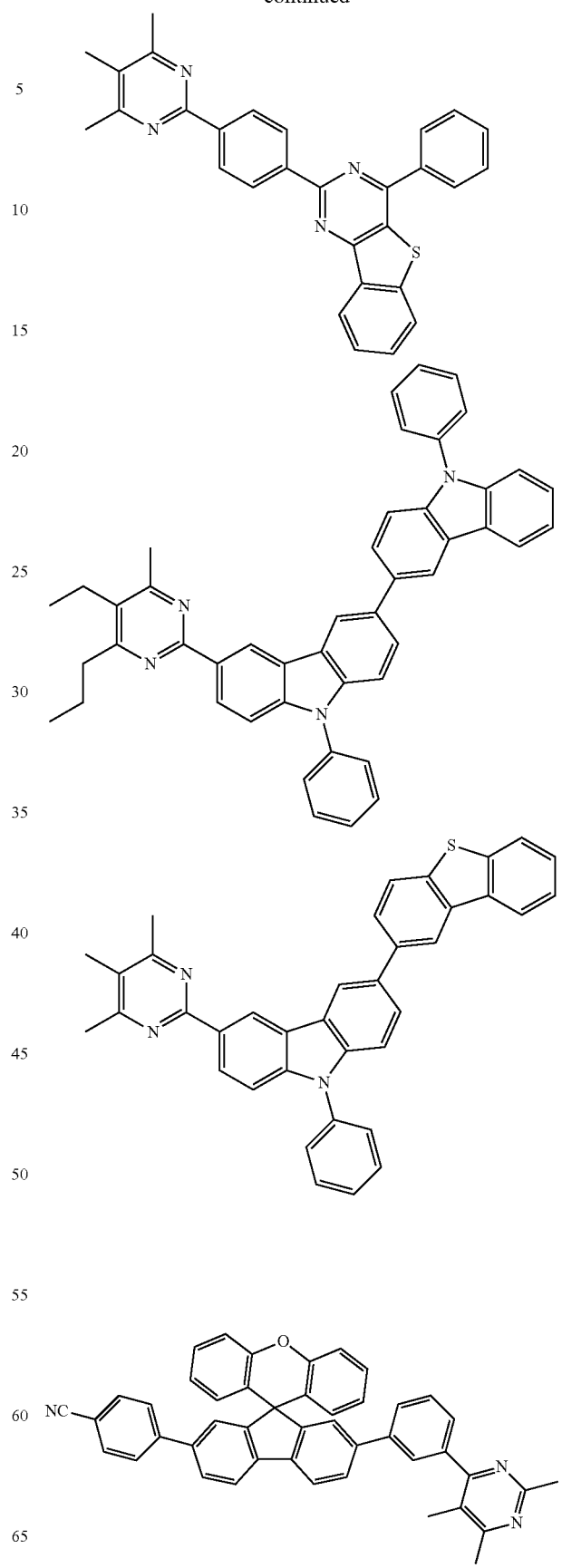

-continued
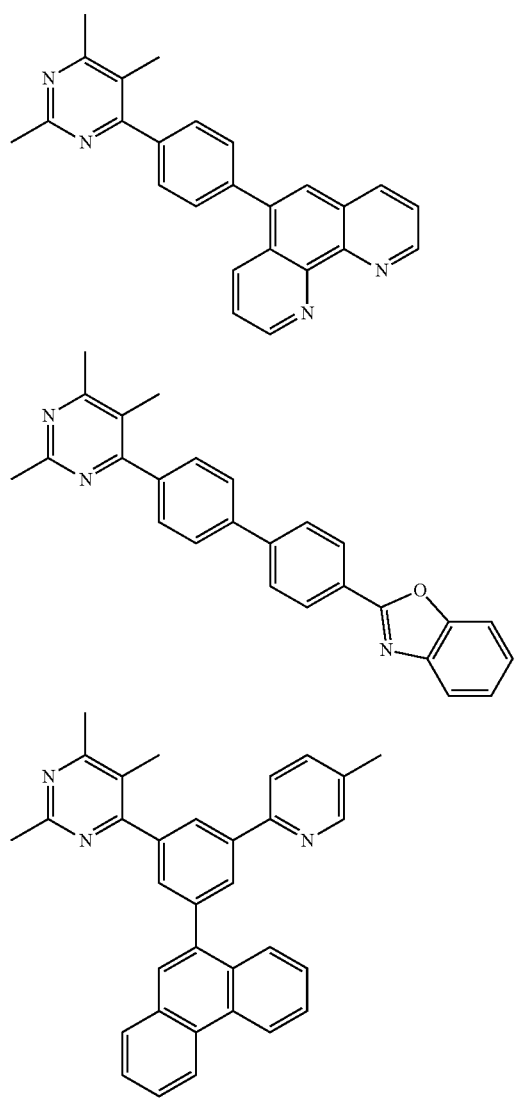
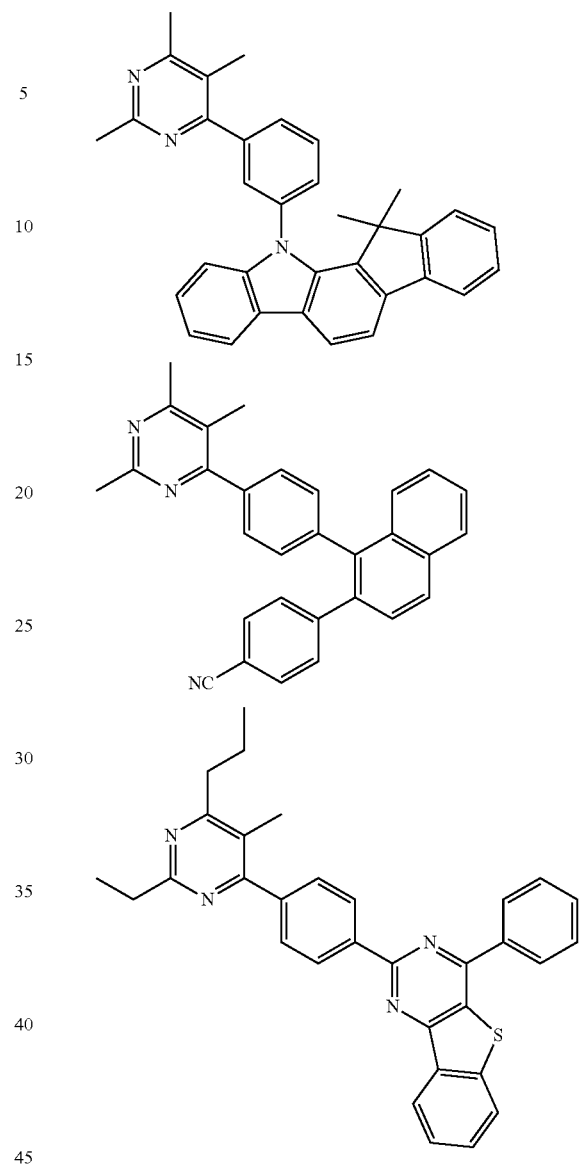

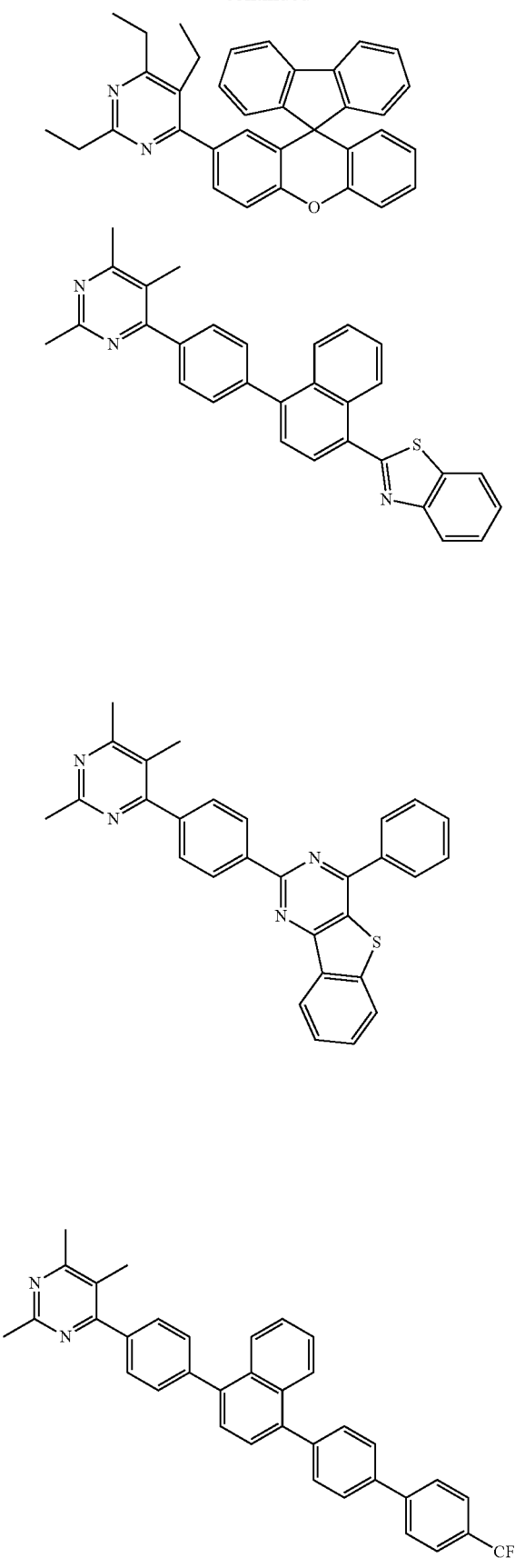
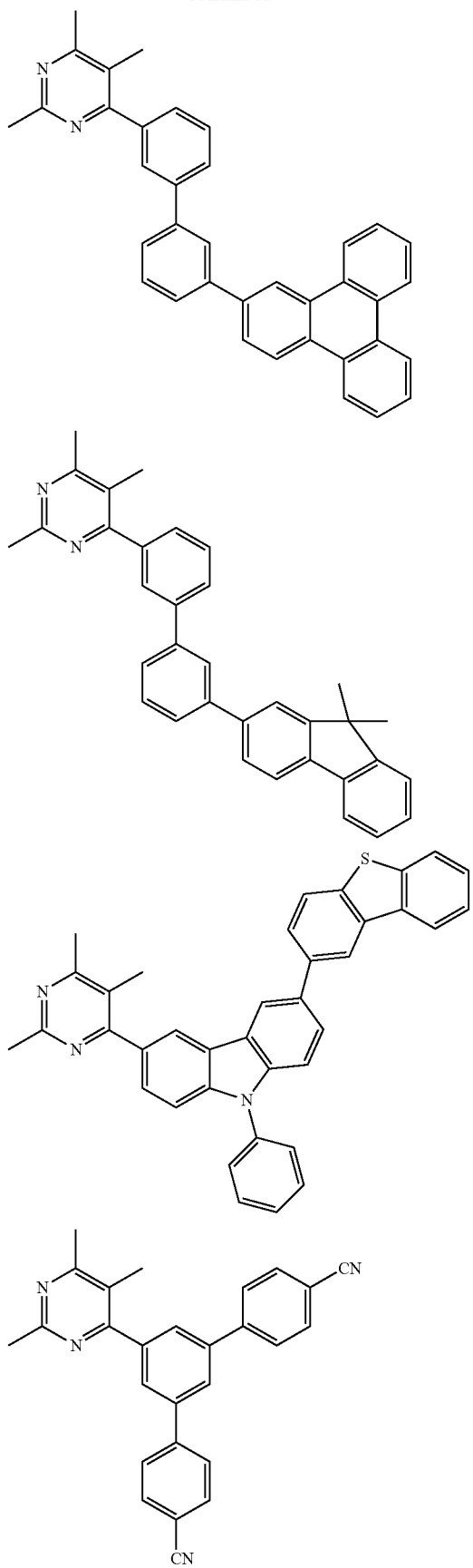

-continued

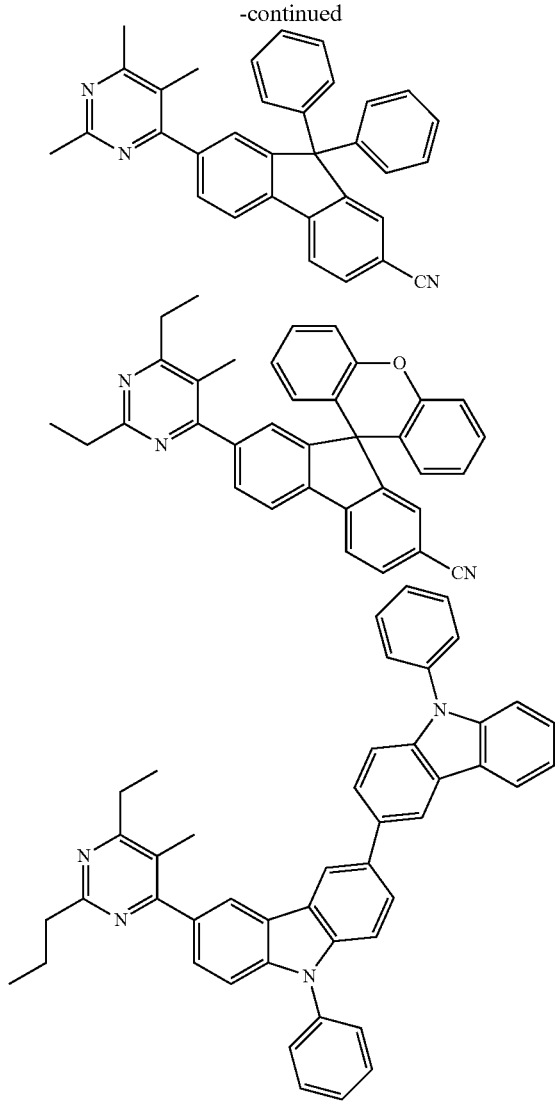

One embodiment of the present specification provides an organic light emitting device comprising the compound of Chemical Formula 1 described above.

According to one embodiment of the present specification, the organic light emitting device comprises a first electrode; a second electrode provided opposite to the first electrode; and one or more organic material layers provided between the first electrode and the second electrode, wherein one or more layers of the organic material layers comprise the compound of Chemical Formula 1.

The organic material layer of the organic light emitting device of the present specification can be formed in a single layer structure, but can also be formed in a multilayer structure in which two or more organic material layers are laminated. For example, the organic light emitting device of the present disclosure can have a structure comprising a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can further comprise various organic material layers known in the art.

Figure 8:
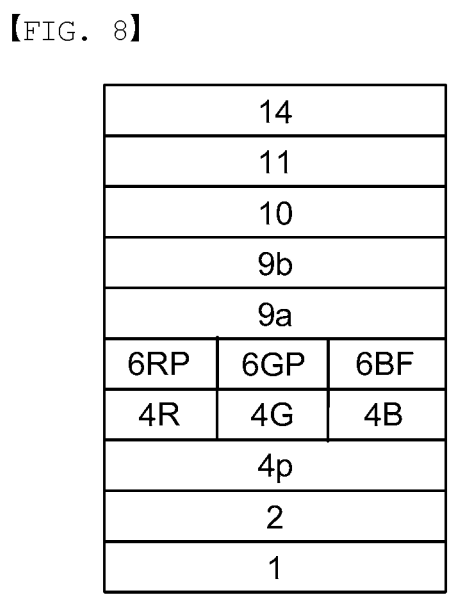

For example, the organic light emitting device of the present specification can have structures as illustrated in FIG. 1, FIG. 2 and FIG. 8, however, the structure is not limited thereto.

FIG. 1 illustrates a structure of the organic light emitting device in which a substrate (1), an anode (2), a hole injection layer (3), a hole transfer layer (4), a light emitting layer (6), a hole blocking layer (7), an electron injection and transfer layer (8) and a cathode (11) are consecutively laminated. In such a structure, the compound of Chemical Formula 1 can be included in the electron injection and transfer layer (8).

FIG. 2 illustrates a structure of the organic light emitting device in which a substrate (1), an anode (2), a hole injection layer (3), a hole transfer layer (4), an electron blocking layer (5), a light emitting layer (6), an electron injection and transfer layer (8) and a cathode (11) are consecutively laminated. In such a structure, the compound of Chemical Formula 1 can be included in the electron injection and transfer layer (8).

FIG. 8 illustrates a structure of the organic light emitting device in which a substrate (1), an anode (2), a p-doped hole transfer layer (4p), a hole transfer layer (4R, 4G, 4B), a light emitting layer (6RP, 6GP, 6BF), a first electron transfer layer (9a), a second electron transfer layer (9b), an electron injection layer (10), a cathode (11) and a capping layer (14) are consecutively laminated. In such a structure, the compound of Chemical Formula 1 can be included in one or more of the first electron transfer layer (9a) and the second electron transfer layer (9b).

According to one embodiment of the present specification, the organic light emitting device can have a tandem structure in which two or more independent devices are connected in series. In one embodiment, the tandem structure can have a form in which each organic light emitting device are connected by a charge generating layer. A device having a tandem structure can be driven at a lower current than a unit device based on the same brightness, and therefore, there is an advantage in that device lifetime properties are greatly enhanced.

According to one embodiment of the present specification, the organic material layer comprises a first stack comprising one or more light emitting layers; a second stack comprising one or more light emitting layers; and one or more charge generating layers provided between the first stack and the second stack.

According to another embodiment of the present specification, the organic material layer comprises a first stack comprising one or more light emitting layers; a second stack comprising one or more light emitting layers; and a third stack comprising one or more light emitting layers, and comprises one or more charge generating layers provided between each of the first stack and the second stack; and the second stack and the third stack.

In the present specification, the charge generating layer can mean a layer in which holes and electrons are generated when applying a voltage. The charge generating layer can be an N-type charge generating layer or a P-type charge generating layer. In the present specification, the N-type charge generating layer means a charge generating layer locating closer to an anode than the P-type charge generating layer, and the P-type charge generating layer means a charge generating layer locating closer to a cathode than the N-type charge generating layer.

The N-type charge generating layer and the P-type charge generating layer can be provided in contact with each other, and in this case, an NP junction is formed. By the NP junction, holes are readily formed in the P-type charge generating layer, and electrons are readily formed in the N-type charge generating layer. The electrons are transferred toward an anode through a LUMO level of the N-type charge generating layer, and the holes are transferred toward a cathode through a HOMO level of the P-type charge generating layer.

The first stack, the second stack and the third stack each independently comprise one or more light emitting layers, and can further comprise one or more of a hole injection layer, a hole transfer layer, an electron blocking layer, an electron injection layer, an electron transfer layer, a hole blocking layer, a layer carrying out hole transfer and hole injection at the same time (hole injection and transfer layer), and a layer carrying out electron transfer and electron injection at the same time (electron injection and transfer layer).

The organic light emitting device including the first stack and the second stack is illustrated in FIG. 3.

FIG. 3 illustrates a structure of the organic light emitting device in which a substrate (1), an anode (2), a hole injection layer (3), a first hole transfer layer (4a), an electron blocking layer (5), a first light emitting layer (6a), a first electron transfer layer (9a), an N-type charge generating layer (12), a P-type charge generating layer (13), a second hole transfer layer (4b), a second light emitting layer (6b), an electron injection and transfer layer (8) and a cathode (11) are consecutively laminated. In such a structure, the compound of Chemical Formula 1 can be included in the electron injection and transfer layer (8).

The organic light emitting device including the first stack to the third stack is illustrated in FIGS. 4 to 7.

FIG. 4 illustrates a structure of the organic light emitting device in which a substrate (1), an anode (2), a hole injection layer (3), a first hole transfer layer (4a), an electron blocking layer (5), a first light emitting layer (6a), a first electron transfer layer (9a), a first N-type charge generating layer (12a), a first P-type charge generating layer (13a), a second hole transfer layer (4b), a second light emitting layer (6b), a second electron transfer layer (9b), a second N-type charge generating layer (12b), a second P-type charge generating layer (13b), a third hole transfer layer (4c), a third light emitting layer (6c), a third electron transfer layer (9c) and a cathode (11) are consecutively laminated. In such a structure, the compound of Chemical Formula 1 can be included in one or more of the first electron transfer layer (9a), the second electron transfer layer (9b) and the third electron transfer layer (9c).

FIG. 5 illustrates a structure of the organic light emitting device in which a substrate (1), an anode (2), a hole injection layer (3), a first hole transfer layer (4a), a second hole transfer layer (4b), a first blue fluorescent light emitting layer (6BFa), a first electron transfer layer (9a), a first N-type charge generating layer (12a), a first P-type charge generating layer (13a), a third hole transfer layer (4c), a red phosphorescent light emitting layer (6RP), a yellow green phosphorescent light emitting layer (6YGP), a green phosphorescent light emitting layer (6GP), a second electron transfer layer (9b), a second N-type charge generating layer (12b), a second P-type charge generating layer (13b), a fourth hole transfer layer (4d), a fifth hole transfer layer (4e), a second blue fluorescent light emitting layer (6BFb), a third electron transfer layer (9c), an electron injection layer (10), a cathode (11) and a capping layer (14) are consecutively laminated. In such a structure, the compound of Chemical Formula 1 can be included in one or more of the third electron transfer layer (9c), the second electron transfer layer (9b) and the first electron transfer layer (9a).

FIG. 6 illustrates a structure of the organic light emitting device in which a substrate (1), an anode (2), a hole injection layer (3), a first hole transfer layer (4a), a second hole transfer layer (4b), a first blue fluorescent light emitting layer (6BFa), a first electron transfer layer (9a), a first N-type charge generating layer (12a), a first P-type charge generating layer (13a), a third hole transfer layer (4c), a red phosphorescent light emitting layer (6RP), a green phosphorescent light emitting layer (6GP), a second electron transfer layer (9b), a second N-type charge generating layer (12b), a second P-type charge generating layer (13b), a fourth hole transfer layer (4d), a fifth hole transfer layer (4e), a second blue fluorescent light emitting layer (6BFb), a third electron transfer layer (9c), an electron injection layer (10), a cathode (11) and a capping layer (14) are consecutively laminated. In such a structure, the compound of Chemical Formula 1 can be included in one or more of the third electron transfer layer (9c), the second electron transfer layer (9b) and the first electron transfer layer (9a).

FIG. 7 illustrates a structure of the organic light emitting device in which a substrate (1), an anode (2), a first p-doped hole transfer layer (4pa), a first hole transfer layer (4a), a second hole transfer layer (4b), a first blue fluorescent light emitting layer (6BFa), a first electron transfer layer (9a), a first N-type charge generating layer (12a), a first P-type charge generating layer (13a), a third hole transfer layer (4c), a fourth hole transfer layer (4d), a second blue fluorescent light emitting layer (6BFb), a second electron transfer layer (9b), a second N-type charge generating layer (12b), a second P-type charge generating layer (13b), a fifth hole transfer layer (4e), a sixth hole transfer layer (4f), a third blue fluorescent light emitting layer (6BFc), a third electron transfer layer (9c), an electron injection layer (10), a cathode (11) and a capping layer (14) are consecutively laminated. In such a structure, the compound of Chemical Formula 1 can be included in one or more of the first electron transfer layer (9a), the second electron transfer layer (9b), and the third electron transfer layer (9c).

The N-type charge generating layer can be 2,3,5,6-tetrafluoro-7,7,8,8-tetracyanoquinodimethane (F4TCNQ), fluorine-substituted 3,4,9,10-perylenetetracarboxylic dianhydride (PTCDA), cyano-substituted PTCDA, naphthalenetetracarboxylic dianhydride (NTCDA), fluorine-substituted NTCDA, cyano-substituted NTCDA, a hexaazatriphenylene derivative and the like, but is not limited thereto. In one embodiment, the N-type charge generating layer can include both a benzimidazophenanthridine-based derivative and a Li metal.

The P-type charge generating layer can include both an arylamine-based derivative and a compound including a cyano group.

According to one embodiment of the present specification, the organic material layer comprises an electron transfer layer; an electron injection layer; or a layer carrying out electron transfer and electron injection at the same time, and the electron transfer layer; the electron injection layer; or the layer carrying out electron transfer and electron injection at the same time comprises the compound.

According to one embodiment of the present specification, the organic material layer comprises a hole blocking layer, and the hole blocking layer comprises the compound.

According to one embodiment of the present specification, the organic material layer comprises a hole injection layer, a hole transfer layer, or a layer carrying out hole transfer and hole injection at the same time, and the hole injection layer, the hole transfer layer, or the layer carrying out hole transfer and hole injection at the same time comprises the compound.

According to one embodiment of the present specification, the organic material layer comprises a light emitting layer, and the light emitting layer comprises the compound.

According to one embodiment of the present specification, the organic material layer includes one or more layers selected from the group consisting of a hole injection layer, a hole transfer layer, an electron injection layer, an electron transfer layer, an electron blocking layer, a hole blocking layer, a layer carrying out hole transfer and hole injection at the same time, and a layer carrying out electron transfer and electron injection at the same time.

According to one embodiment of the present specification, the organic material layer comprises a light emitting layer, the light emitting layer comprises a host and a dopant, and the dopant has a maximum light emission wavelength of 400 nm to 520 nm.

According to another embodiment, the dopant of the light emitting layer is a blue fluorescent dopant.

According to one embodiment of the present specification, the organic material layer comprises two or more light emitting layers, and at least one of the two or more light emitting layers comprises a blue fluorescent dopant.

According to another embodiment, at least two of the two or more light emitting layers have a different maximum light emission wavelength.

In another embodiment, at least one of the two or more light emitting layers comprises a phosphorescent dopant, and at least one of the remaining layers comprises a fluorescent dopant.

When the organic light emitting device comprises two or more light emitting layers, each of the light emitting layers can be vertically laminated as illustrated in FIGS. 4 to 7, or each of the light emitting layers can be horizontally laminated as illustrated in FIG. 8.

According to one embodiment of the present specification, the organic material layer further comprises, in addition to the organic material layer comprising the compound of Chemical Formula 1, a hole injection layer or a hole transfer layer comprising a compound comprising an arylamino group, a carbazole group or a benzocarbazole group.

The organic light emitting device of the present specification can be manufactured using materials and methods known in the art, except that one or more layers of the organic material layers comprise the compound of the present specification, that is, the compound of Chemical Formula 1.

When the organic light emitting device comprises a plurality of organic material layers, the organic material layers can be formed with the same material or with different materials.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as a sputtering method or an e-beam evaporation method, forming an organic material layer including a hole injection layer, a hole transfer layer, a light emitting layer and an electron transfer layer thereon, and then depositing a material usable as a second electrode thereon. In addition to such a method, the organic light emitting device can be manufactured by consecutively depositing a second electrode material, an organic material layer and a first electrode material on a substrate. In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such methods, the organic light emitting device can also be manufactured by consecutively depositing a cathode material, an organic material layer and an anode material on a substrate. However, the manufacturing method is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxy-benzoquinoline-metal compounds; benzoxazole-, benzothiazole- and benzimidazole-based compounds; poly (p-phenylenevinylene) (PPV)-based polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

In one embodiment of the present specification, an anthracene derivative unsubstituted or substituted with deuterium can be used as a host of the light emitting layer. In one embodiment, a lifetime is enhanced when an anthracene derivative is deuterated, which has an advantage of being usable as a host material in more diverse device structures.

According to one embodiment of the present specification, the host can be a compound of the following Chemical Formula H1 or H2, but is not limited thereto. When including the following compound, an energy level between the organic material layer and the light emitting layer is properly controlled, and quantities of electrons migrating from the organic material layer to the light emitting layer are readily controlled, which is effective in improving a lifetime of an organic light emitting device.

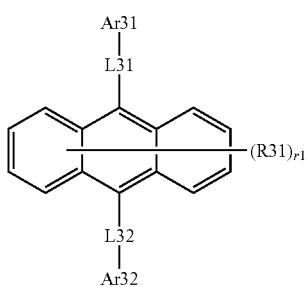

Chemical Formula H1

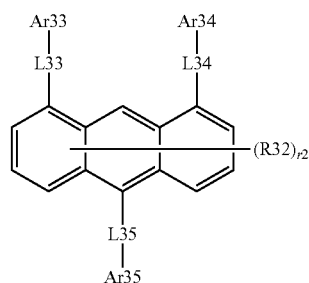

Chemical Formula H2

In Chemical Formulae H1 and H2:

L31 to L35 are the same as or different from each other, and each independently is a direct bond, a substituted or unsubstituted arylene group, or a substituted or unsubstituted heteroarylene group;

Ar31 to Ar35 are the same as or different from each other, and each independently is a substituted or unsubstituted aryl group, or a substituted or unsubstituted heteroaryl group;

R31 and R32 are the same as or different from each other, and each independently is hydrogen, or a substituted or unsubstituted aryl group;

r1 is an integer of 1 to 8;

r2 is an integer of 1 to 7;

when r1 is 2 or greater, the R31s are the same as or different from each other; and when r2 is 2 or greater, the R32s are the same as or different from each other.

According to one embodiment of the present specification, L31 to L35 are the same as or different from each other, and each independently is a direct bond or an arylene group.

According to one embodiment of the present specification, L31 to L35 are the same as or different from each other, and each independently is a direct bond or a $C_{6-22}$ arylene group.

According to one embodiment of the present specification, L31 to L35 are the same as or different from each other, and each independently is a direct bond or a $C_{6-18}$ arylene group.

According to one embodiment of the present specification, L31 to L35 are the same as or different from each other, and each independently is a direct bond or a $C_{6-14}$ arylene group.

According to one embodiment of the present specification, L31 to L35 are the same as or different from each other, and each independently is a direct bond, a phenylene group, a divalent naphthyl group, or a divalent anthracenyl group.

According to one embodiment of the present specification, Ar31 to Ar35 are the same as or different from each other, and each independently is an aryl group that is unsubstituted or is substituted with deuterium, or a heteroaryl group that is unsubstituted or is substituted with an aryl group.

According to one embodiment of the present specification, Ar31 to Ar35 are the same as or different from each other, and each independently is a $C_{6-22}$ aryl group that is unsubstituted or is substituted with deuterium, or a $C_{2-24}$ heteroaryl group.-

According to one embodiment of the present specification, Ar31 to Ar35 are the same as or different from each other, and each independently is a $C_{6-18}$ aryl group that is unsubstituted or is substituted with deuterium, or a $C_{2-20}$ heteroaryl group.

According to one embodiment of the present specification, Ar31 to Ar35 are the same as or different from each other, and each independently is a $C_{6-14}$ aryl group that is unsubstituted or is substituted with deuterium, or a $C_{2-16}$ heteroaryl group.

According to one embodiment of the present specification, Ar31 to Ar35 are the same as or different from each other, and each independently is a phenyl group that is unsubstituted or is substituted with deuterium, a biphenyl group, a naphthyl group, a phenanthrenyl group, a thiophenyl group that is unsubstituted or is substituted with a phenyl group, a dibenzofuranyl group, a dibenzothiophenyl group, a benzo[b]naphtho[1,2-d]furanyl group, a benzo[b]naphtho[2,3-d]furanyl group, a benzo[d]-naphtho[1,2-b]furanyl group, a benzo[b]naphtho[2,1-d]thiophenyl group, a benzo[b]naphtho-[1,2-d]thiophenyl group, or a benzo[b]naphtho[2,3-d]-thiophenyl group.

According to one embodiment of the present specification, R31 is hydrogen or an aryl group that is unsubstituted or is substituted with an aryl group.

According to one embodiment of the present specification, R31 is hydrogen or a $C_{6-16}$ aryl group that is unsubstituted or is substituted with a $C_{6-16}$ aryl group.

According to one embodiment of the present specification, R31 is hydrogen or a $C_{6-12}$ aryl group that is unsubstituted or is substituted with a $C_{6-12}$ aryl group.

According to one embodiment of the present specification, R31 is hydrogen or a naphthyl group that is unsubstituted or is substituted with a phenyl group.

According to one embodiment of the present specification, R32 is hydrogen.

According to one embodiment of the present specification, the host is any one or more compounds selected from among the following compounds:

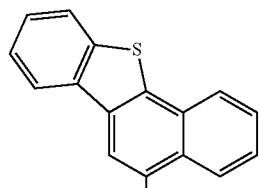

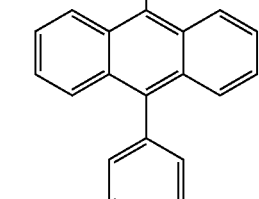

-continued

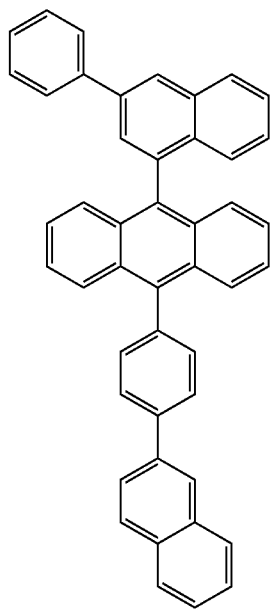

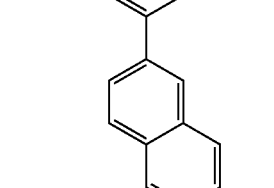

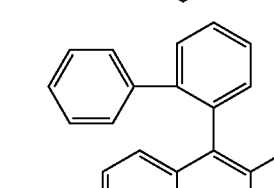

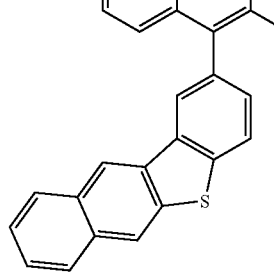

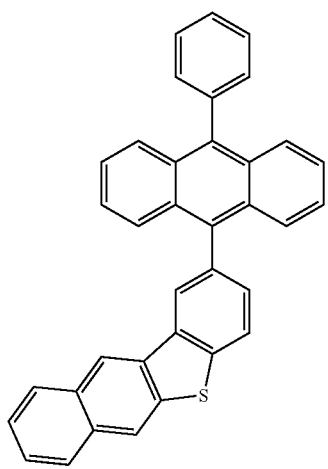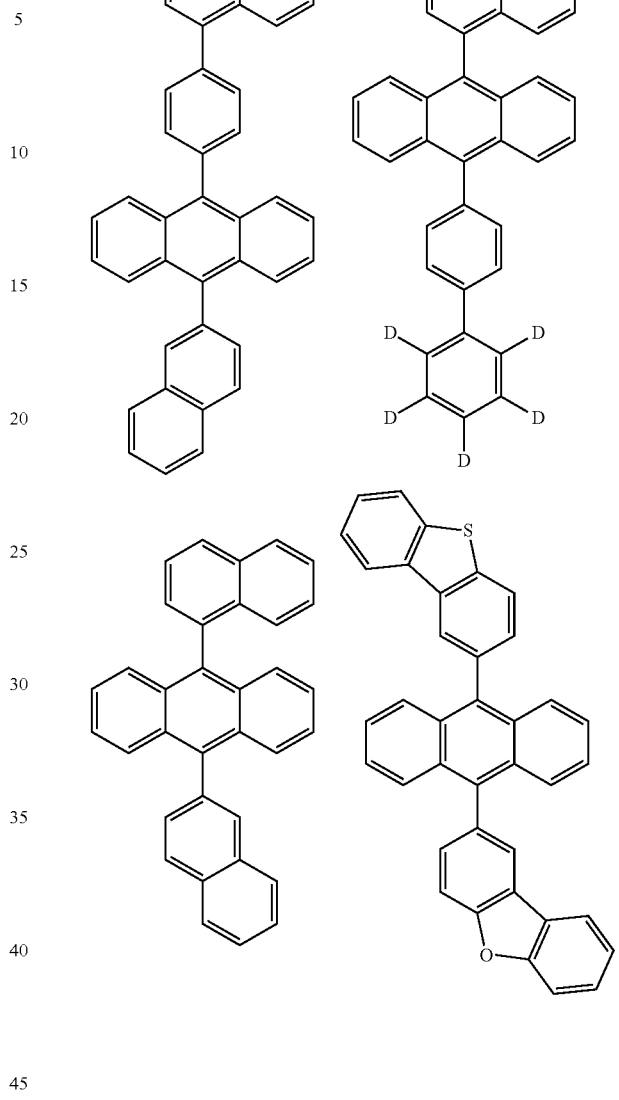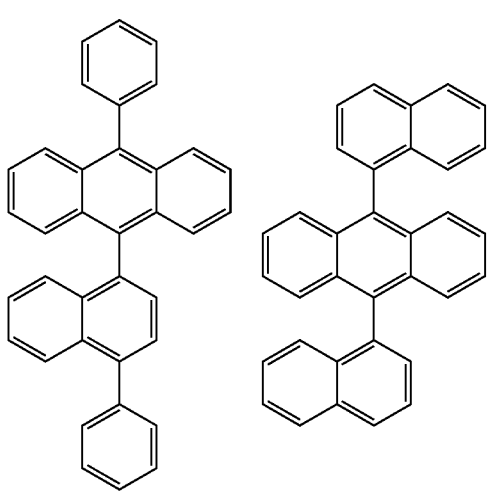

41
-continued
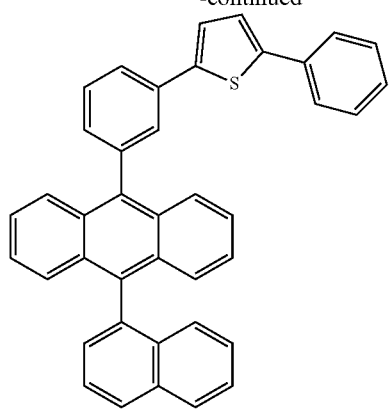
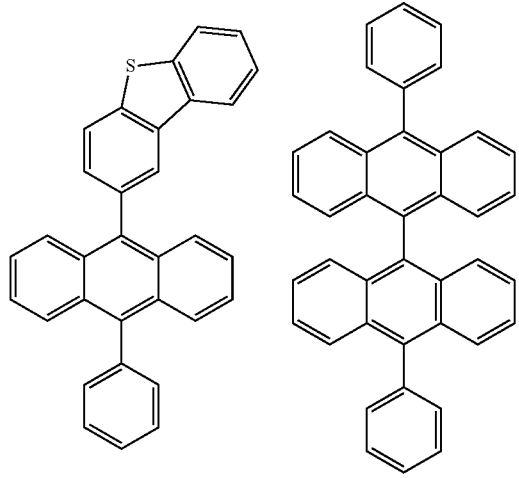
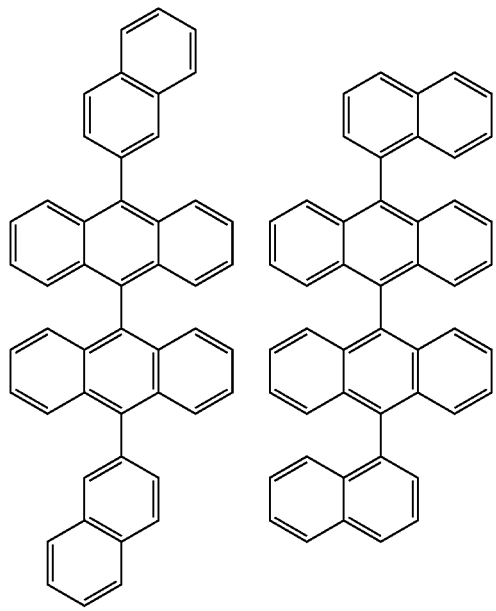
42
-continued
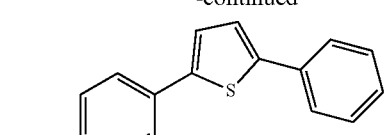
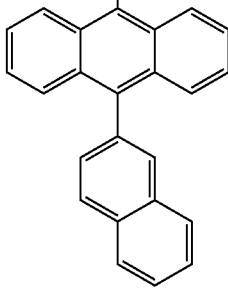
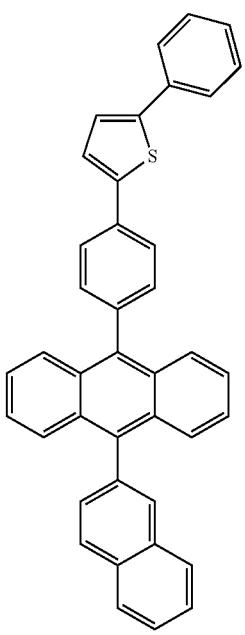
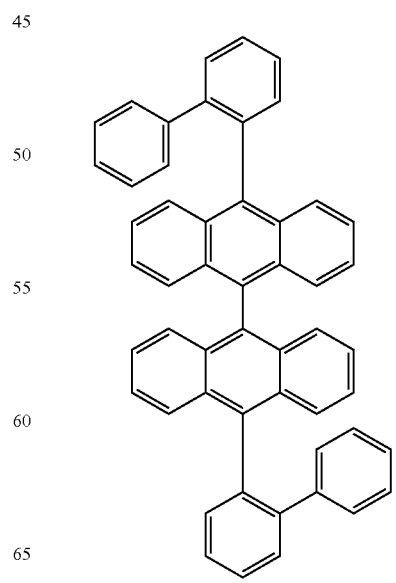

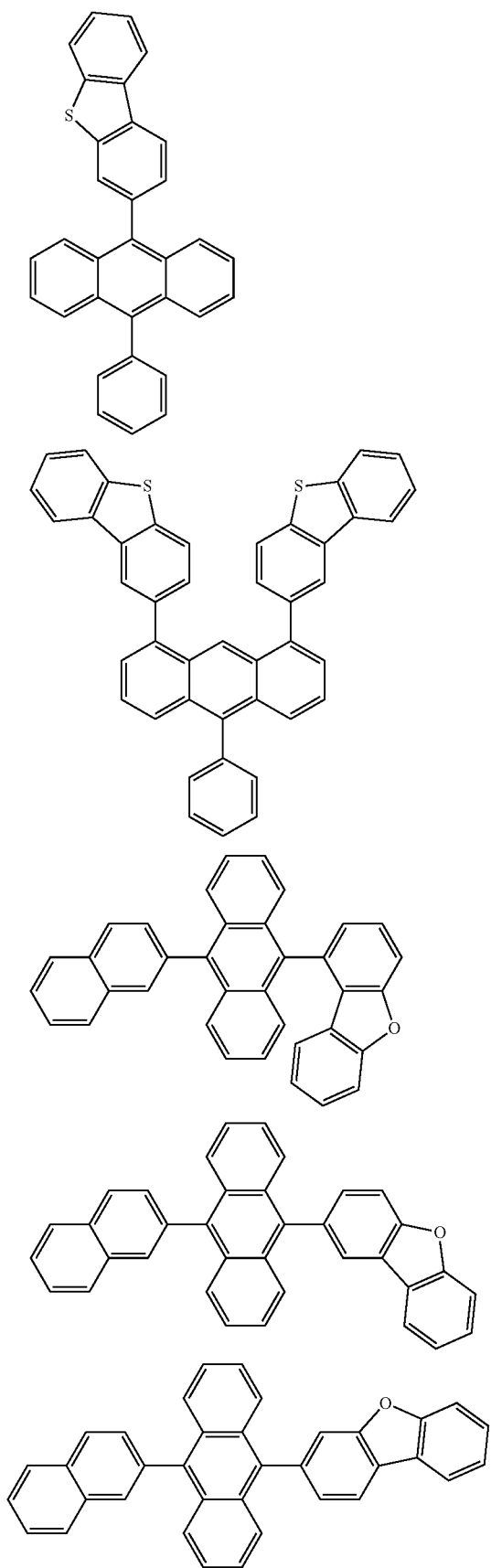
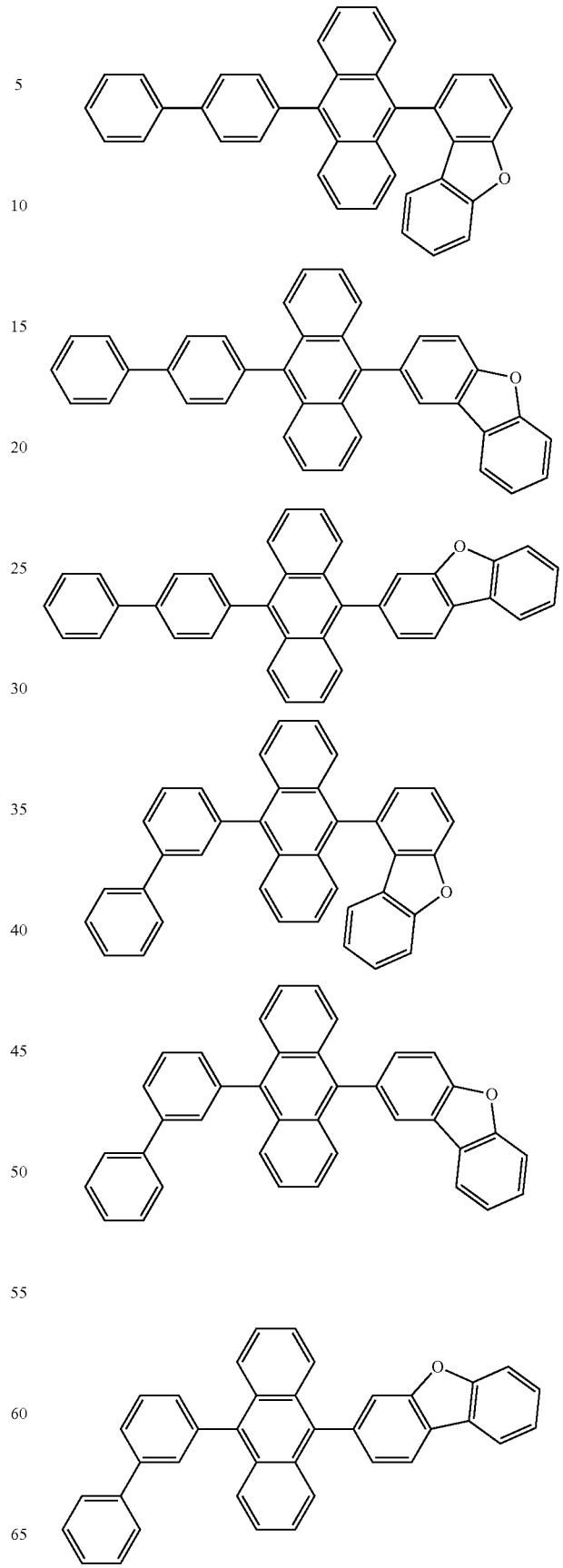

-continued
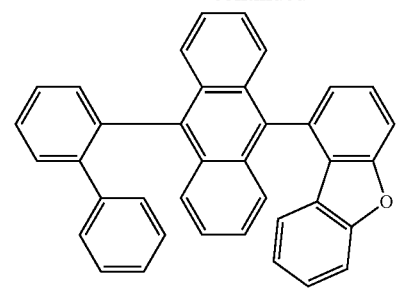
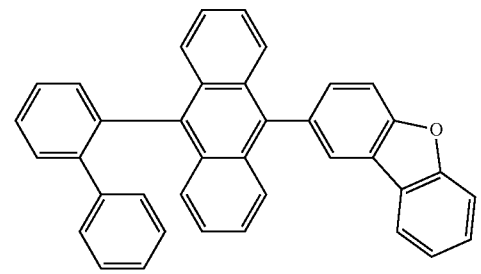
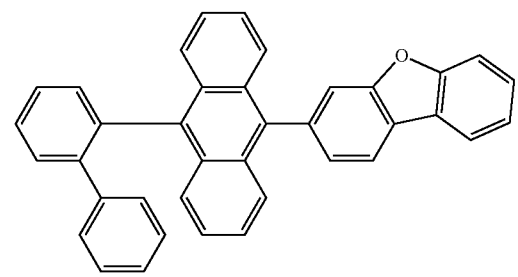
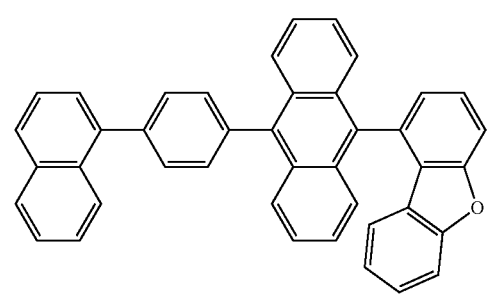
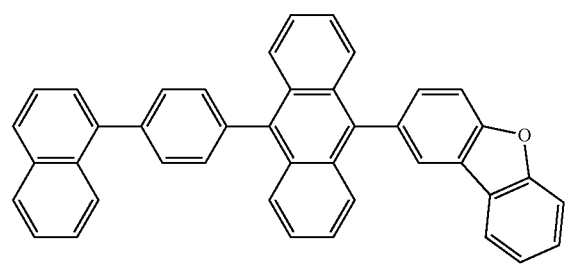
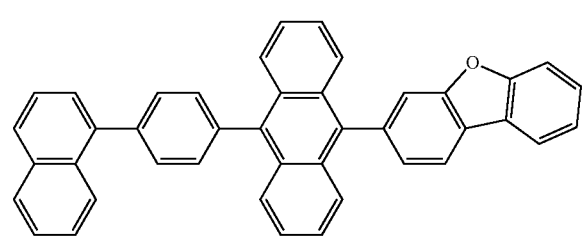
-continued
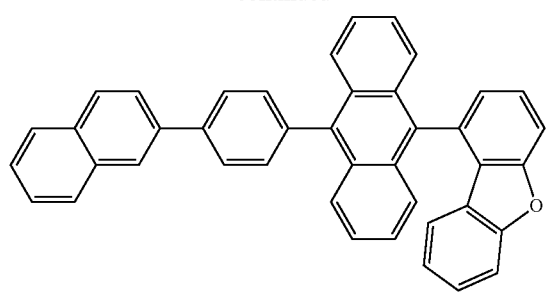
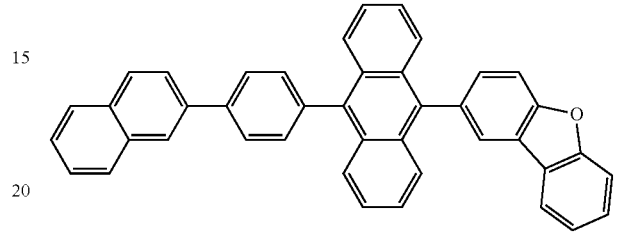
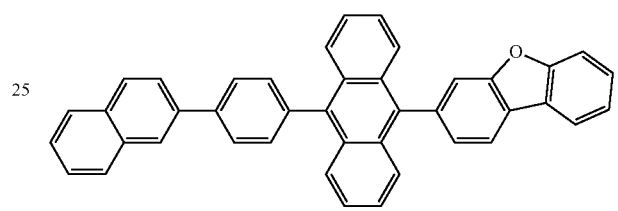
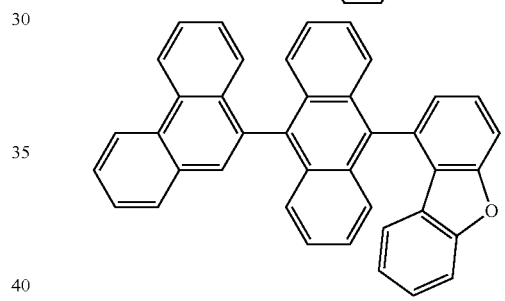
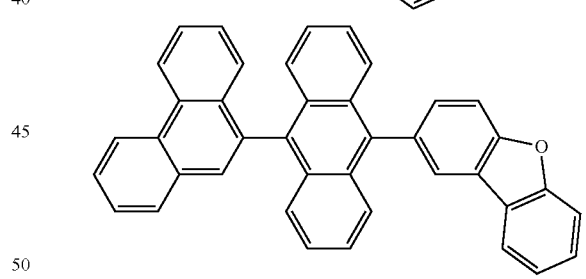
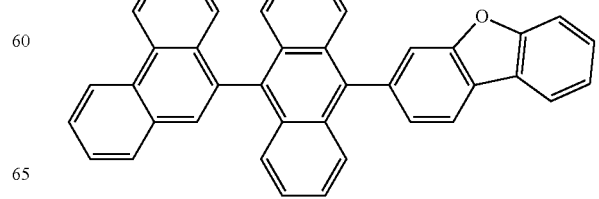

47
-continued
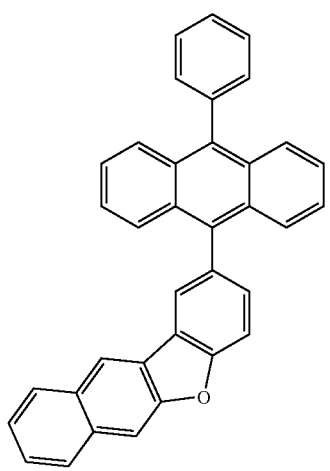
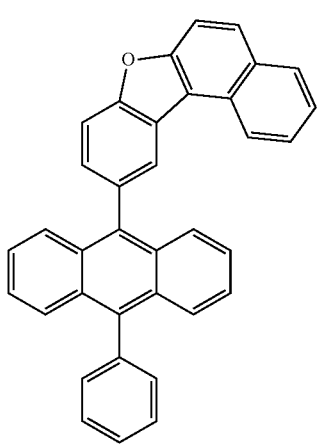
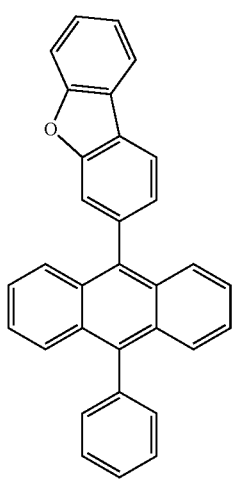
48
-continued
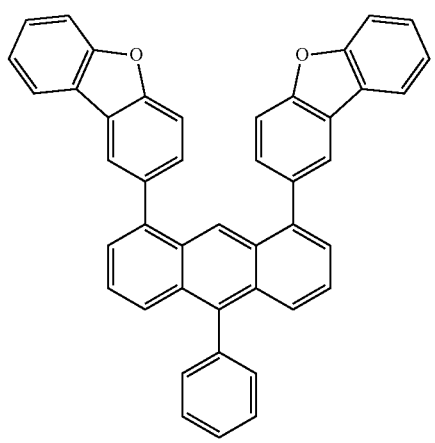
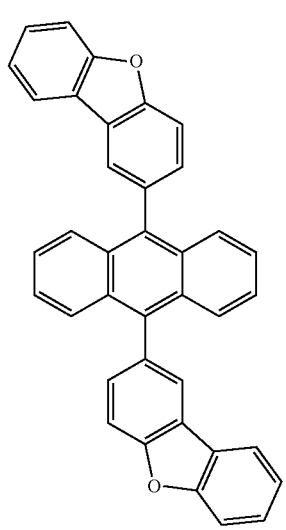
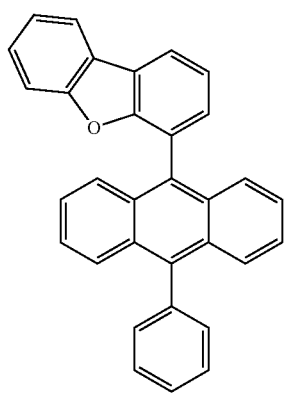

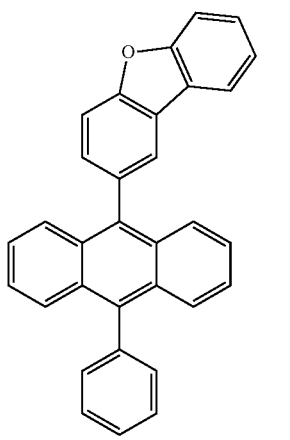
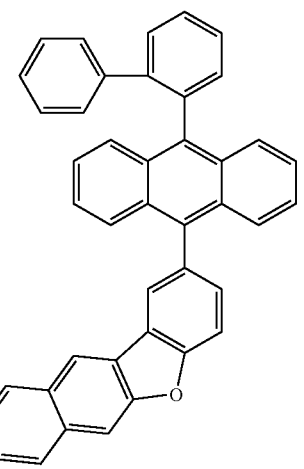
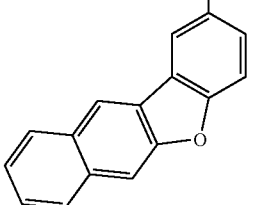
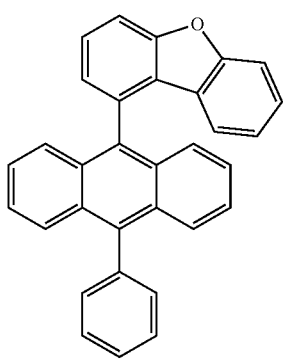
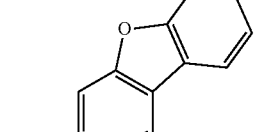
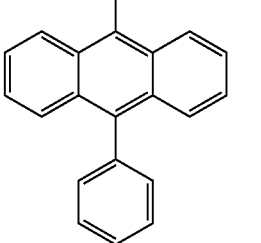
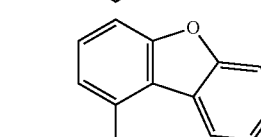
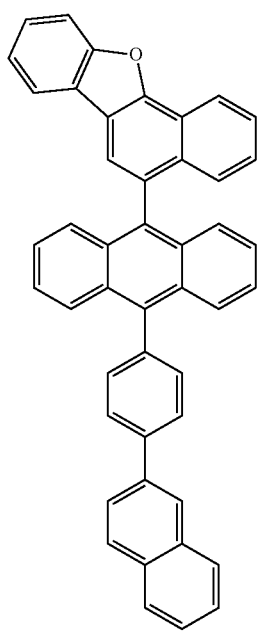
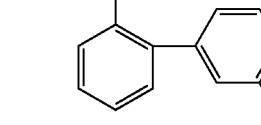
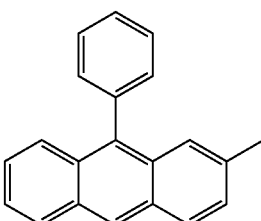
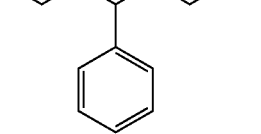

-continued

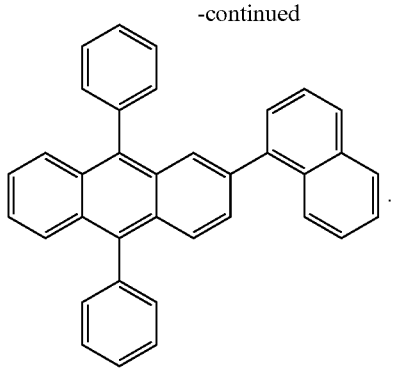

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and an arylamino group-including pyrene, anthracene, chrysene, peryflanthene and the like can be included. The styrylamine compound is a compound in which substituted or unsubstituted arylamine is substituted with at least one arylvinyl group, and compounds in which one, two or more substituents selected from the group consisting of an aryl group, a silyl group, an alkyl group, a cycloalkyl group and a substituted or unsubstituted arylamino group can be used. Specifically, styrylamine, styryldiamine, styryltriamine, styryltetramine and the like can be included, however, the styrylamine compound is not limited thereto. In addition, as the metal complex, iridium complexes, platinum complexes and the like can be included, however, the metal complex is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato)zinc, bis(2-methyl-8-quinolinato)-chlorogallium, bis(2-methyl-8-quinolinato)(o-cresolato)-gallium, bis(2-methyl-8-quinolinato)(1-naphtholato)aluminum, bis(2-methyl-8-quinolinato)(2-naphtholato) gallium and the like, but is not limited thereto.

The capping layer (14) can perform a role of preventing inflow of oxygen and moisture inflowing from the outside by covering an organic light emitting device, and enhancing efficiency of light passing through the cathode (11). The capping layer is a functional layer formed to be thin enough to have almost no optical effect, and the capping layer can be formed to have a thickness of 5 nm or less, and can be an insulating layer formed with an organic material or an inorganic material.

The organic light emitting device according to the present specification can be a top-emission type, a bottom-emission type or a dual-emission type depending on the materials used.

According to one embodiment of the present specification, the compound of Chemical Formula 1 can be included in an organic solar cell or an organic transistor in addition to an organic light emitting device.

<Synthesis Example 1> Preparation of Compound 1

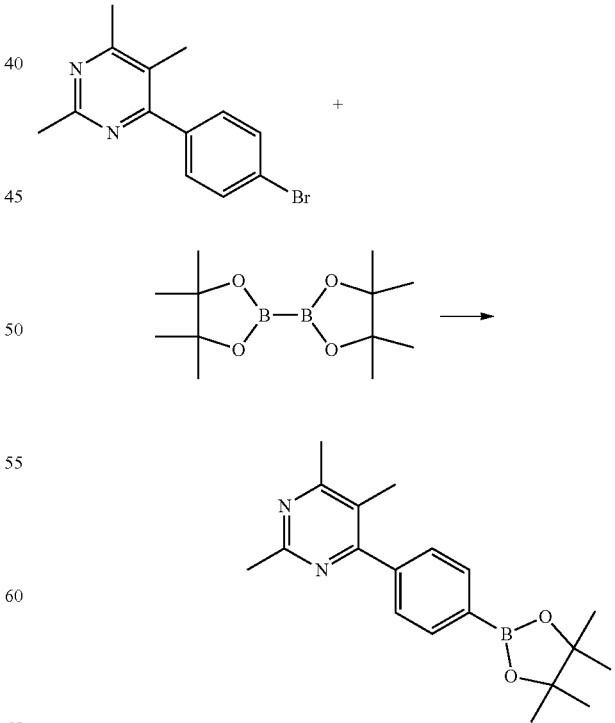

1A

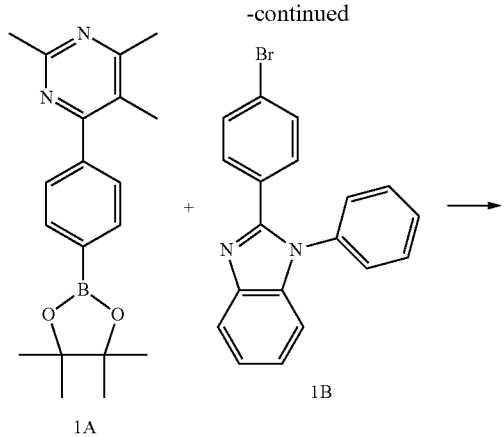

Magnesium sulfate (MgSO$_4$) was introduced to the organic layer, and the layer was filtered. The result was concentrated, and then purified using column chromatography to obtain Compound 1 (9 g, yield 77%).

MS: [M+H]$^+$=466

<Synthesis Example 2> Preparation of Compound 2

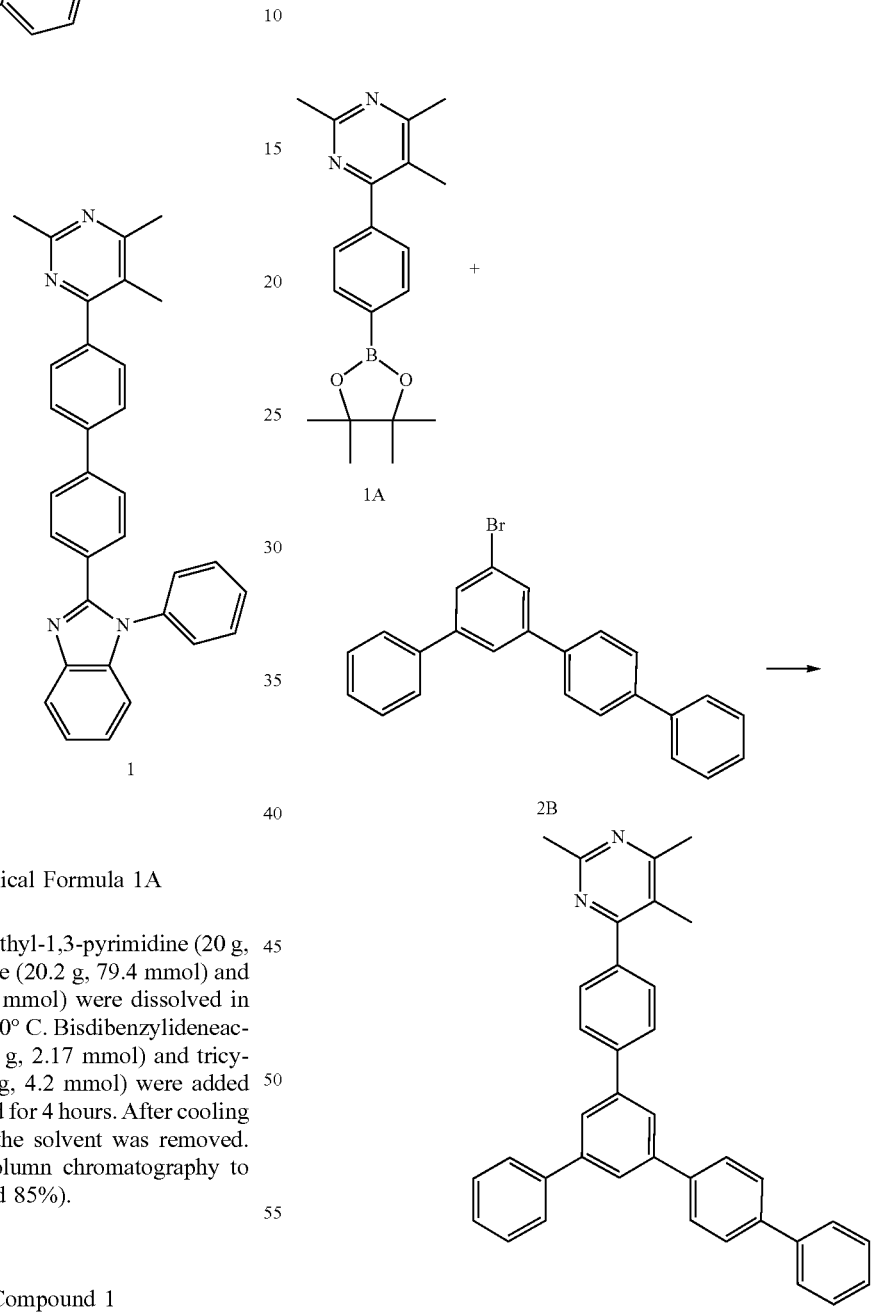

(1) Preparation of Chemical Formula 1A 4-(4-Bromophenyl)-2,5,6-trimethyl-1,3-pyrimidine (20 g, 72.2 mmol), bispinacolatodiborane (20.2 g, 79.4 mmol) and potassium acetate (21.2 g, 216.6 mmol) were dissolved in dioxin (700 mL), and heated to 130° C. Bisdibenzylideneacetone palladium (Pd(dba$_2$)) (1.24 g, 2.17 mmol) and tricyclohexylphosphine (PCy$_3$) (1.24 g, 4.2 mmol) were added thereto, and the result was refluxed for 4 hours. After cooling the result to room temperature, the solvent was removed. The result was purified using column chromatography to obtain Compound 1A (20 g, yield 85%).

MS: [M+H]$^+$=324

(2) Preparation of Compound 1

Compound 1A (8.1 g, 25 mmol), Compound 1B (8.7 g, 25 mmol) and potassium carbonate (K$_2$CO$_3$) (10.4 g, 75 mmol) were dissolved in tetrahydrofuran (THF) (300 mL) and H$_2$O (100 ml), and heated to 90° C. Tetrakis(triphenylphosphine) palladium (Pd(PPh$_3$)$_4$) (0.58 g, 0.5 mmol) was added thereto, and the result was refluxed for 4 hours. After cooling the result to room temperature, the water layer was removed.

Compound 2 (10 g, yield 80%) was obtained in the same manner as in the preparation of Compound 1 of Synthesis Example 1 except that Compound 2B was used instead of Compound 1B.

MS: [M+H]$^+$=502

<Synthesis Example 3> Preparation of Compound 3

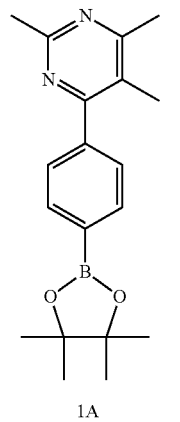
1A

+

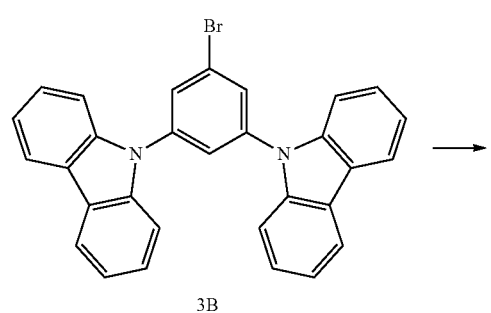
3B

→

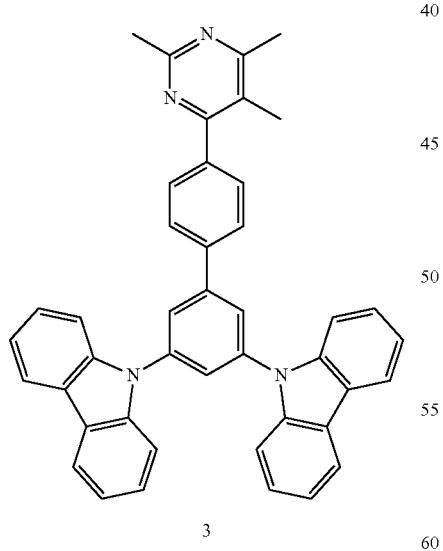
3

Compound 3 (11 g, yield 73%) was obtained in the same manner as in the preparation of Compound 1 of Synthesis Example 1 except that Compound 3B was used instead of Compound 1B.

MS: [M+H]$^+$=604

<Synthesis Example 4> Preparation of Compound 4

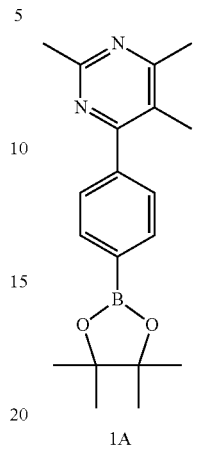
1A

+

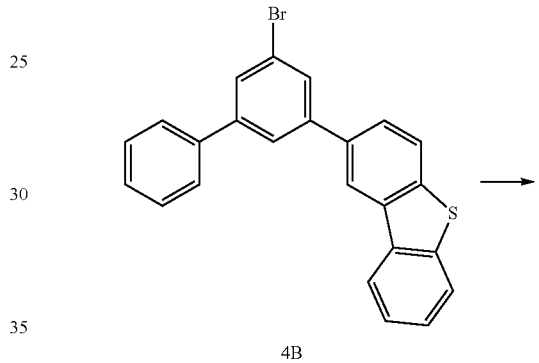
4B

→

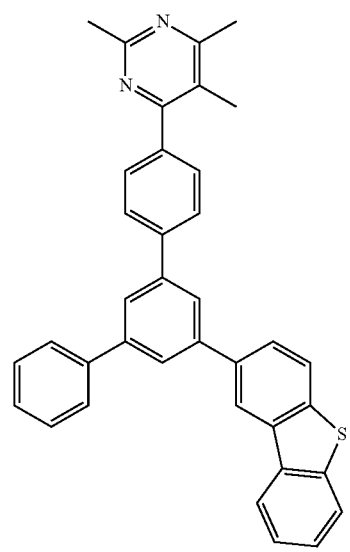
4

Compound 4 (11.5 g, yield 76%) was obtained in the same manner as in the preparation of Compound 1 of Synthesis Example 1 except that Compound 4B was used instead of Compound 1B.

MS: [M+H]$^+$=604

<Synthesis Example 5> Preparation of Compound 5

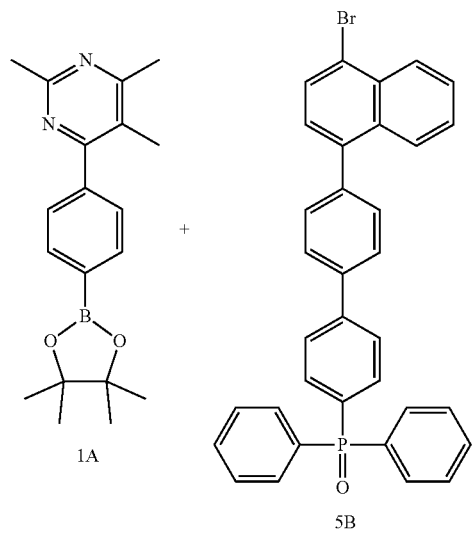

<Synthesis Example 6> Preparation of Compound 6

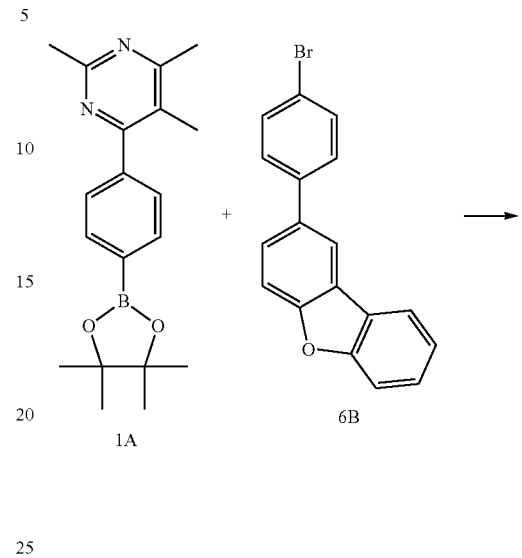

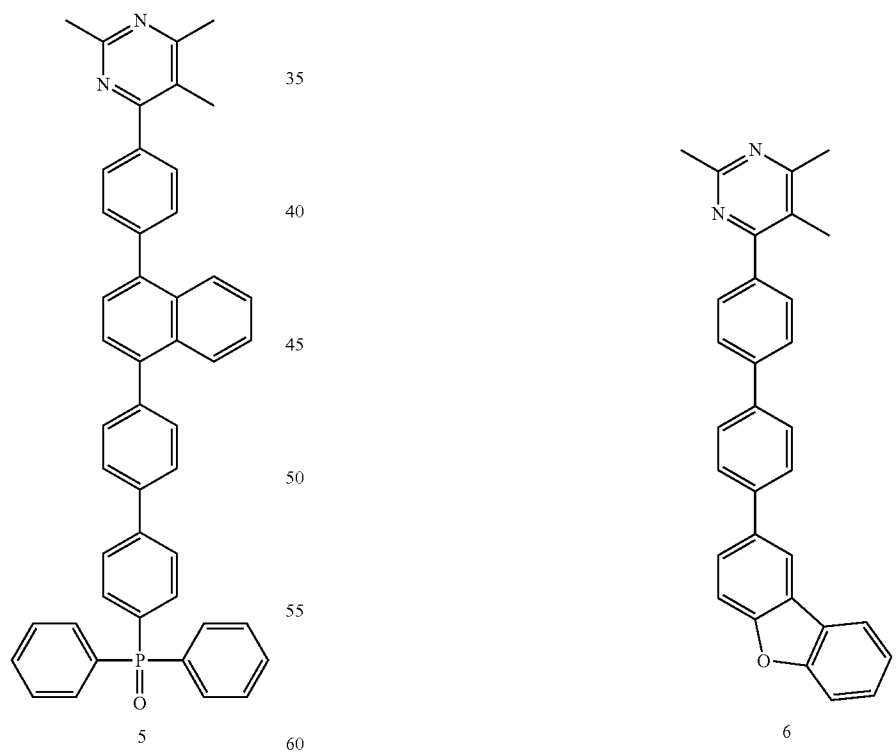

Compound 5 (13 g, yield 77%) was obtained in the same manner as in the preparation of Compound 1 of Synthesis Example 1 except that Compound 5B was used instead of Compound 1B.

MS: [M+H]$^+$=676

Compound 6 (7.5 g, yield 68%) was obtained in the same manner as in the preparation of Compound 1 of Synthesis Example 1 except that Compound 6B was used instead of Compound 1B.

MS: [M+H]$^+$=440

<Synthesis Example 7> Preparation of Compound 7

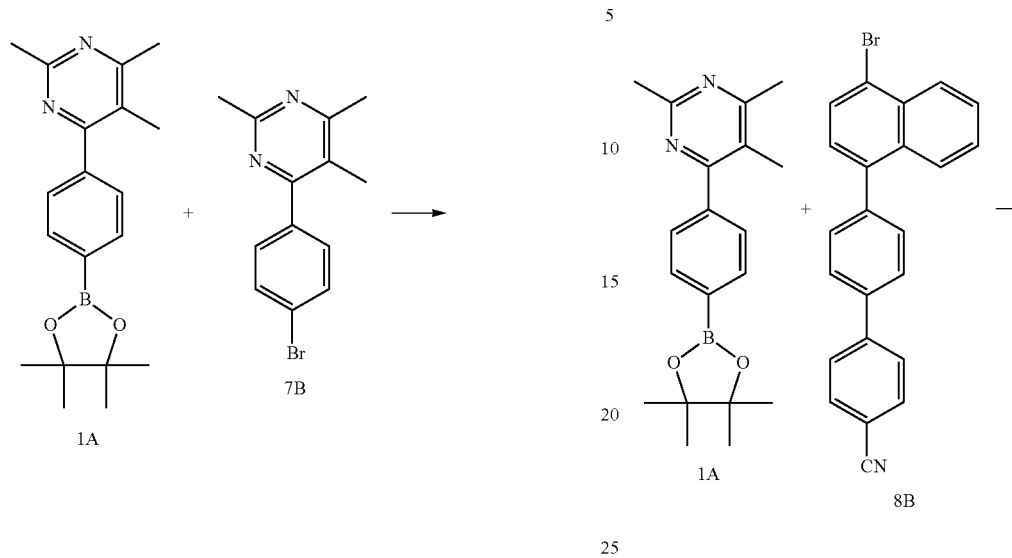

Compound 7 (8 g, yield 81%) was obtained in the same manner as in the preparation of Compound 1 of Synthesis Example 1 except that Compound 7B was used instead of Compound 1B.

MS: [M+H]$^+$=394

<Synthesis Example 8> Preparation of Compound 8

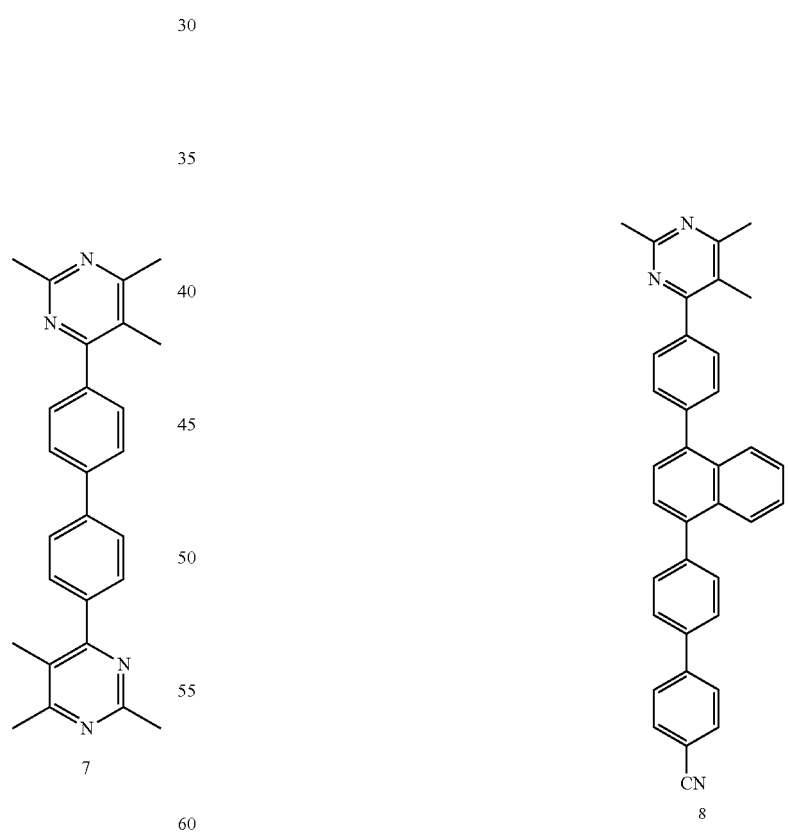

Compound 8 (8 g, yield 72%) was obtained in the same manner as in the preparation of Compound 1 of Synthesis Example 1 except that Compound 8B was used instead of Compound 1B.

MS: [M+H]$^+$=501

<Synthesis Example 9> Preparation of Compound 9
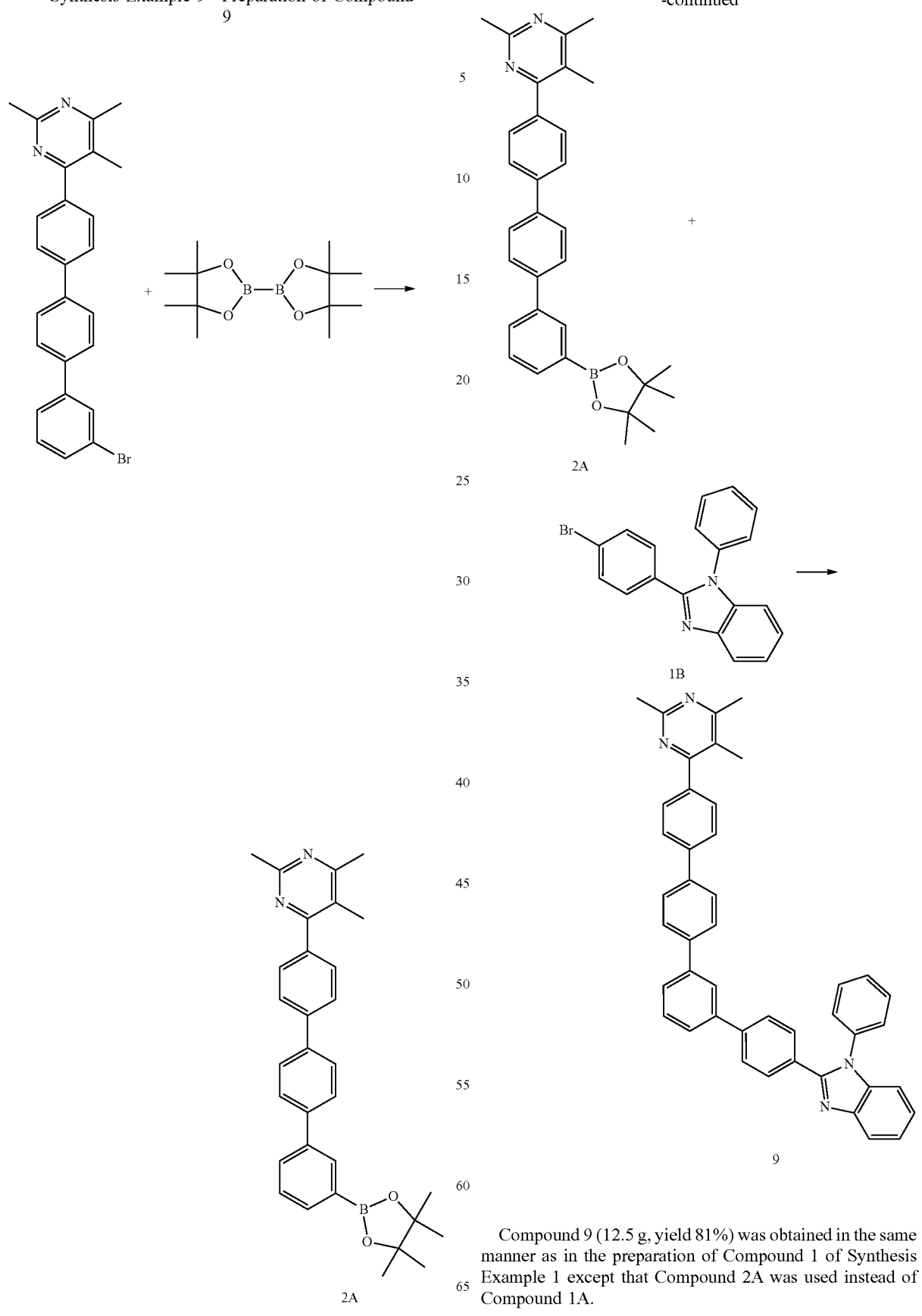
Compound 9 (12.5 g, yield 81%) was obtained in the same manner as in the preparation of Compound 1 of Synthesis Example 1 except that Compound 2A was used instead of Compound 1A.
MS: $[M+H]^+$=618

\<Synthesis Example 10\> Preparation of Compound 10

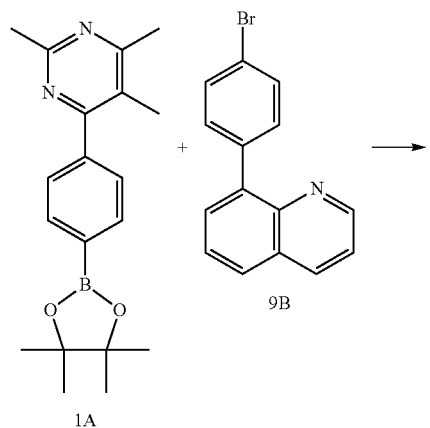

Compound 10 (7 g, yield 70%) was obtained in the same manner as in the preparation of Compound 1 of Synthesis Example 1 except that Compound 9B was used instead of Compound 1B.

MS: [M+H]$^+$=401

\<Synthesis Example 11\> Preparation of Compound 11

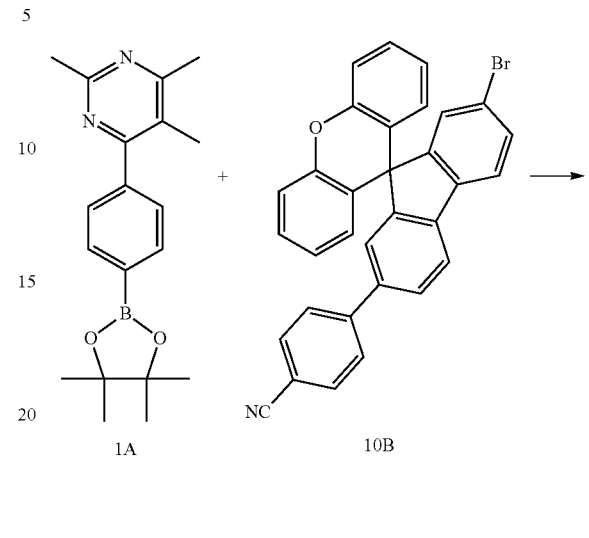

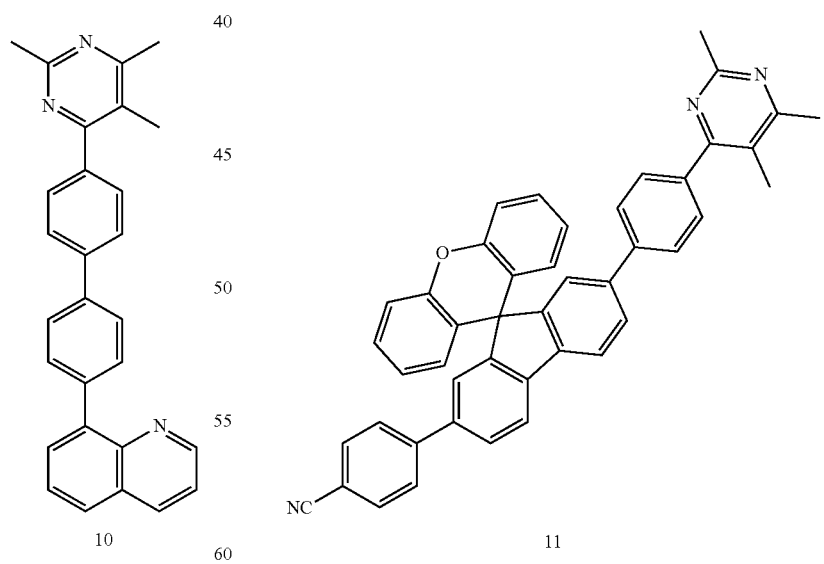

Compound 11 (7 g, yield 73%) was obtained in the same manner as in the preparation of Compound 1 of Synthesis Example 1 except that Compound 10B was used instead of Compound 1B.

MS: [M+H]$^+$=629

<Synthesis Example 12> Preparation of Compound 12

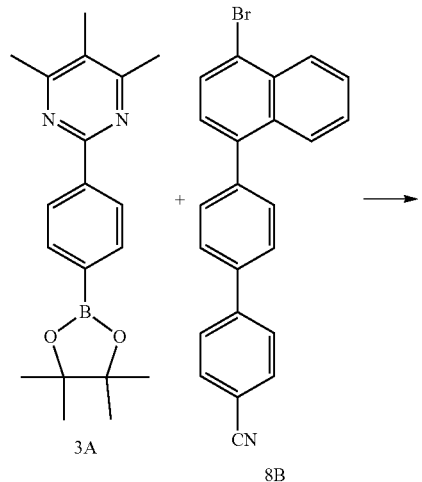

Compound 12 (7 g, yield 72%) was obtained in the same manner as in the preparation of Compound 8 of Synthesis Example 8 except that Compound 3A was used instead of Compound 1A.

MS: [M+H]$^+$=501

<Synthesis Example 13> Preparation of Compound 13

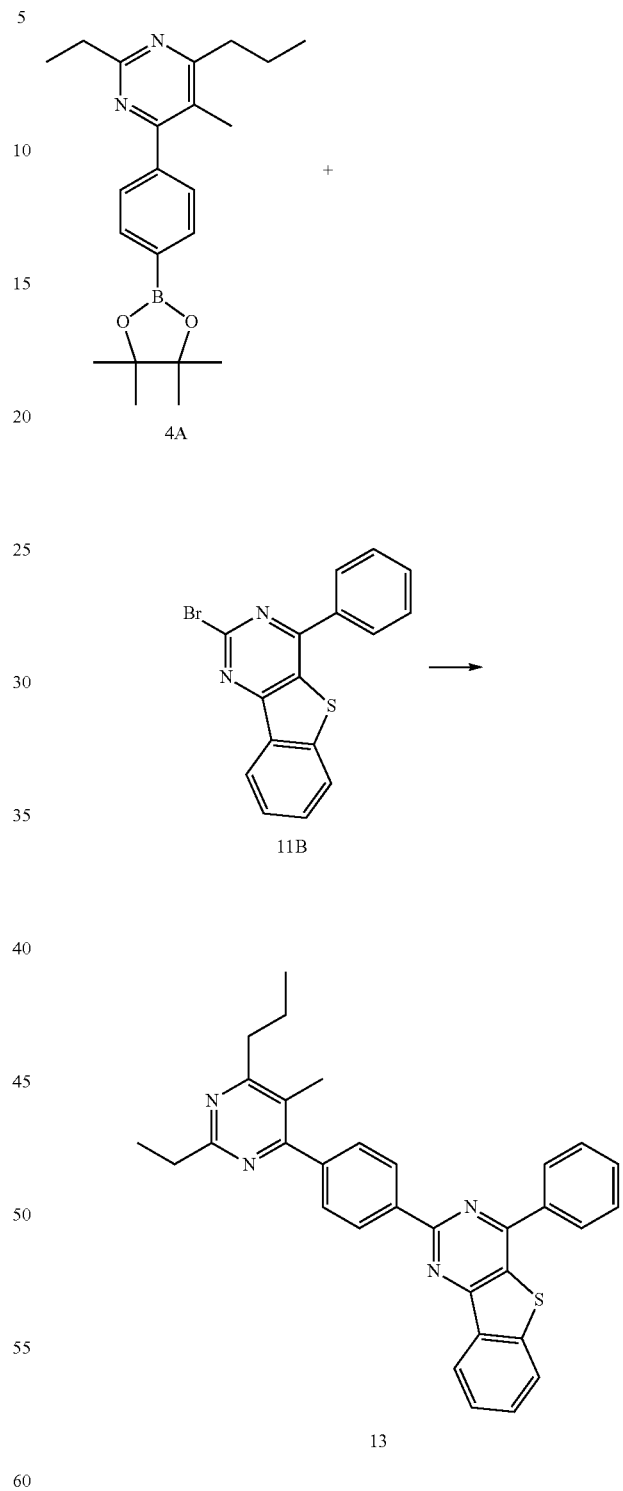

Compound 13 (10 g, yield 80%) was obtained in the same manner as in the preparation of Compound 1 of Synthesis Example 1 except that Compound 4A was used instead of Compound 1A, and Compound 11B was used instead of Compound 1B.

MS: [M+H]$^+$=500

<Synthesis Example 14> Preparation of Compound 14

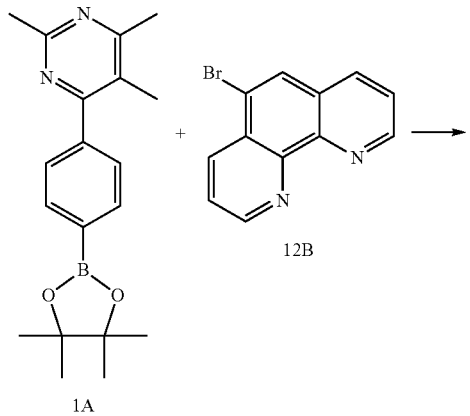

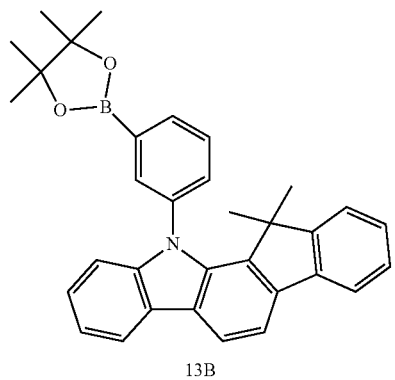

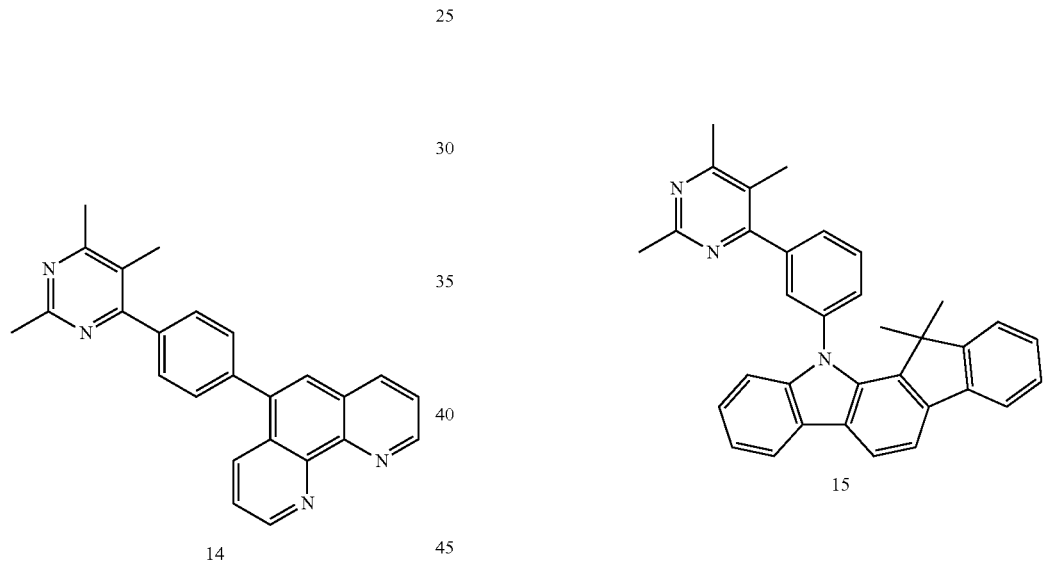

Compound 14 (7.7 g, yield 82%) was obtained in the same manner as in the preparation of Compound 1 of Synthesis Example 1 except that Compound 12B was used instead of Compound 1B.

MS: [M+H]$^+$=376

Compound 15 (8.5 g, yield 71%) was obtained in the same manner as in the preparation of Compound 1 of Synthesis Example 1 except that Compound 5A was used instead of Compound 1A, and Compound 13B was used instead of Compound 1B.

MS: [M+H]$^+$=479

<Synthesis Example 15> Preparation of Compound 15

<Synthesis Example 16> Preparation of Compound 16

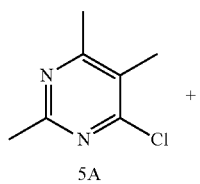

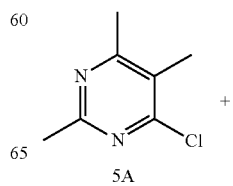

-continued

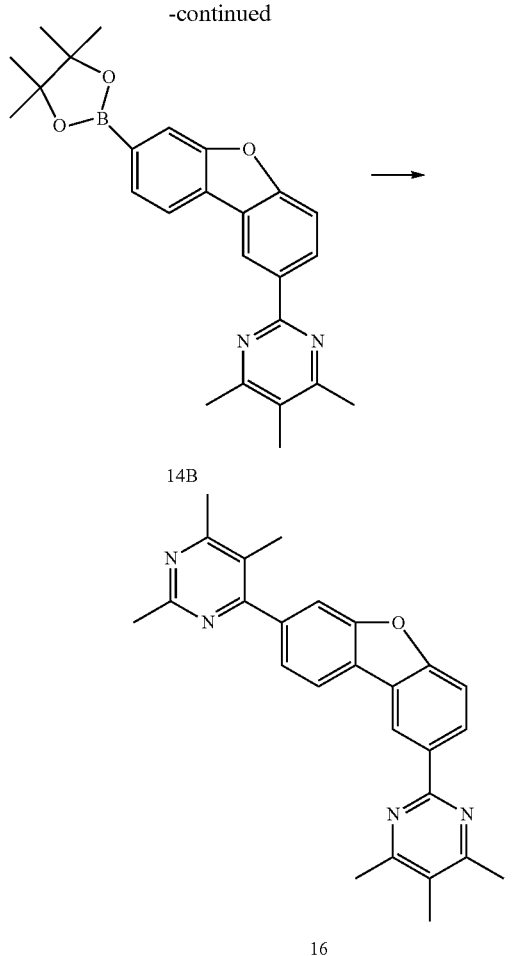

14B

16

-continued

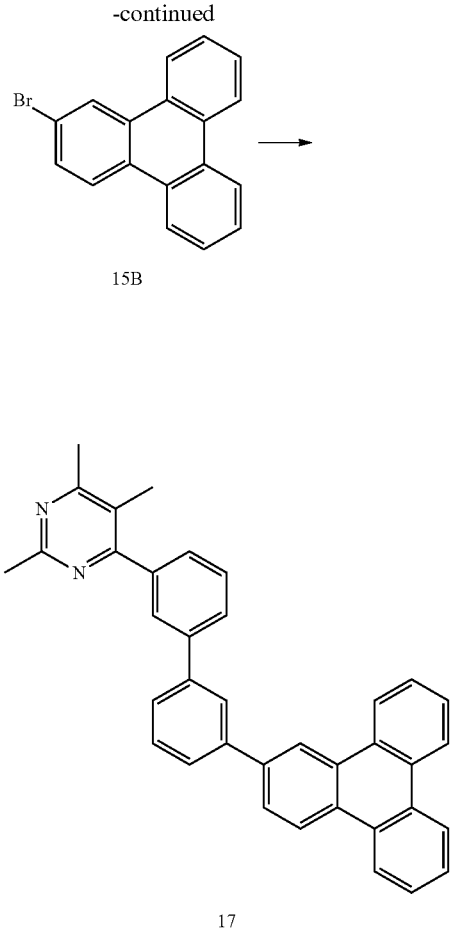

15B

17

Compound 16 (7.8 g, yield 76%) was obtained in the same manner as in the preparation of Compound 1 of Synthesis Example 1 except that Compound 5A was used instead of Compound 1A, and Compound 14B was used instead of Compound 1B.

MS: [M+H]$^+$=408

<Synthesis Example 17> Preparation of Compound 17

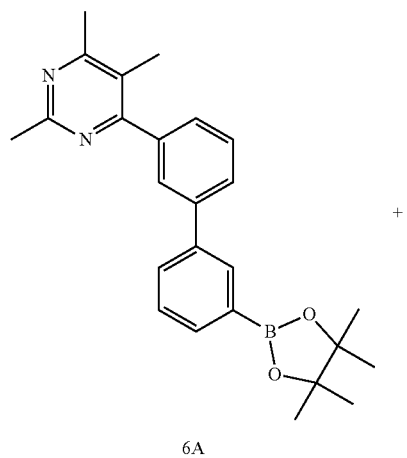

6A

Compound 17 (10 g, yield 80%) was obtained in the same manner as in the preparation of Compound 1 of Synthesis Example 1 except that Compound 6A was used instead of Compound 1A, and Compound 15B was used instead of Compound 1B.

MS: [M+H]$^+$=500

<Synthesis Example 18> Preparation of Compound 18

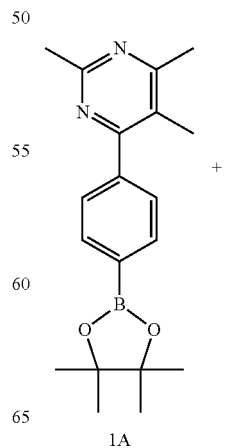

1A

-continued

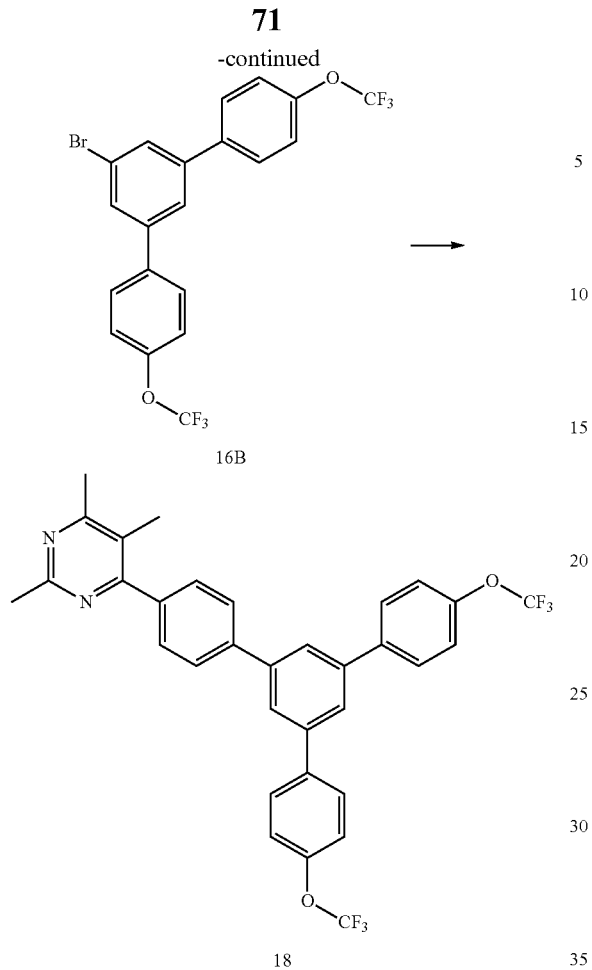

16B

18

Compound 18 (11.5 g, yield 77%) was obtained in the same manner as in the preparation of Compound 1 of Synthesis Example 1 except that Compound 16B was used instead of Compound 1B.
MS: [M+H]⁺=594

Experimental Example 2: Manufacture of Device

Example 1-1

A glass substrate (corning 7059 glass) on which indium tin oxide (ITO) was coated as a thin film to a thickness of 100 nm was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned sequentially with isopropyl alcohol, acetone and methanol solvents, and then dried.

On the transparent ITO electrode prepared as above, a hole injection layer was formed by thermal vacuum depositing hexanitrile hexaazatriphenylene (HAT) to a thickness of 50 nm. Thereon, HT1 (40 nm), a material transferring holes, was vacuum deposited, and then host BH1 and dopant BD1 compounds were deposited to a thickness of 30 nm as a light emitting layer. After depositing a hole blocking layer (electron control layer) on the light emitting layer by depositing an ET-A compound to a thickness of 5 nm, an electron injection and transfer layer was formed to a thickness of 35 nm by vacuum depositing Compound 1 synthesized in Synthesis Example 1 and lithium quinolate (LiQ) in a weight ratio of 1:1. On the electron injection and transfer layer, a cathode was formed by consecutively depositing lithium fluoride (LiF) to a thickness of 1.2 nm and aluminum to a thickness of 200 nm. An organic light emitting device was manufactured as a result.

In the above-mentioned process, the deposition rates of the organic materials were maintained at 0.04 nm/sec to 0.07 nm/sec, the deposition rates of the lithium fluoride and the aluminum of the cathode were maintained at 0.03 nm/sec and 0.2 nm/sec, respectively, and the degree of vacuum during the deposition was maintained at $2 \times 10^{-7}$ torr to $5 \times 10^{-6}$ torr to manufacture an organic light emitting device.

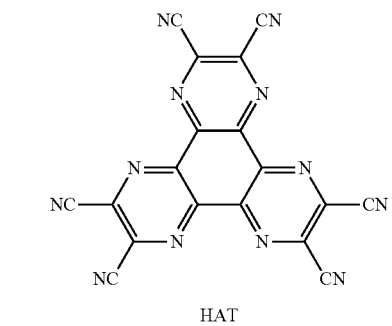

HAT

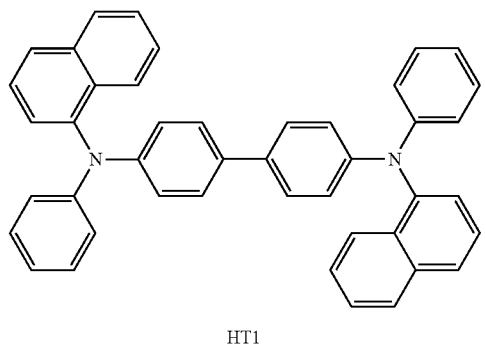

HT1

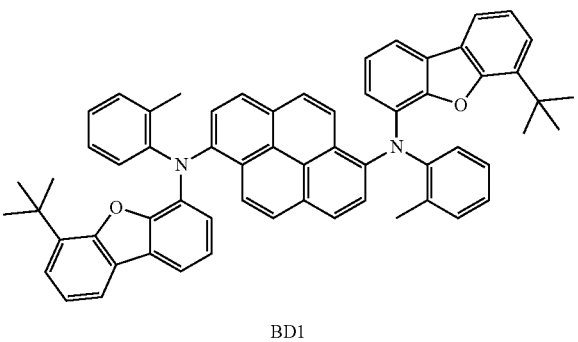

BD1

-continued
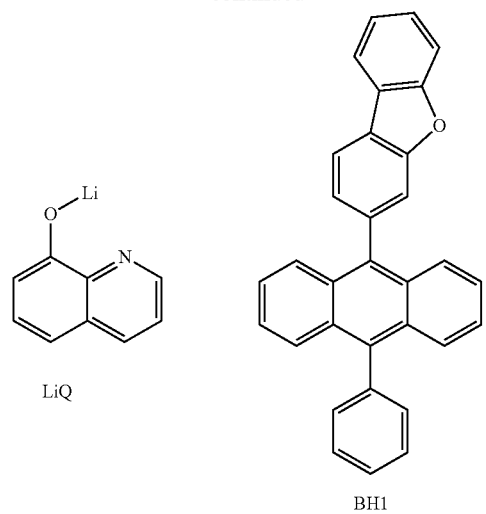
LiQ
BH1
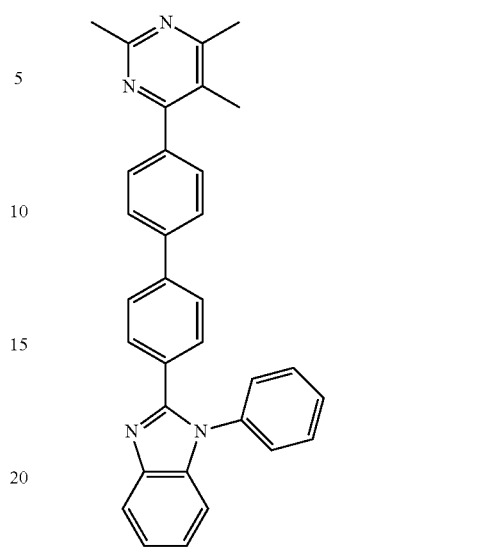
1
2
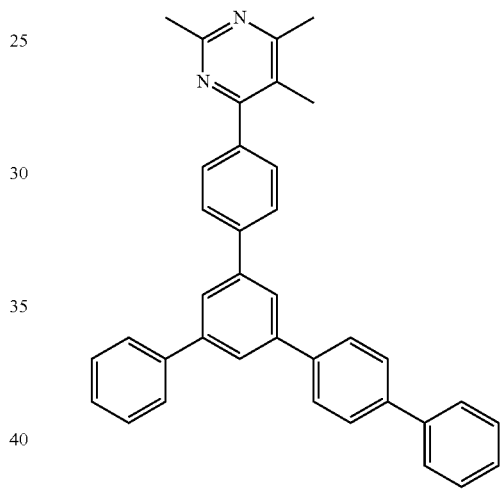
ET-A
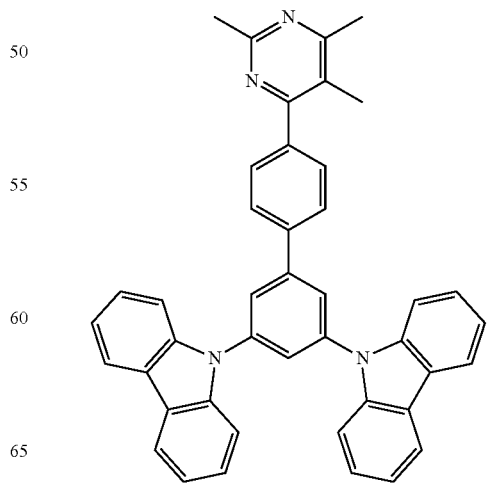
3
Additional Examples and Comparative Examples
Organic light emitting devices were manufactured in the same manner as in Example 1-1 except that compounds described in the following Table 1 were each used instead of Compound 1 as the electron injection and transfer layer material.

75
-continued
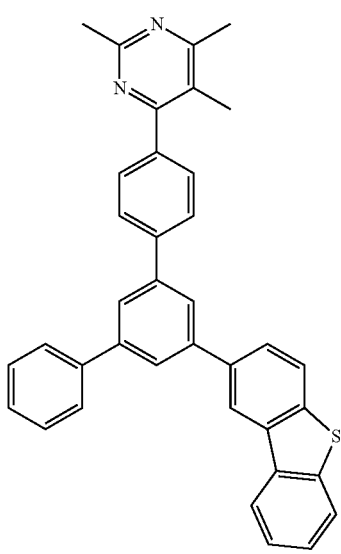
76
-continued
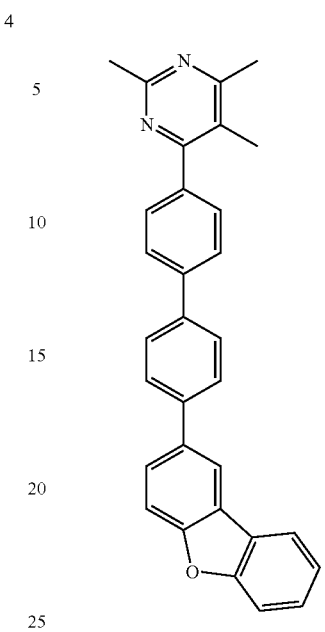
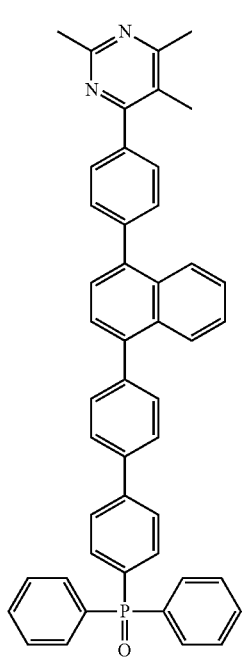
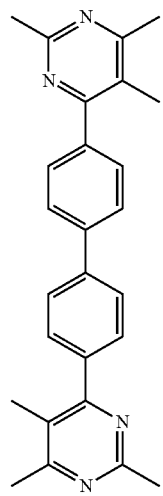

77
-continued
78
-continued
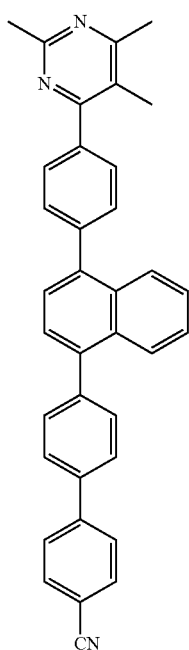
8
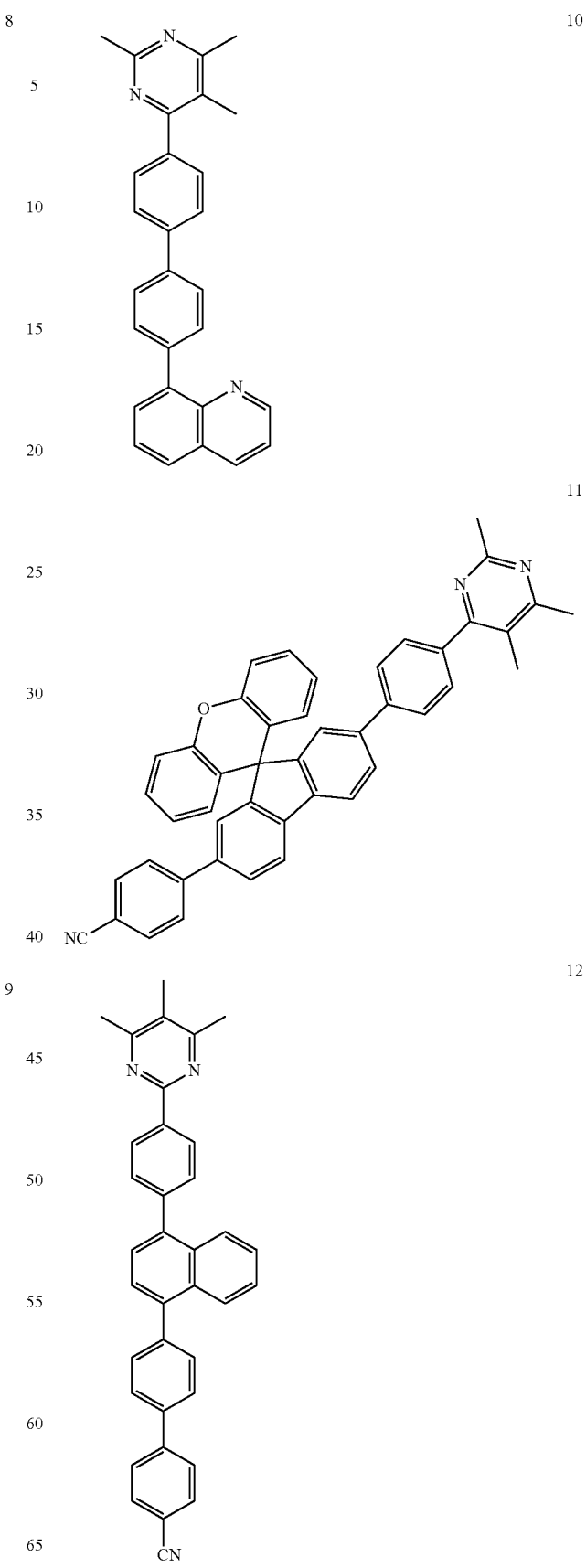
10
11
9
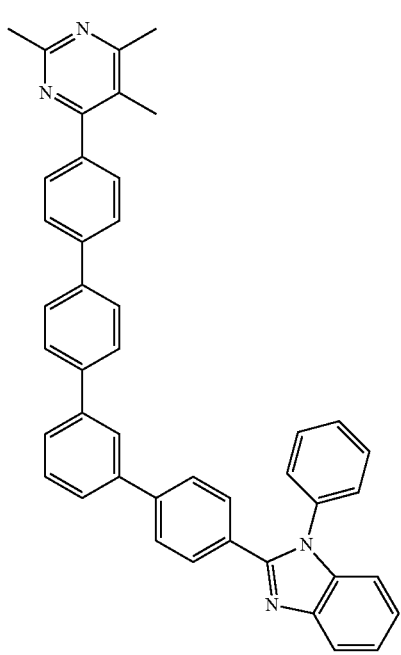
12

13
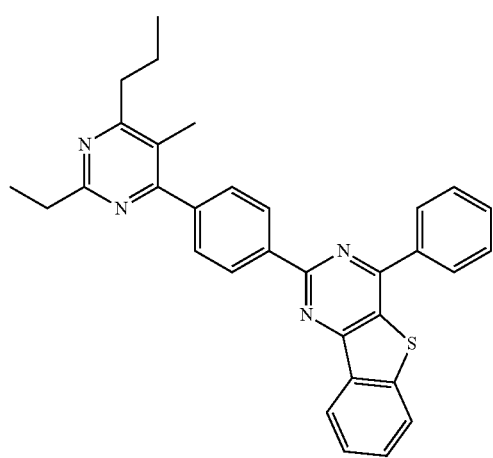
14
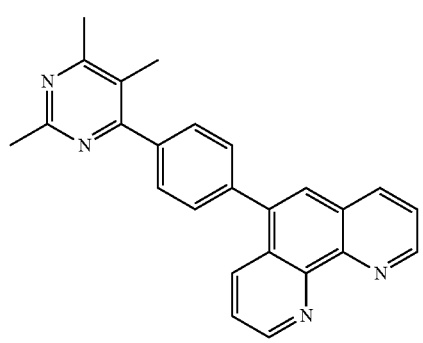
15
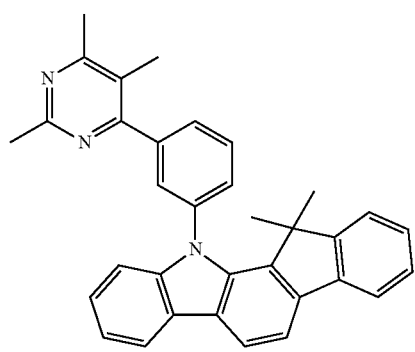
16
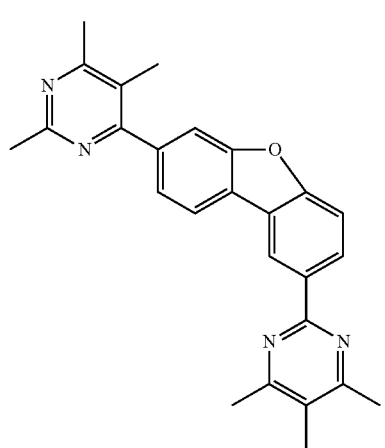
17
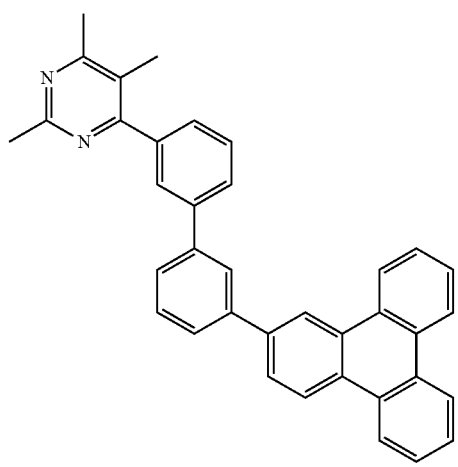
18
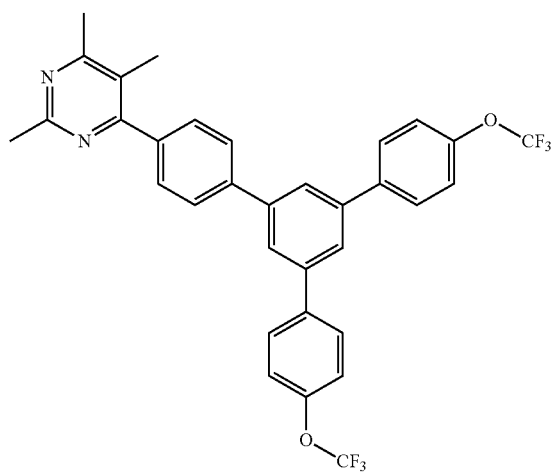
ET1
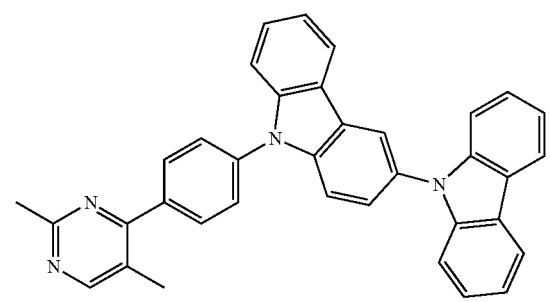

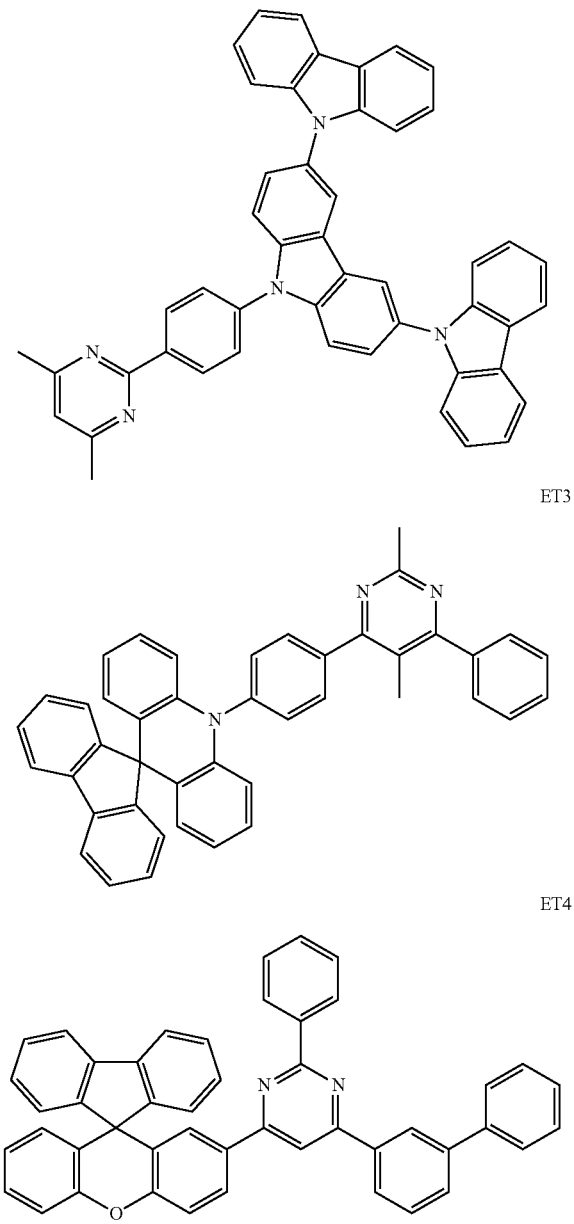

For each of the organic light emitting devices manufactured in the experimental example, driving voltage and light emission efficiency were measured at current density of 10 mA/cm², and time taken for luminance becoming 98% with respect to initial luminance (LT98) was measured at current density of 20 mA/cm². The results are shown in the following Table 1.

TABLE 1

| Category | Compound | Voltage (V) | Current Efficiency (cd/A) | Color Coordinate (x, y) | LT98 (h) |
|---|---|---|---|---|---|
| Example 1-1 | 1 | 3.78 | 5.21 | (0.137, 0.126) | 59 |
| Example 1-2 | 2 | 3.89 | 4.82 | (0.138, 0.124) | 62 |
| Example 1-3 | 3 | 3.92 | 4.80 | (0.138, 0.126) | 71 |
| Example 1-4 | 4 | 3.97 | 4.81 | (0.138, 0.129) | 66 |
| Example 1-5 | 5 | 4.01 | 4.81 | (0.138, 0.125) | 65 |
| Example 1-6 | 6 | 3.97 | 4.86 | (0.138, 0.124) | 59 |
| Example 1-7 | 7 | 4.10 | 4.75 | (0.137, 0.126) | 79 |
| Example 1-8 | 8 | 3.97 | 4.91 | (0.138, 0.125) | 65 |
| Example 1-9 | 9 | 3.99 | 5.05 | (0.138, 0.126) | 57 |
| Example 1-10 | 10 | 4.00 | 4.88 | (0.139, 0.123) | 62 |
| Example 1-11 | 11 | 3.99 | 4.92 | (0.138, 0.126) | 62 |
| Example 1-12 | 12 | 4.05 | 4.90 | (0.138, 0.126) | 69 |
| Example 1-13 | 13 | 3.69 | 5.01 | (0.138, 0.125) | 55 |
| Example 1-14 | 14 | 3.83 | 5.05 | (0.137, 0.126) | 63 |
| Example 1-15 | 15 | 3.77 | 5.01 | (0.138, 0.124) | 54 |
| Example 1-16 | 16 | 4.04 | 4.95 | (0.137, 0.126) | 62 |
| Example 1-17 | 17 | 3.81 | 5.12 | (0.138, 0.124) | 55 |
| Example 1-18 | 18 | 3.90 | 4.83 | (0.138, 0.124) | 52 |
| Comparative Example 1-1 | ET1 | 4.21 | 4.21 | (0.139, 0.129) | 31 |
| Comparative Example 1-2 | ET2 | 4.26 | 4.15 | (0.140, 0.128) | 38 |
| Comparative Example 1-3 | ET3 | 4.15 | 4.69 | (0.138, 0.128) | 25 |
| Comparative Example 1-4 | ET4 | 4.25 | 4.45 | (0.137, 0.124) | 37 |

Based on Table 1, it was identified that the devices including compounds having pyrimidine substituted with 3 alkyl groups like Compound 1 of the present disclosure had lower driving voltage, higher current efficiency, and, particularly, significantly enhanced lifetime properties compared to the devices including the compounds of Comparative Examples ET1 to ET4.

REFERENCE NUMERALS

1: Substrate
2: Anode
3: Hole Injection Layer
4: Hole Transfer Layer
4a: First Hole Transfer Layer
4b: Second Hole Transfer Layer
4c: Third Hole Transfer Layer
4d: Fourth Hole Transfer Layer
4e: Fifth Hole Transfer Layer
4f: Sixth Hole Transfer Layer
4p: p-Doped Hole Transfer Layer
4R: Red Hole Transfer Layer
4G: Green Hole Transfer Layer
4B: Blue Hole Transfer Layer
5: Electron Blocking Layer
6: Light Emitting Layer
6a: First Light Emitting Layer
6b: Second Light Emitting Layer
6c: Third Light Emitting Layer
6BF: Blue Fluorescent Light Emitting Layer
6BFa: First Blue Fluorescent Light Emitting Layer
6BFb: Second Blue Fluorescent Light Emitting Layer
6YGP: Yellow Green Phosphorescent Light Emitting Layer
6RP: Red Phosphorescent Light Emitting Layer
6GP: Green Phosphorescent Light Emitting Layer
7: Hole Blocking Layer
8: Electron Injection and Transfer Layer
9: Electron Transfer Layer
9a: First Electron Transfer Layer
9b: Second Electron Transfer Layer 9c: Third Electron Transfer Layer
10: Electron Injection Layer
11: Cathode
12: N-Type Charge Generating Layer
12a: First N-Type Charge Generating Layer
12b: Second N-Type Charge Generating Layer
13: P-Type Charge Generating Layer
13a: First P-Type Charge Generating Layer
13b: Second P-Type Charge Generating Layer
14: Capping Layer

The invention claimed is:

1. A compound of Chemical Formula 1:

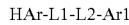  Chemical Formula 1 wherein, in Chemical Formula 1;

HAr is a group of the following Chemical Formula A-1 or A-2;

L1 and L2 are the same as or different from each other, and each independently is a direct bond; a monocyclic or polycyclic arylene group that is unsubstituted or substituted with an alkyl group, an aryl group or a heteroaryl group; or a monocyclic or polycyclic heteroarylene group that is unsubstituted or substituted with an alkyl group, an aryl group or a heteroaryl group; and Ar1 is a monocyclic or polycyclic aryl group that is unsubstituted or substituted with a cyano group, an alkyl group, an aryl group or a heteroaryl group; or a monocyclic or polycyclic heteroaryl group that is unsubstituted or substituted with a cyano group, an alkyl group, an aryl group or a heteroaryl group, provided that Ar1 is not 9,9-spirobifluorene;

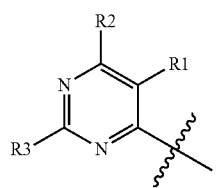 < Chemical Formula A-1 >

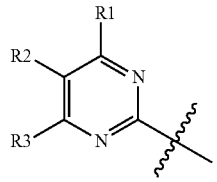 < Chemical Formula A-2 > wherein in Chemical Formulae A-1 and A-2;

R1 to R3 are the same as or different from each other, and each independently is an unsubstituted linear or branched alkyl group; and

is a site bonding to L1 of Chemical Formula 1.

2. The compound of claim 1, wherein Chemical Formula 1 is one of the following Chemical Formula 1-1 or 1-2:

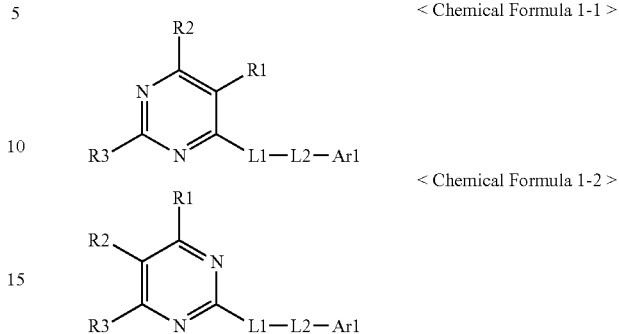

wherein in Chemical Formulae 1-1 and 1-2;

L1, L2 and Ar1 have the same definitions as in Chemical Formula 1; and

R1 to R3 have the same definitions as in Chemical Formulae A-1 and A-2.

3. The compound of claim 1, wherein L1 and L2 are the same as or different from each other, and each independently is a direct bond, a monocyclic arylene group that is unsubstituted or is substituted with an alkyl group or an aryl group, or a polycyclic arylene group.

4. The compound of claim 1, wherein Ar1 is a monocyclic aryl group that is unsubstituted or is substituted with a cyano group, an alkyl group, an arylphosphine oxide group, an aryl group or a heteroaryl group; a polycyclic aryl group; a monocyclic heteroaryl group that is unsubstituted or is substituted with an alkyl group or an aryl group; or a polycyclic heteroaryl group that is unsubstituted or is substituted with an aryl group, provided that Ar1 is not 9,9-spirobifluorene.

5. The compound of claim 1, wherein R1 to R3 are the same as or different from each other, and each independently is a linear alkyl group.

6. An organic light emitting device comprising:
a first electrode;
a second electrode provided opposite to the first electrode; and
one or more organic material layers provided between the first electrode and the second electrode,
wherein one or more layers of the organic material layers comprise the compound of claim 1.

7. The organic light emitting device of claim 6, wherein the organic material layer comprises an electron injection layer, an electron transfer layer, or a layer carrying out electron transfer and electron injection at the same time, and the electron injection layer, the electron transfer layer, or the layer carrying out electron transfer and electron injection at the same time comprises the compound.

8. The organic light emitting device of claim 6, wherein the organic material layer comprises a hole blocking layer, and the hole blocking layer comprises the compound.

9. The organic light emitting device of claim 6, wherein the organic material layer comprises a hole injection layer, a hole transfer layer, or a layer carrying out hole transfer and hole injection at the same time, and the hole injection layer, the hole transfer layer, or the layer carrying out hole transfer and hole injection at the same time comprises the compound.

10. The organic light emitting device of claim 6, wherein the organic material layer comprises a light emitting layer, and the light emitting layer comprises the compound.

11. The organic light emitting device of claim 6, wherein the organic material layer comprises one or more layers selected from the group consisting of a hole injection layer, a hole transfer layer, an electron injection layer, an electron transfer layer, an electron blocking layer, a hole blocking layer, a layer carrying out hole transfer and hole injection at the same time, and a layer carrying out electron transfer and electron injection at the same time.

12. The organic light emitting device of claim 6, wherein the organic material layer comprises a light emitting layer, the light emitting layer comprises a host and a dopant, and the dopant has a maximum light emission wavelength of 400 nm to 520 nm.

13. The organic light emitting device of claim 12, wherein the dopant is a blue fluorescent dopant.

14. The organic light emitting device of claim 6, wherein the organic material layer comprises two or more light emitting layers.

15. The organic light emitting device of claim 14, wherein at least one of the two or more light emitting layers comprises a blue fluorescent dopant.

16. The organic light emitting device of claim 6, wherein the organic material layer comprises a first stack comprising one or more light emitting layers; and a second stack comprising one or more light emitting layers, and comprises one or more charge generating layers between the first stack and the second stack.

17. The organic light emitting device of claim 6, wherein the organic material layer comprises a first stack comprising one or more light emitting layers; a second stack comprising one or more light emitting layers; and a third stack comprising one or more light emitting layers, and comprises one or more charge generating layers between each of the first stack and the second stack; and the second stack and the third stack.

18. A compound selected from among the following compounds:

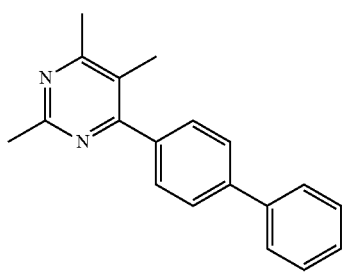

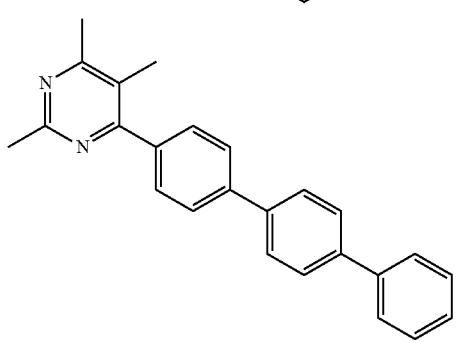

-continued

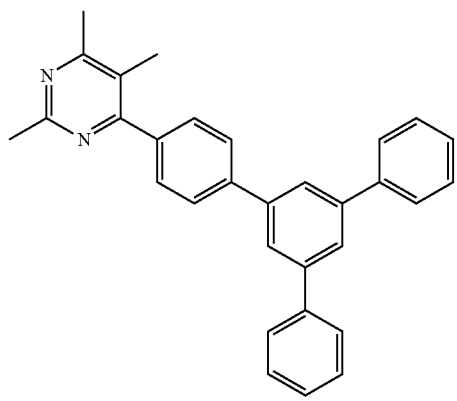

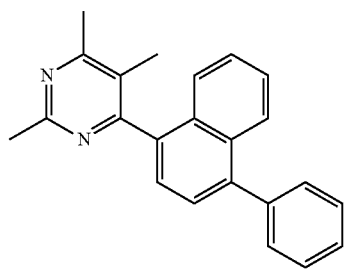

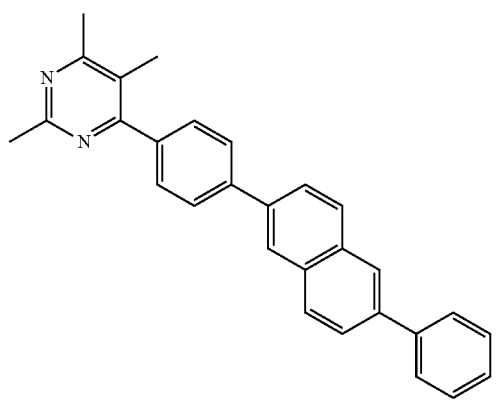

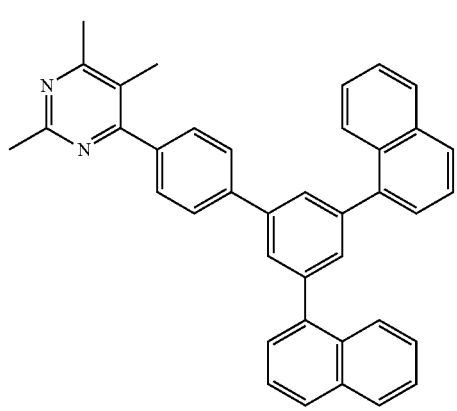

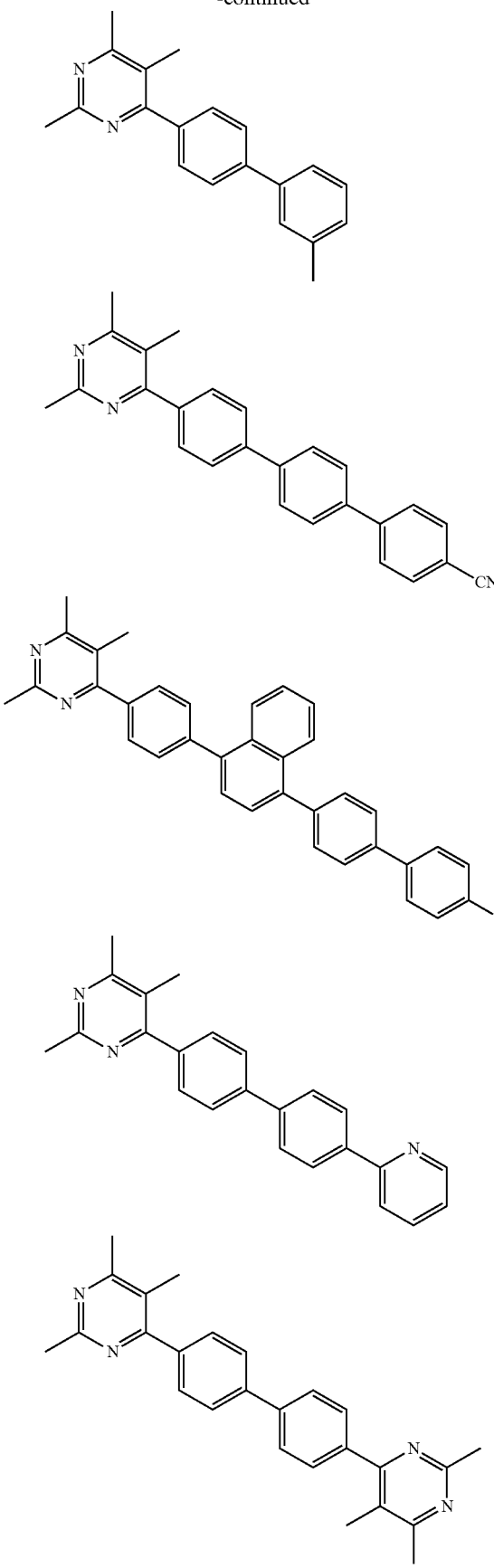
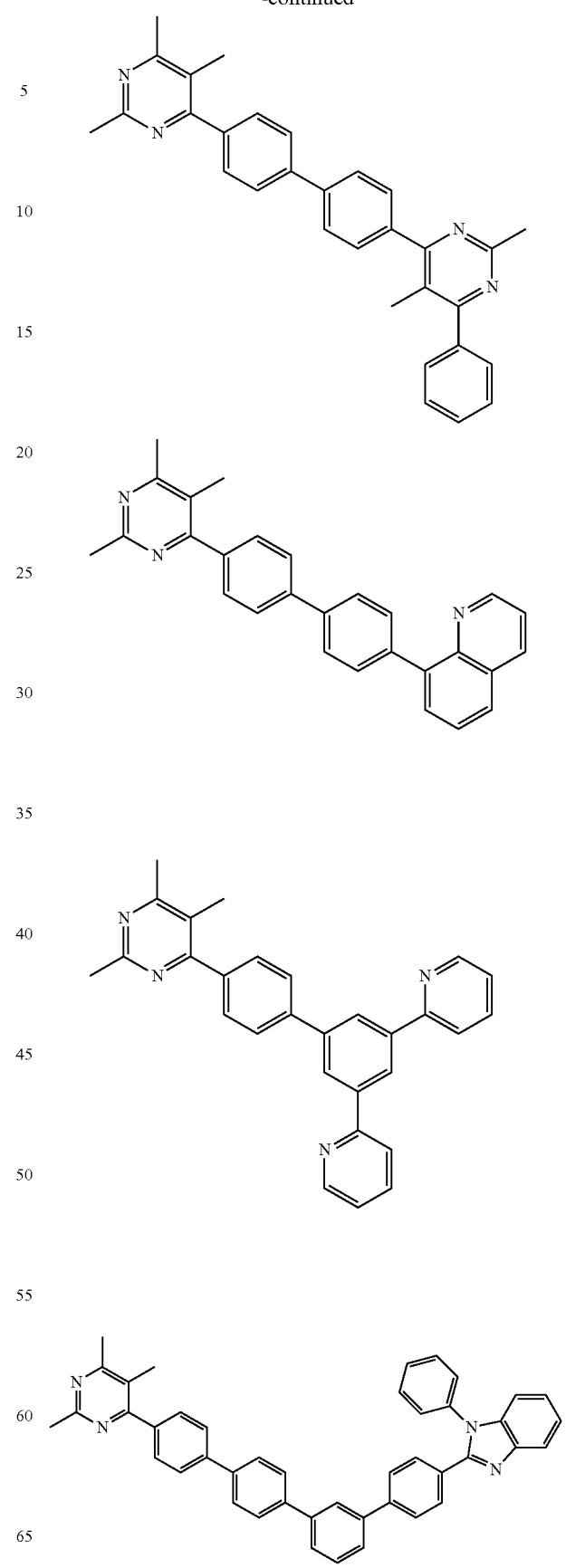

89
-continued
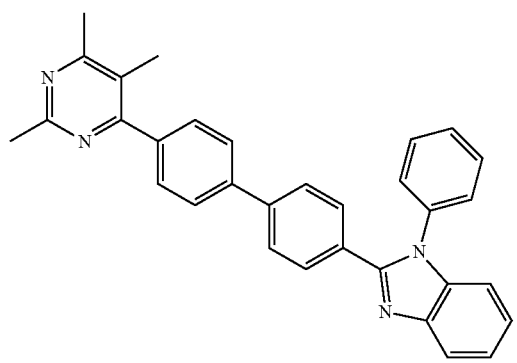
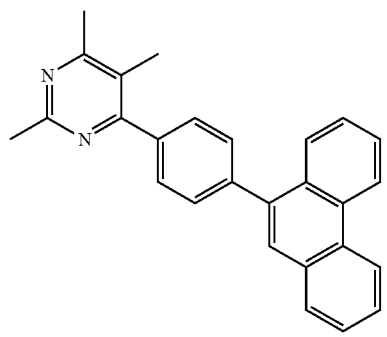
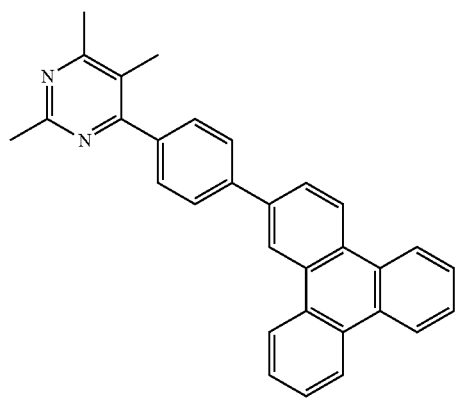
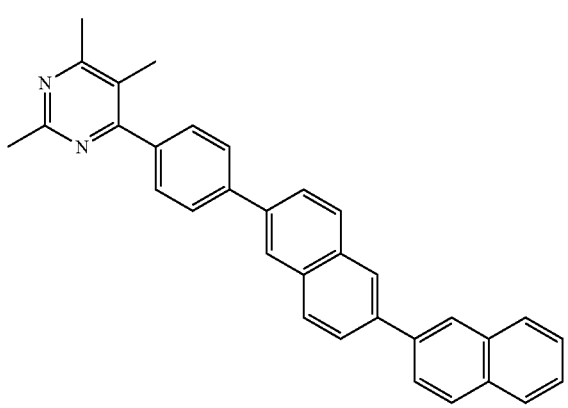
90
-continued
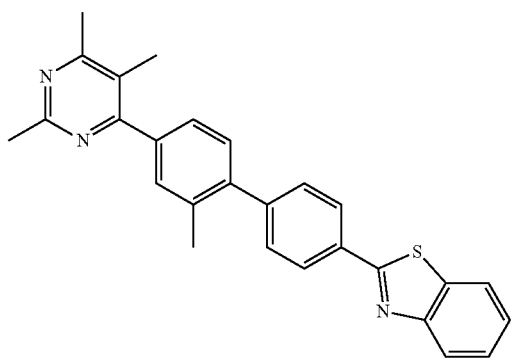
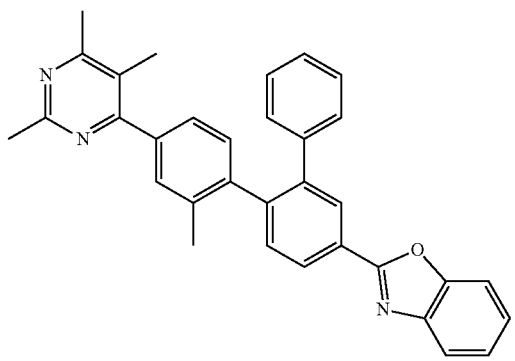
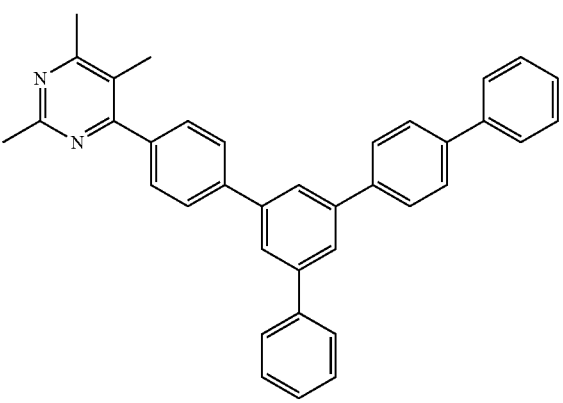
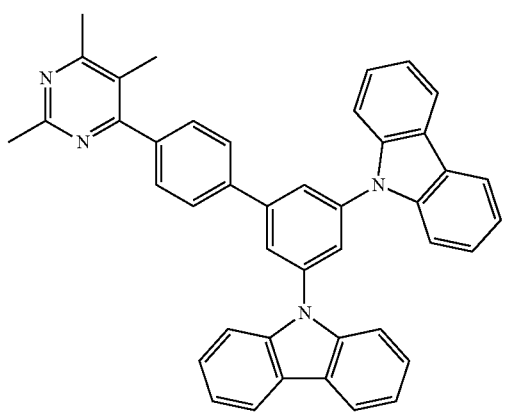

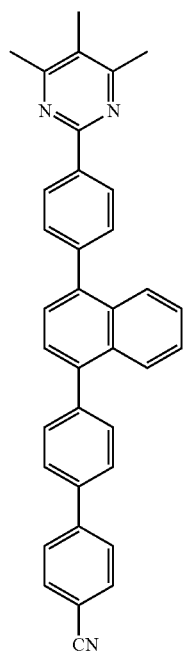
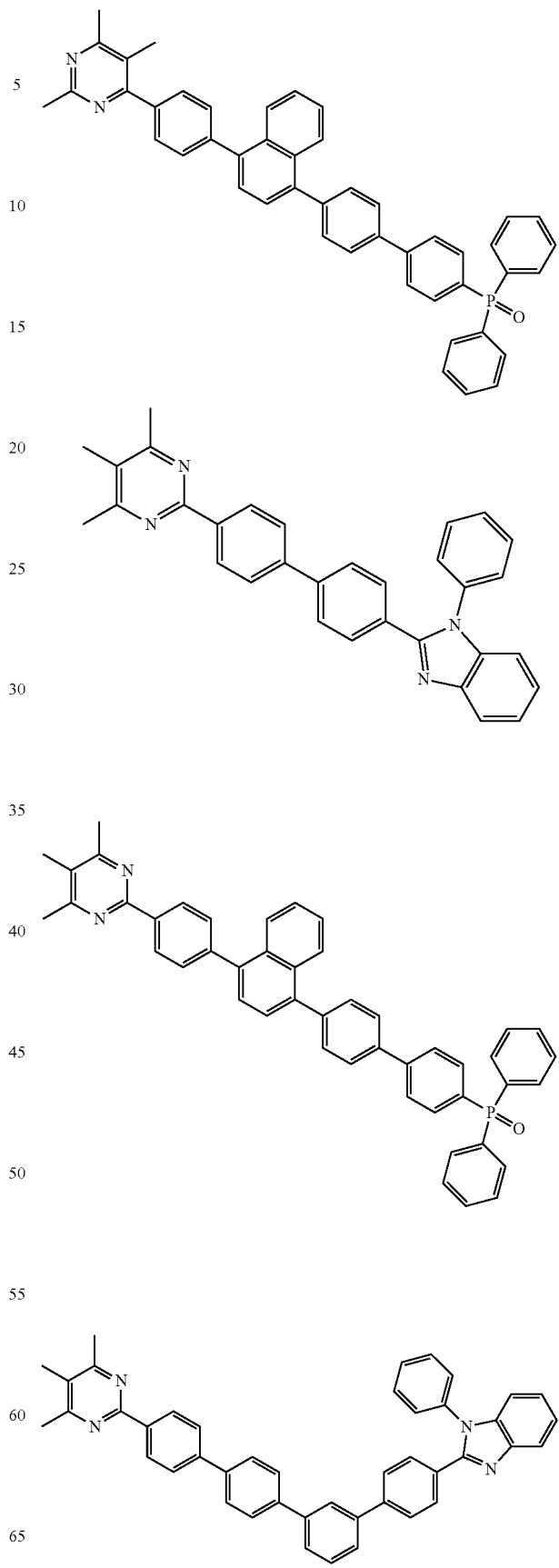

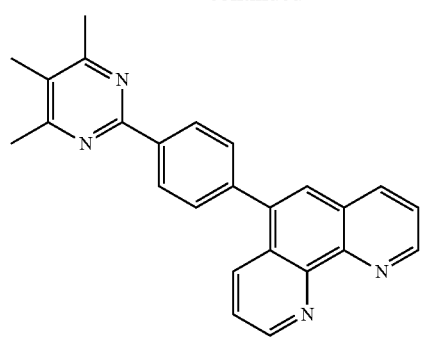
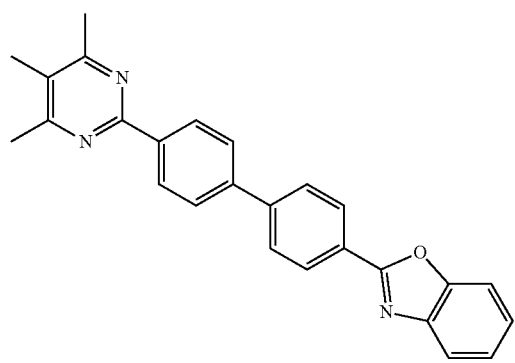
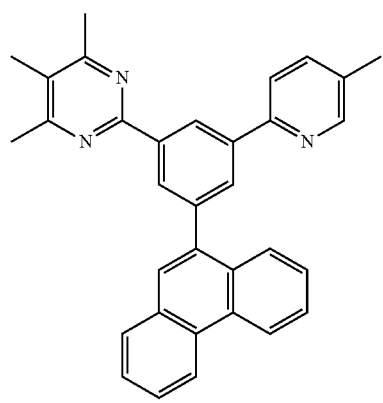
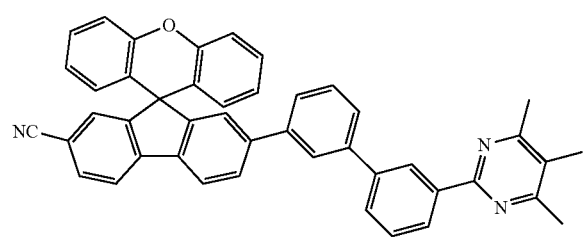
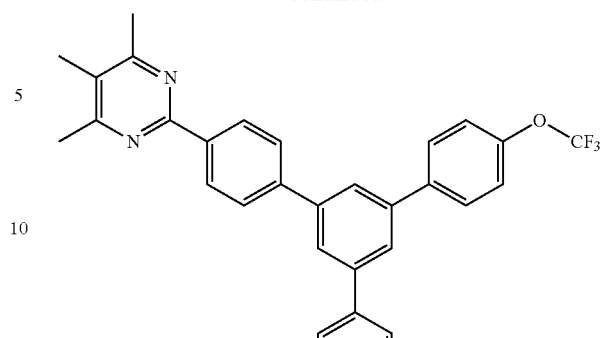
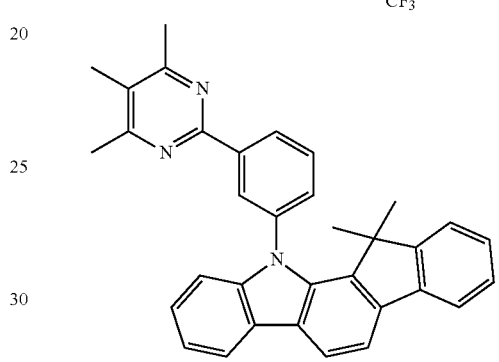
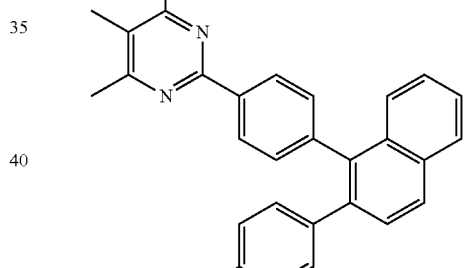
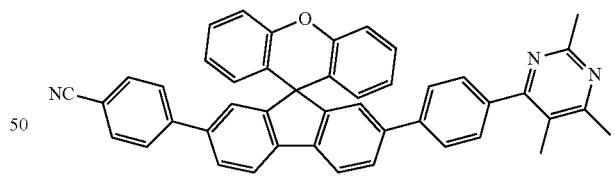
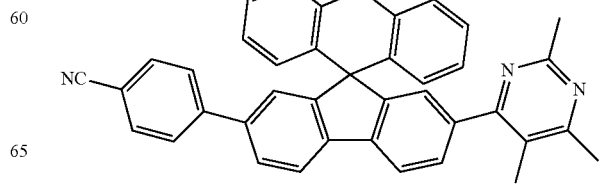

95
-continued
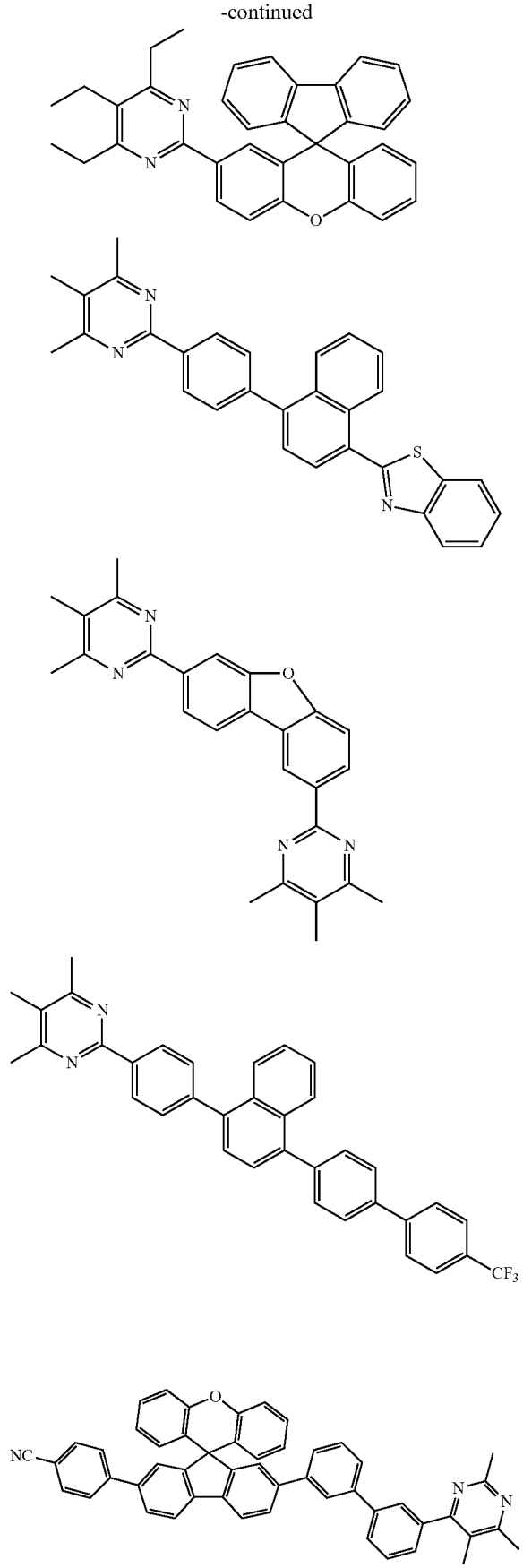
96
-continued
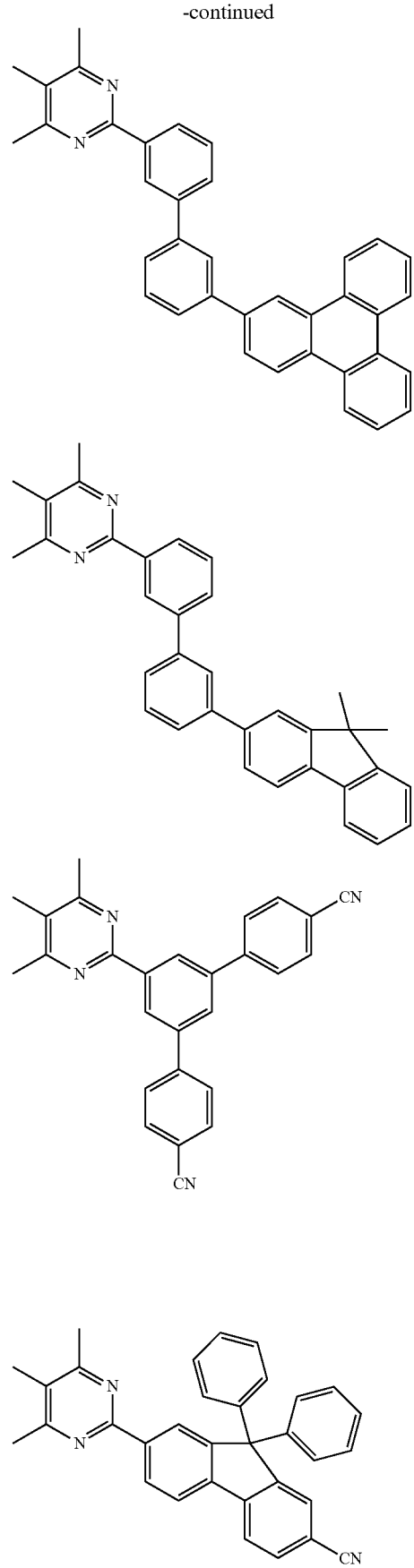

97
-continued
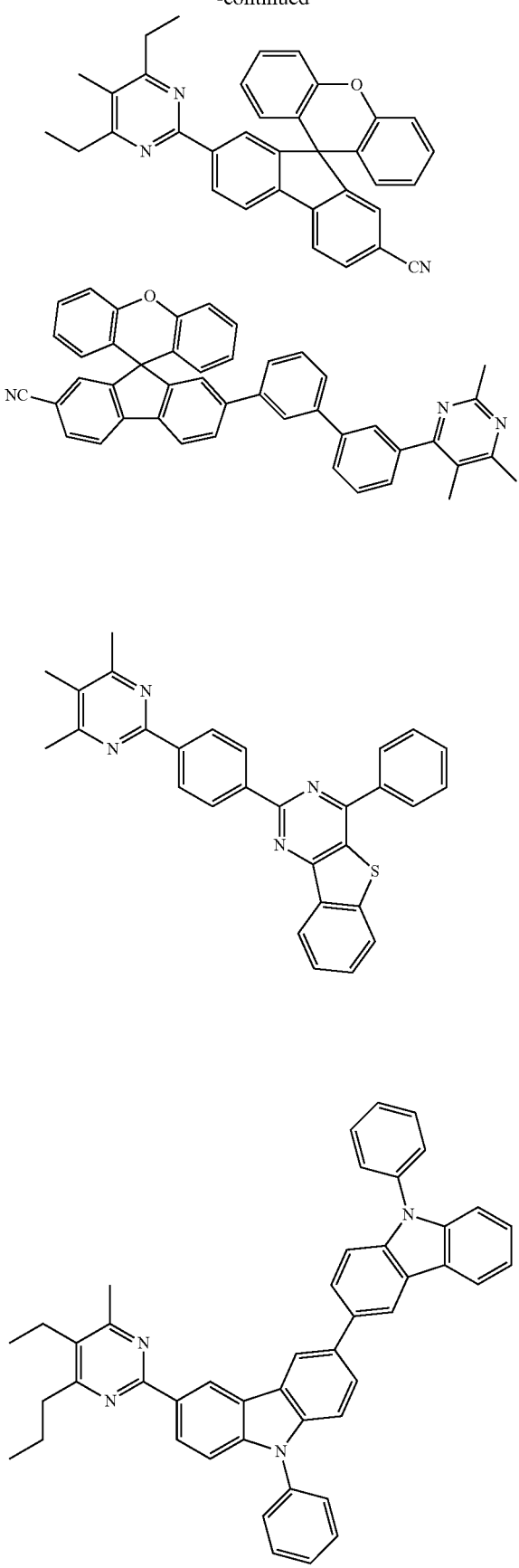
98
-continued
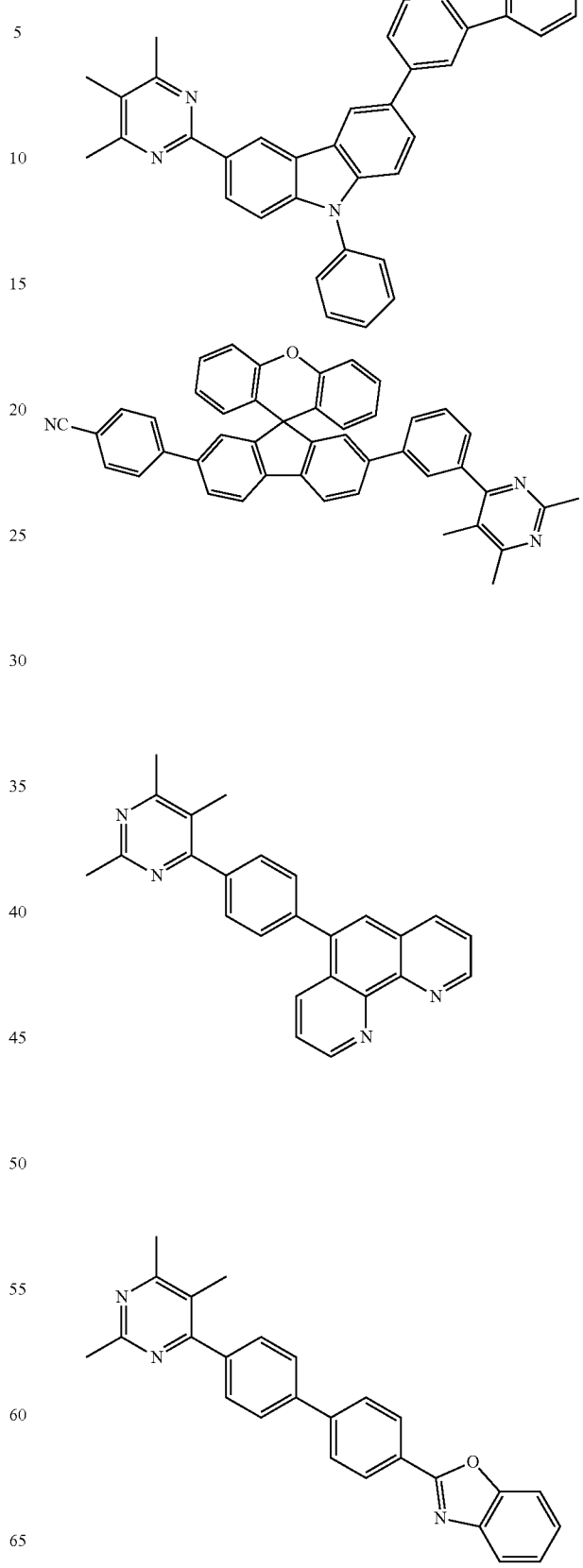

99
-continued
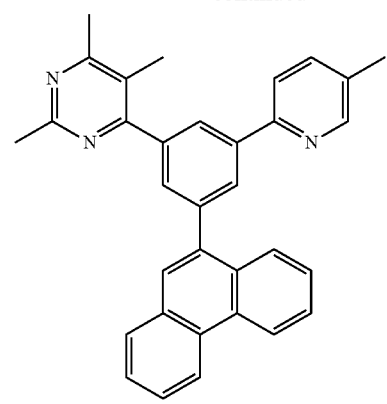
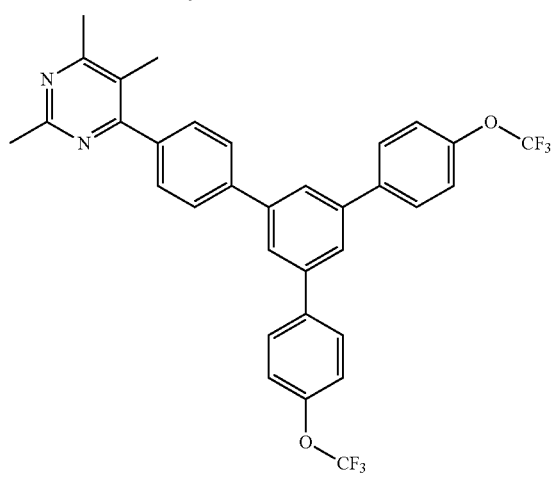
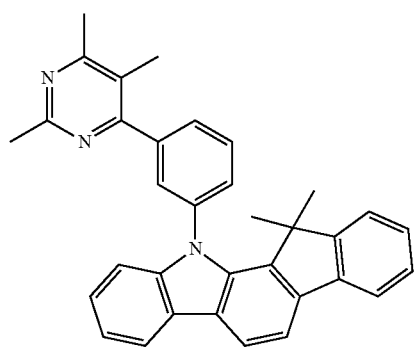
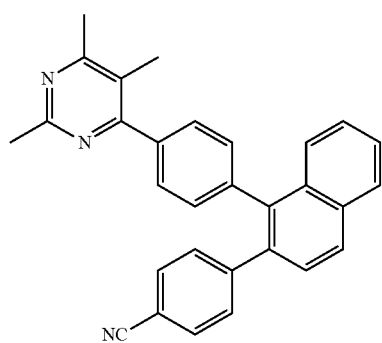
100
-continued
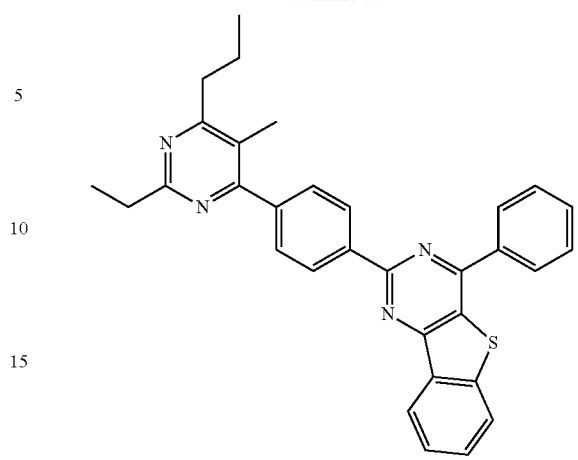
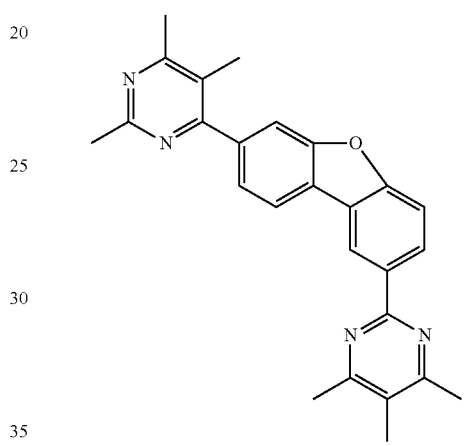
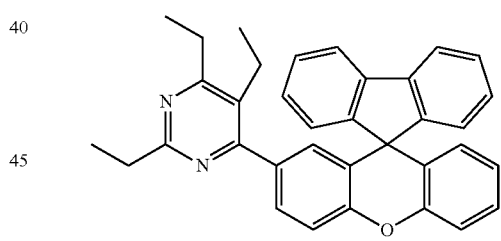
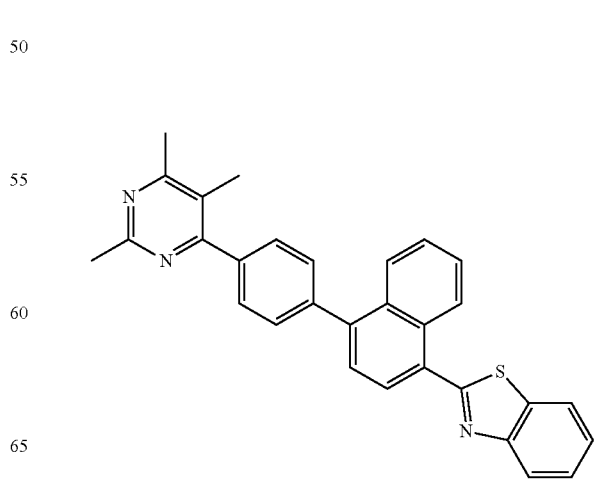

101
-continued
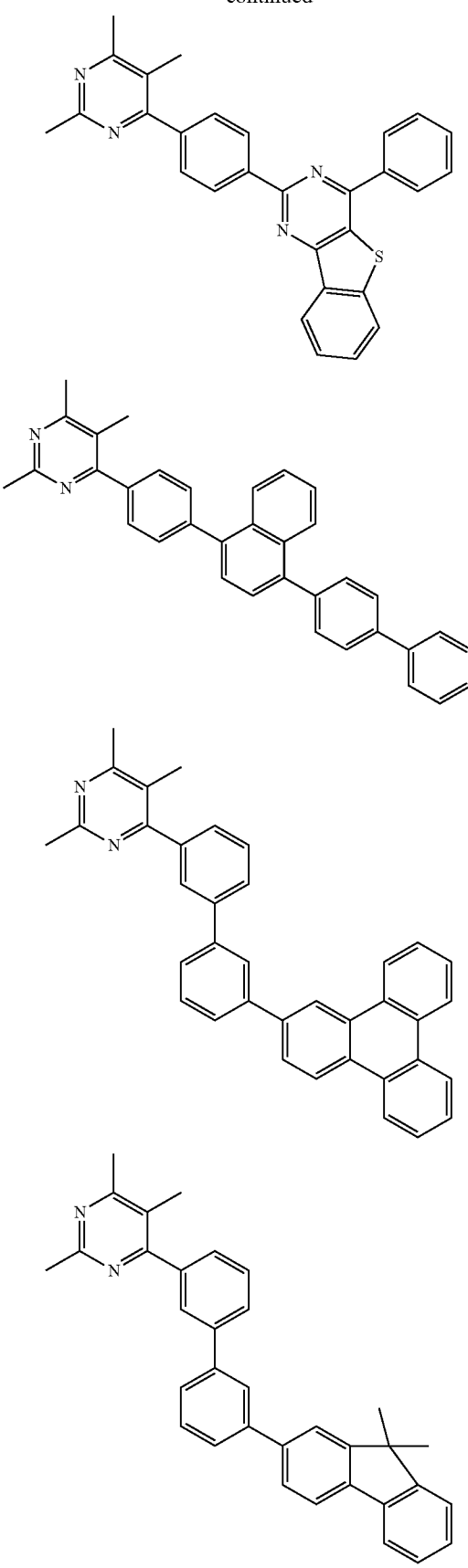
102
-continued
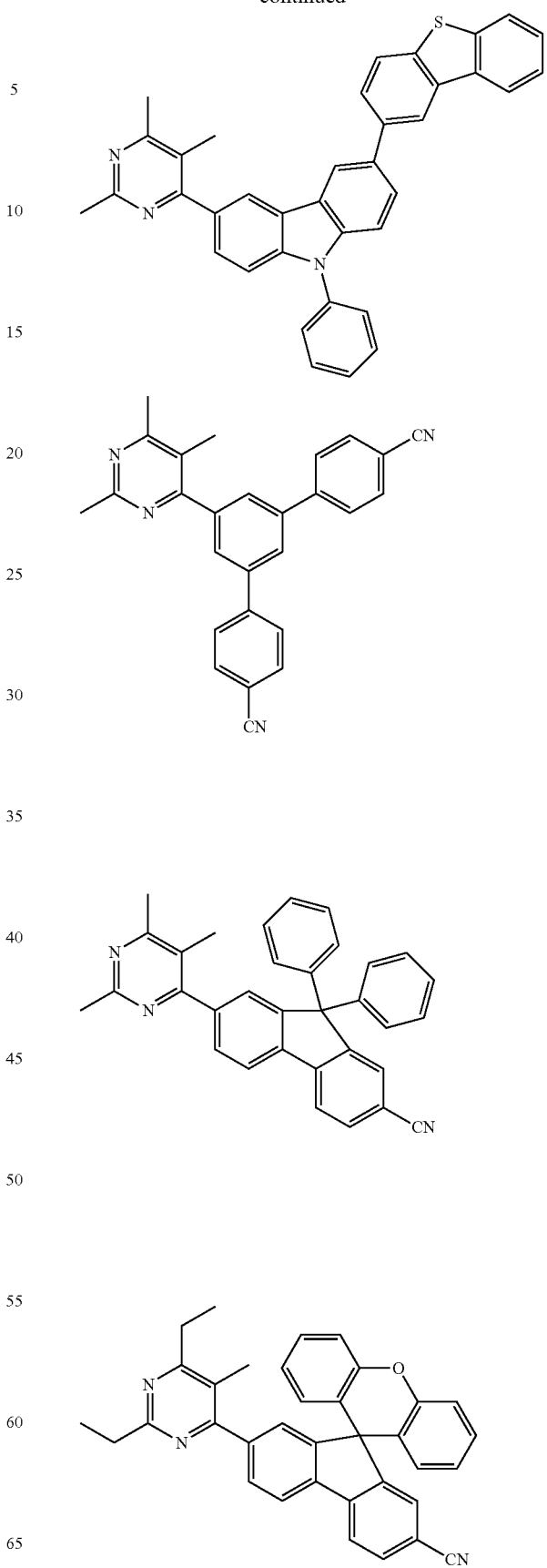

-continued
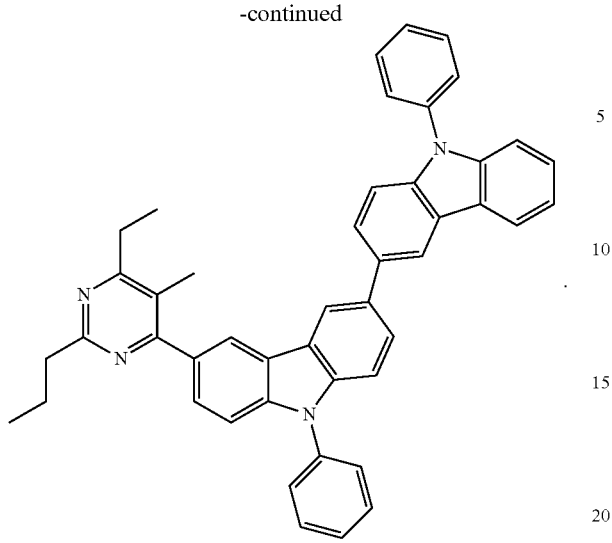
19. An organic light emitting device comprising:
a first electrode;
a second electrode provided opposite to the first electrode; and
one or more organic material layers provided between the first electrode and the second electrode,
wherein one or more layers of the organic material layers comprise the compound of claim 18.
* * * * *